United States Patent [19]

Ross et al.

[11] Patent Number: 5,617,861

[45] Date of Patent: Apr. 8, 1997

[54] MAGNETIC RESONANCE SPECTRAL ANALYSIS OF THE BRAIN FOR DIAGNOSIS OF CLINICAL CONDITIONS

[75] Inventors: Brian Ross, Altadena, Calif.; Thomas Ernst, Gundelfingen, Germany; Roland Kreis, Boll, Switzerland

[73] Assignee: Huntington Medical Research Institutes, Pasadena, Calif.

[21] Appl. No.: 197,099

[22] Filed: Feb. 16, 1994

[51] Int. Cl.$^6$ ..................................................... A61B 5/055
[52] U.S. Cl. ........................................................ 128/653.2
[58] Field of Search ............................... 128/653.2, 632; 324/307; 436/173

[56] References Cited

U.S. PATENT DOCUMENTS

| | | | |
|---|---|---|---|
| 5,109,868 | 5/1992 | Smith et al. | 128/774 |
| 5,111,819 | 5/1992 | Hurd | 128/653.2 |
| 5,182,299 | 1/1993 | Gullans et al. | 514/460 |
| 5,200,345 | 4/1993 | Young | 128/653.2 |
| 5,218,529 | 6/1993 | Meyer et al. | 364/413.01 |
| 5,283,526 | 2/1994 | Spielman et al. | 128/653.2 |
| 5,357,959 | 10/1994 | Fishman | 128/653.2 |

OTHER PUBLICATIONS

T. Ernst, et al., "Absolute Quantitation of Water and Metabolites in the Human Brain; I. Compartments and Water" *Journal of Magnetic Resonance*, Series B 102, 1–8 (1993).

R. Kreis, et al., "Absolute Quantitation of Water and Metabolites in the Human Brain. II. Metabolite Concentrations" *Journal of Magnetic Resonance*, Series B 102, 9–19 (1993).

Bruce L. Miller, et al., "Alzheimer Disease: Depiction of Increased Cerebral Myo–Inositol with Proton MR Spectroscopy"; *Radiology* 1993; 187:433–437.

Roland Kreis, et al., "Development of the Human Brain: In Vivo Quantification of Metabolite and Water Content with Proton Magnetic Resonance Spectroscopy"; *Magnetic Resonance in Medicine* 30: 424–437 (Aug. 1993).

Brian Ross, et al., "$^1$H MRS for the Diagnosis of Sub–Clinical Hepatic Encephalopathy (SCHE)"; *Proceedings, 12th Society of Magnetic Resonance in Medicine, New York;* vol. 1, 1993 p. 131.

Rex A. Moats, et al., "Cancer Markers Identified with 2–D COSY NMR on Fresh Human Prostate Samples"; *Proceedings, 12th Society of Magnetic Resonance in Medicine, New York;* vol. 2 (Aug. 1993) p. 1030.

Keiko Kanamori, et al., "A $^{15}$N NMR Study of In Vivo Cerebral Glutamine Synthesis in Hyperammonemic Rats"; *NMR in Biomedicine*, vol. 6, 21–26 (Jan., 1993).

Brian D. Ross, "Biochemical Considerations in $^1$H Spectroscopy. Glutamate and Glutamine; Myo–inositol and Related Metabolites"; *NMR in Biomedicine*, vol. 4, 59–63 (1991).

Thomas Ernst, et al., "Cerebral MRS in infant with suspected Reye's syndrome"; *The Lancet*, vol. 340:486 (Aug. 22, 1992).

(List continued on next page.)

*Primary Examiner*—Ruth S. Smith
*Attorney, Agent, or Firm*—Christie, Parker & Hale, LLP

[57] ABSTRACT

The present invention relates to a method for determining the concentration of metabolites in the brain using magnetic resonance spectrum techniques. The method comprising defining a volume within the brain, obtaining a magnetic resonance spectrum of the defined volume, suppressing the signal from water to reveal the spectra from metabolites, correcting the baseline, obtaining the magnetic resonance spectrum of an external standard, comparing the signal from the metabolites to the signal from the external standard and calculating the in vivo concentration of the metabolites. In one embodiment of the invention a diagnosis for Alzheimer Disease is made by comparing the relative peak heights of myo-inositol relative to creatine and N-acetylaspartate relative to creatine in the patient to the relative peak heights of myo-inositol relative to creatine and N-acetylaspartate relative to creatine for a normal population, wherein an increase in the relative peak height of myo-inositol and a decrease in the relative peak height of N-acetylaspartate is diagnostic of Alzheimer Disease.

15 Claims, 21 Drawing Sheets

OTHER PUBLICATIONS

Roland Kreis, et al., "Metabolic Disorders of the Brain in Chronic Hepatic Encephalopathy Detected with H–1 MR Spectroscopy"; *Radiology*, vol. 182, No. 1, Jan. 1992, pp. 19–27.

Roland Kreis, et al., "Cerebral Metabolic Disturbances in Patients with Subacute and Chronic Diabetes Mellitus: Detection with Proton MR Spectroscopy"; *Radiology*, 1992; 184: 123–130.

C.D. Smith, et al., "$^{31}$P Magnetic Resonance Spectroscopy in Alzheimer's and Pick's Disease"; *Neurobiology of Aging*, vol. 14, No. 1, pp. 85–92, 1993.

Gregory G. Brown, PhD., et al., "Altered Brain Energy Metabolism in Demented Patients With Multiple Subcortical Ischemic Lesions: Working Hypothese"; *Archives of Neurology*, vol. 50, No. 4, pp. 384–388 (Apr. 1993).

Jay W. Pettegrew, M.D., et al., "Correlation of Phosphorus–31 Magnetic Resonance Spectroscopy and Morphologic Findings in Alzheimer's Disease"; *Archives of Neurology*, vol. 45, No. 10, pp. 1093–1096 (Oct. 1988).

R. K. Gupta, et al., "Magnetic Resonance Imaging and Localized In Vivo Proton Spectroscopy in Patients with Fulminant Hepatic Failure"; *The American Journal of Gastroenterology*, vol. 88 No. 5, pp. 670–674 (1993).

Peter L. Hope, et al., "Magnetic Resonance Spectroscopy"; vol. 18 No. 3, pp. 535–548 (1991).

Jan M. Goplerud, M.D., et al., "Nuclear Magnetic Resonance Imaging and Spectroscopy Following Asphyxia"; *Clinics in Perinatology*, vol. 20, No. 2, pp. 345–367 (1993).

David K. Menon, et al., "Proton MR Spectroscopy of the Brain in AIDS Dementia Complex"; *Journal of Computer Assisted Tomography*, vol. 16, No. 4, pp. 538–542 (1992).

Akihiko Shiino, M.D., et al., "Proton Magnetic Resonance Spectroscopy with Dementia"; *Surgical Neurology*, col. 39, No. 2, pp. 143–147 (1993).

James E. Bradler, et al., "Actions of Phosphomonoesters on CA1 Hippocampal Neurons as Revealed by a Combined Electrophysiological and Nuclear Magnetic Resonance Study"; *Synapse*, vol. 9, No. 1, pp. 7–13 (1991).

James Peeling, Ph.D., et al., "$^1$H Magnetic resonance spectroscopy of extracts of human epileptic neocortex and hippocampus"; *Neurology Contents*, 1993; 43: 589–594.

Dominique Sappey–Marinier, et al., "Proton Magnetic Resonance Spectroscopy of Human Brain: Applications to Normal White Matter, Chronic Infarction, and MRI White Matter Signal Hyperintensities"; *Magnetic Resonance in Medicine*, vol. 26, No. 2, pp. 313–327 (Aug. 1992).

Michael J. Fulham, et al., "Mapping of Brain Tumor Metabolites with Proton MR Spectroscopic Imaging: Clinical Relevance"; *Radiology*, vol. 183, No. 3, pp. 675–686 (Dec. 1992).

Dominique Sappey–Marinier, et al., "Alterations in Brain Phosphorus Metabolite Concentrations Associated with Areas of High Signal Intensity in White Matter at MR Imaging"; *Radiology*, vol. 183, No. 1, pp. 247–256 (1992).

Harald Kugel, Ph.D., et al., "Human Brain tumors: Spectral Patterns Detected with Localized H–1 MR Spectroscopy"; *Radiology*, vol. 183, No. 3, pp. 701–709 (1992).

*Magnetic Resonance in Medicine*, A Report on a Workshop Held in Oxford, England, Dec. 16–18, 1992, "Advances in Proton Magnetic Resonance Spectroscopy of the Brain"; pp. 1–3.

Tetsuhito Murata, et al., "In vivo Proton Magnetic Resonance Spectroscopy Study on Premature Aging in Adult Down's Syndrome"; *Biological Psychiatry*, vol. 34, No. 5, pp. 290–297 (1993).

G. D. Graham, et al., "Proton magnetic resonance spectroscopy in Creutzfeldt–Jakob disease"; *Neurology*, vol. 43, No. 10, pp. 2065–2068 (1993).

Book Review by Oleg Jardetzky, "In Vivo Magnetic Resonance Spectroscopy I, II & III"; *TAMU NMR Newsletter*, 423: 37–38, 41 (19 ).

Brian D. Ross, M.D., PhD., et al., "Well–localized, Standardized, Quantitized Short TE $^1$H MRS Permits New Diagnostic Accuracy in Patients with Alzheimer Disease"; *TAMU NMR Newsletter*, Feb. 17, 1993, 423–13.

J. Hennig, et al., "Determination of Absolute Concentration of Metabolites by Localized in vivo–Proton Spectroscopy," Abstracts of the Society of Magnetic Resonance in Medicine, 10th Annual Meeting, Works in Progress, p. 1013 (1991).

Wehrli, PhD., et al., "Quantification of Contrast in Clinical MR Brain Imaging at High Magnetic Field," *Investigative Radiology*, vol. 20, No. 4, pp. 360–369 (1985).

R.S. Menon, et al., "Application of Continuous Relaxation Time Distributions to the Fitting of Data from Model Systems and Excised Tissue," *Magnetic Resonance in Medicine* 20, 214–227 (1991).

Peter B. Barker, et al., "$^1$H NMR Spectroscopy of Canavan's Disease,", Abstract of the Society of Magnetic Resonance in Medicine, 10th Annual Meeting, vol. 1, p. 381 (1991).

Michaelis, et al., "Quantification of Cerebral Metabolites in Man; Results Using Short–Echo Time Localized Proton MRS," Abstract of the Society of Magnetic Resonance in Medicine, 10th Annual Meeting, vol. 1, p. 387 (1991).

Harris H. Tallan, "Studies On The Distribution of N–Acetyl–Aspartic Acid in Brain," *J. Biol. Chem.*, 224 41–43 (1957).

Ognen A.C. Petroff, M.D., et al., "High–field proton magnetic resonance spectroscopy of human cerebrum obtained during surgery for epilepsy," *Neurology*, 39, 1187–1202 (1989).

R. Burri, et al., "Brain Development: $^1$H Magnetic Resonance Spectroscopy of Ray Brain Extracts Compared With Chromatographic Methods," *Neurochem. Res.*, 15 1009–1016 (1990).

Richard L. Veech, et al., "Cytosolic Phosphorylation Potential," *J. Biol. Chem.*, 254 6538–6547 (1979).

Bruce L. Miller, "A Review of Chemical Issues in $^1$H NMR Spectroscopy: N–Acetyl–L–aspartate, Creatine and Choline," *NMR Biomed.*, vol. 4, pp. 47–52 (1991).

W.W. Wells, et al., "The Isolation and Identification of Galactitol from the Brains of Galactosemia Patients," *J. Biol. Chem.*, vol. 240, pp. 1002–1004 (1965).

J. Hennig, et al. "Direct Absolute Quantification of Metabolites in the Human Brain with In Vivo Localized Proton Spectroscopy", *NMR In Biomedicine*, vol. 5, 193–199 (1992).

Peter B. Barker, et al., "Quantitation of Proton NMR Spectra of the Human Brain Using Tissue Water as an Internal Concentration Reference", *NMR in Biomedicine*, vol. 6, 89–94 (1993).

Thomas Michaelis, PhD., et al., "Absolute Concentrations of Metabolites in the Adult Human Brain in Vivo: Quantification of Localized Proton MR Spectra[1]", *Neuroradiology*, *RSNA*, pp. 219–227 (Apr. 1993).

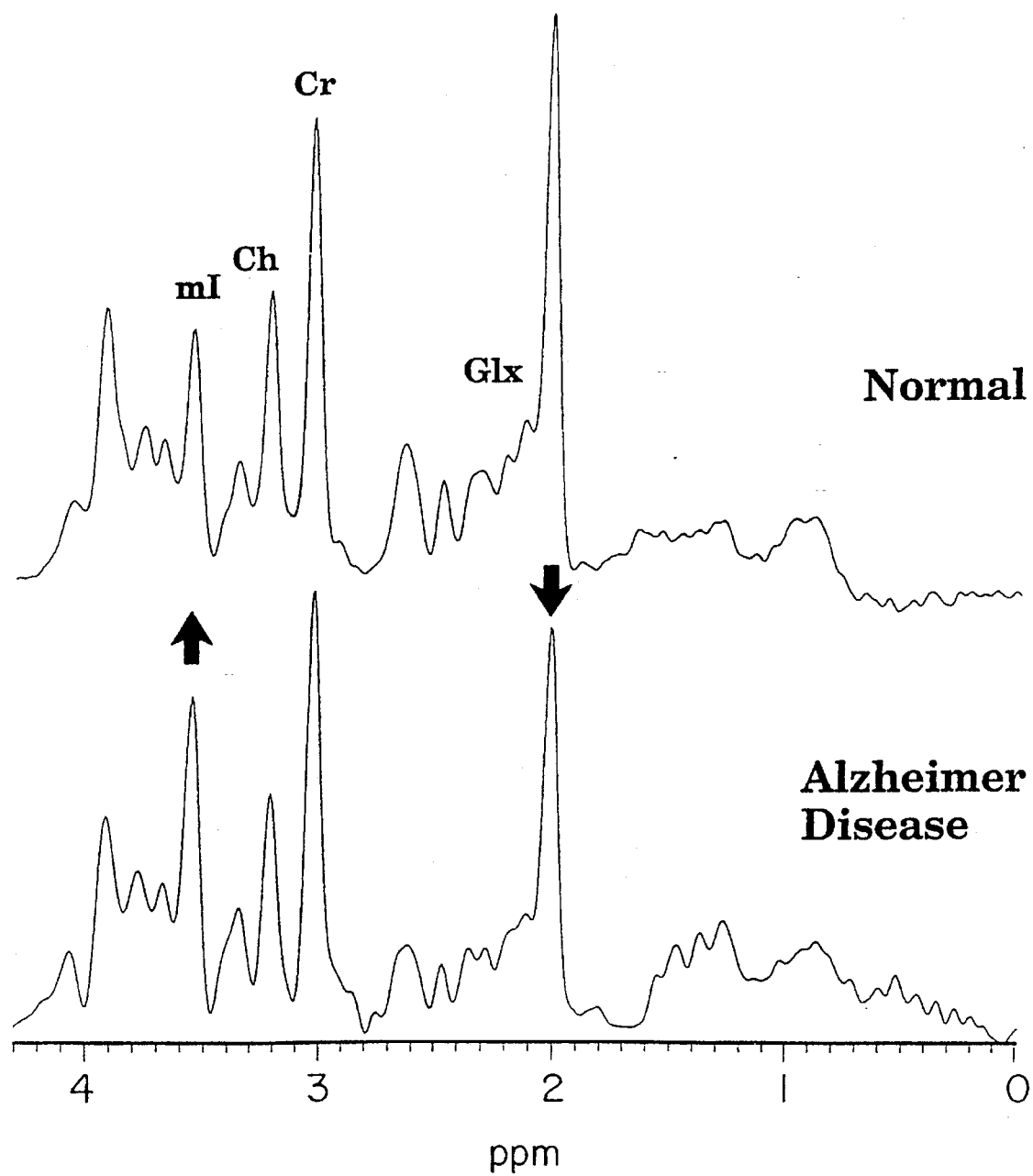

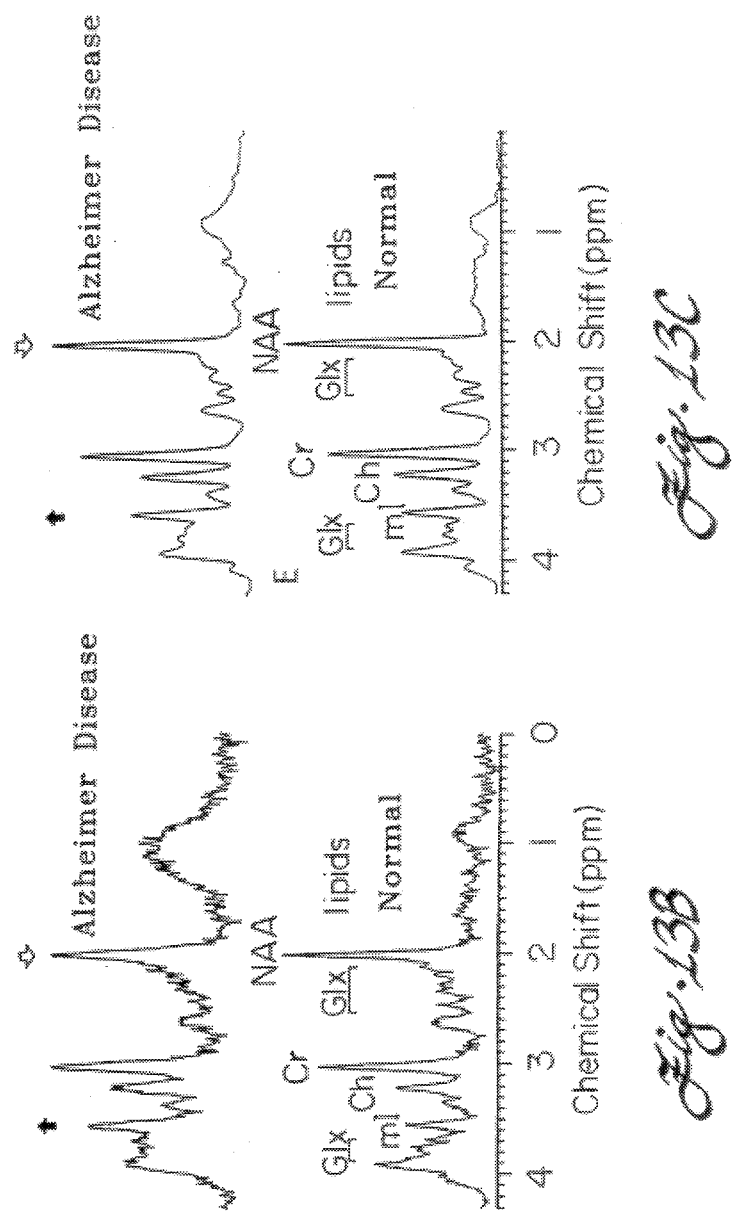
Fig. 13C
Fig. 13B
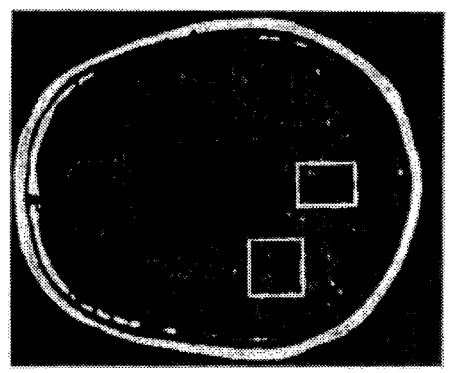
Fig. 13A

Fig. 17
Summed difference spectrum (AD minus controls)
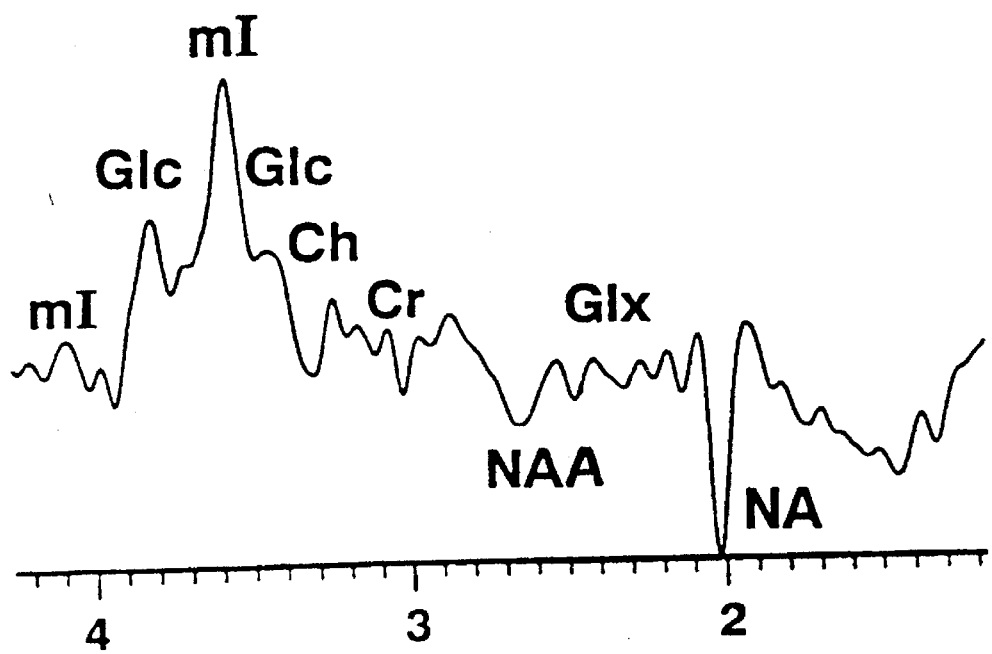
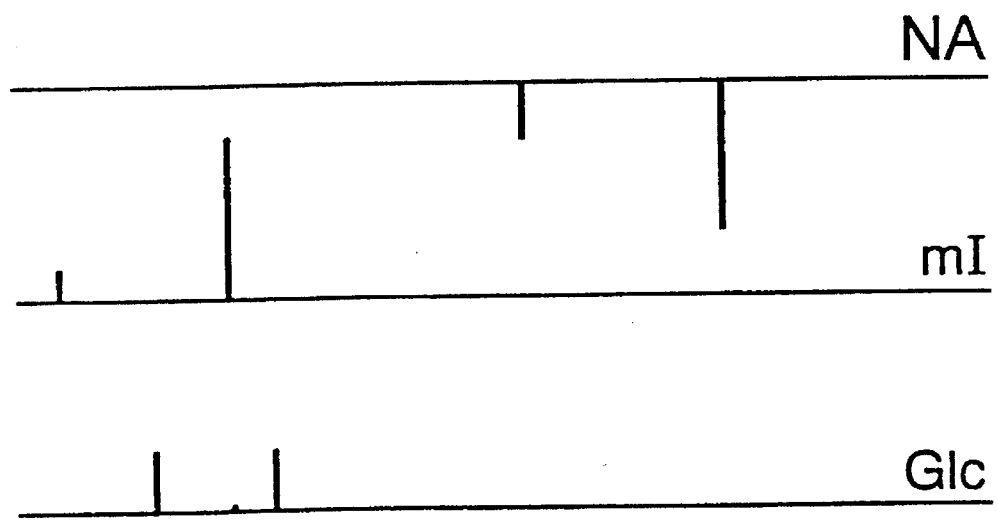

MAGNETIC RESONANCE SPECTRAL ANALYSIS OF THE BRAIN FOR DIAGNOSIS OF CLINICAL CONDITIONS

FIELD OF THE INVENTION

The invention relates to non-invasive, in situ analysis and quantitation of biochemicals in the brain as a diagnostic tool for conditions such as Alzheimer Disease using Magnetic Resonance Spectra.

BACKGROUND OF THE INVENTION

Alzheimer Disease, the major cause of dementia, is a progressive, degenerative disease characterized pathologically by extensive neuronal loss, deposits of amyloid β-peptide in brain parenchyma and meningeal blood vessels and the presence of neurofibrillary tangles within neurons. Clinical diagnosis of Alzheimer Disease, is imprecise and no biochemical markers have been identified which can be used as a basis for a laboratory test to identify the disease. Currently diagnosis of the condition relies on the observations by a physician of the condition of the patient. Such methods of diagnosis are imprecise and prone to error depending on the experience of the physician and if the symptoms exhibited by the patient are typical for the condition. Such diagnostic procedures are susceptible to a high degree of variation depending on the physicians experience and interpretation of the results or the tests which are administered. Such subjective tests and observations are also difficult to apply by others as there is no objective standard which can be applied to the test nor the results obtained.

At present, it is estimated that Alzheimer Disease is correctly diagnosed only 60 to 80% of the time. Definitive diagnosis of the dementia can only be accurately preformed upon postmortem autopsy.

It is desirable to correctly diagnose the condition of the patient so that if the dementia falls within a group of treatable dementias, appropriate treatment may be initiated. If the dementia is Alzheimer Disease, it is important to correctly diagnose the disease so that the symptoms can be more accurately established and so that a treatment regime can be investigated. If patients are misdiagnosed a large percentage of the time proposed treatments for Alzheimer Disease, which may be effective with patients who actually do have Alzheimer Disease, may be discarded as ineffective because a large portion of the test group treated was not in fact suffering from this form of dementia but from another.

It is desirable that an objective test procedure is established for diagnosing Alzheimer Disease. Such a test is preferably non-invasive or minimally invasive so that the condition of the patient is not worsened by the test procedure. Typically, objective medical diagnoses rely on biochemical tests of extracellular body fluids, such as blood or urine. However, in the case of Alzheimer Disease no biochemical basis for the disease has been firmly established. It has been speculated that deposition of amyloid β-peptide, resulting from the aberrant processing of amyloid peptide protein (APP), is the cause of Alzheimer Disease. This aberrant processing has been attributed in turn to abnormalities in the brain cell membrane, excess synthesis of amyloid precursor protein, neurotoxicity of excitatory amino acids including glutamate, or changes in the secondary messenger cascade. However, if these changes are in fact the cause or result of the changes that occur in Alzheimer Disease, none of them would be expected to produce a product which would be secreted into the extracellular body fluids for use as an Alzheimer Disease marker. Recently developed genetic markers determine the possible predisposition to develop Alzheimer Disease but are not effective in diagnosing an individual case of the disease.

Other analytical procedures rely on histological and biochemical analyses of biopsy samples. However, while these would be effective in diagnosing Alzheimer Disease they would have severe detrimental effect on the patient being diagnosed. Also biopsy samples may not accurately reflect the condition of the tissue while it was "alive" since degradation and biochemical anomalies often result after loss of oxygen and nutrients to brain tissue.

Non-invasive methods which are currently in use include magnetic resonance imaging (MRI) and magnetic resonance spectra (MRS). Since the gross anatomy of the brain is unaffected by Alzheimer Disease (except for atrophy), MRI is not expected to be a useful procedure. MRS has been used extensively to identify many chemicals in many different situation. $^{31}$P- and $^1$H-MRS have been used to identify the chemical composition of complex organic samples. Many studies have been performed in situ using $^{31}$P-MRS. Studies have used $^{31}$P-MRS to study Alzheimer Disease and have reported changes in the phospholipids in Alzheimer Disease. However, $^{31}$P-MRS is limited to chemicals which are phosphorylated. This includes only a small number of the chemicals in the body.

In U.S. Pat. No. 5,182,299 $^1$H-MRS was used as means for identifying concentrations of various biochemicals to diagnose osmotic disturbance in an animal and to monitor treatment of the condition. However, these studies relied on an in vitro analysis, which would be unsuitable for use in the diagnosis of Alzheimer Disease. Other studies have used $^1$H-MRS to study spectroscopic changes in the brain of patients with fulminating hepatic failure which showed low myo-inositol and high glutamate in grade I coma. None of the studies have identified a chemical correlation which can be associated with Alzheimer Disease. Additionally despite the potential of MRS for assessing in vivo metabolism, MRS has not yet acquired a significant place in clinical practice. The main reasons for this is the low sensitivity, low spacial resolution and low specificity due to tissue homogeneity. Another problem is that there is no way of measuring the size of the "sample" studied so that accurate concentrations of biochemicals in the sample can be calculated. This problem is generally considered to remain unsolved.

The potential of $^1$H-MRS to "observe" the biochemical concentrations in a tissue, without the need to take biopsy samples or any other type of sample makes it an ideal method for evaluating the conditions of dementia to accurately diagnose Alzheimer Disease. Therefore, it is desirable that a method is developed which will accurately determine the concentrations of chemicals in the brain to establish changes which are associated with Alzheimer Disease.

SUMMARY OF THE INVENTION

The present invention relates to a method for determining the concentration of metabolites in the brain using magnetic resonance spectrum techniques. The method comprising defining a volume within the brain, obtaining a magnetic resonance spectrum of the defined volume, suppressing the signal from water to reveal the spectra from metabolites, correcting the baseline, obtaining the magnetic resonance spectrum of an external standard, comparing the signal from the metabolites to the signal from the external standard and calculating the in vivo concentration of the metabolites.

In one embodiment of the invention a diagnosis for Alzheimer Disease is made. This method comprising defining a volume within the brain of a patient suspected of suffering from Alzheimer Disease, obtaining a magnetic resonance spectrum of the defined volume, suppressing water peak, correcting the baseline of the spectrum, locating peaks for creatine, myo-inositol and N-acetylaspartate, determining the peak height of myo-inositol relative to the peak height of creatine, determining the peak height of N-acetylaspartate relative to the peak height of creatine, comparing the relative peak heights of myo-inositol relative to creatine and N-acetylaspartate relative to creatine in the patient to the relative peak heights of myo-inositol relative to creatine and N-acetylaspartate relative to creatine for a normal population, wherein an increase in the relative peak height of myo-inositol and a decrease in the relative peak height of N-acetylaspartate is diagnostic of Alzheimer Disease.

BRIEF DESCRIPTION OF THE DRAWINGS

These and other features and advantages of the present invention will become better understood with reference to the following description, appended claims, and accompanying drawings, wherein:

FIG. 1A illustrates identification of the metabolite peaks for N-acetylaspartate (NAA) at 2.02 ppm; creatine (Cr) at 3.03 ppm; choline (Ch) at 3.23 ppm; and myo-inositol (mI) at 3.56 ppm;

FIG. 13A illustrates an MR image showing the location of voxels used;

FIG. 13B illustrates the spectra obtained from the occipital voxel, the location of which is illustrated in FIG. 13A of an Alzheimer Disease patent (top) and a healthy subject (bottom);

FIG. 13C illustrates the summed spectra obtained from the occipital voxel, the location of which is illustrated in FIG. 13A, for eight patients (top) and eight healthy subjects (bottom);

FIG. 17 illustrates abnormalities in an Alzheimer Disease population using difference spectroscopy;

DETAILED DESCRIPTION

Figure 1B:
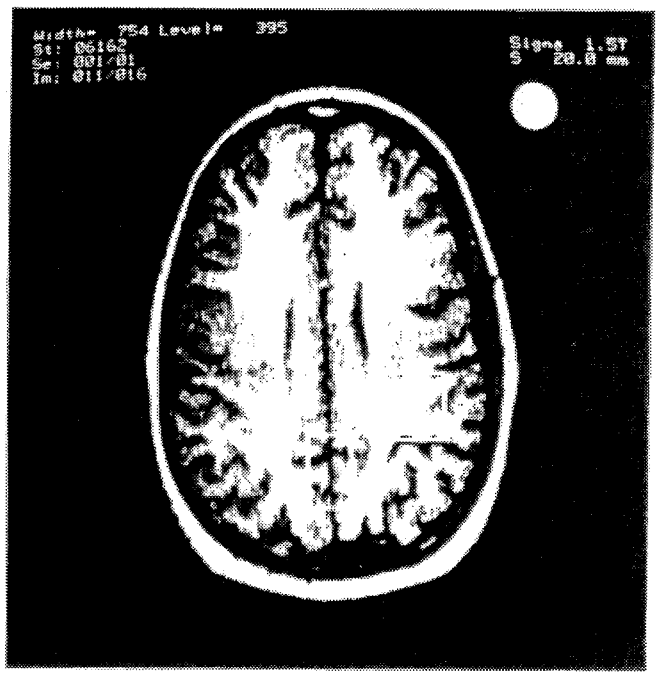
FIG. 1B illustrates the location of investigated voxels.

The present invention relates to the use of $^1$H-MRS to identify biochemical changes and quantitate metabolite levels in the brain of a patient to diagnose diseases such as Alzheimer Disease.

The aim is to provide a completely reliable and reproducible record of biochemical composition of a given region of the brain. Mostly this involves rigorously applied methods, which themselves are quantitative. But it presumes that equipment is stable, and that operator and patient induced error is minimized.

The first part of the procedure is standardization which can be used to diagnose Alzheimer Disease (because the expression used is a metabolite peak ratio, using the reliably reproducible creatine peak as the reference, not a concentration).

Once the standardization is shown to be error-free (in practice 5% error), quantitation can be applied. Diagnosis of Alzheimer Disease uses the standardization procedure whereas some other MRS diagnoses require the quantitation method.

For quantitation a box is defined. Its volume is known. This will be the divisor of the quantity of metabolites measured in the spectrum. Metabolites are only found in brain water. The proportion of the box which is brain water, cerebrospinal fluid and solid matter is determined. This allows in the Alzheimer case to a) Express brain atrophy in numbers for the first time.

b) Express metabolites per cc. of remaining brain, even though the box contains less brain in these patients, than others without atrophy.

The spectrum is calibrated in each patient by acquiring a spectrum from a standard (the external standard), of known concentration, mounted next to the patient's head, within the imaging coil.

The metabolite peaks are referenced to the external standard, and then converted to absolute concentration by reference to a once-only calibration against a standard solution in a bottle placed in the same position as the patient's head.

For rigorous quantitation of cerebral metabolites, yet further measurements have been made, and tested in patients with Alzheimer Disease, to prove that metabolite ratios truly represent changes in the metabolite concentrations described in the diagnosis of Alzheimer Disease (namely increased myo-inositol concentration and decrease in N-acetylaspartate concentration). It should be emphasize that this is part of the scientific proof, not a necessary part of the diagnostic examination.

A volume (voxel) of 10–15 ml is obtained in the gray matter of the occipital cortex of the brain. This is an area believed to have minimal clinical involvement in Alzheimer Disease. However, it is desirable to select this area of the brain since localization in this area can be performed with a high degree of reproducibility, the area is magnetically homogeneous and a "good" signal can be generated. While the placement is preferably in the occipital cortex other areas in the white matter or gray matter, such as the temporal lobe, can also be used.

In the present invention measurements are described for a General Electric (GE; Milwaukee, Wis.) Signa 1.5 T whole-body scanner with shielded gradients. The head coil is a 28 cm quadrature birdcage resonator (diameter, 28 cm; proton frequency, 63.9 MHz) with a variation in the signal intensity of only 1% over the volume used (neglecting RF penetration effects). Those skilled in the art will be aware of variations which may be required to adapt the procedure for other equipment.

Standardization

In each voxel, localized spectra are obtained by means of a stimulated-echo sequence with a $T_R$ of 1,500 ms and a $T_E$ of 30 ms. In addition, a second spectrum with a $T_R$ of 5,000 ms is obtained.

The use of two $T_R$ spectrums enables calculation of saturation factors (these factors have been shown to be not statistically significantly different between normal and Alzheimer Disease patients) and thus provided confirmation that differences in peak amplitudes were due to differences in metabolite concentrations and not due to $T_1$ relaxation effects. Except for spectral phasing, fully automated data processing is used to yield peak intensities. It consisted of four steps:

1. Digital low-frequency filtering of free induction decay (FID) for additional water suppression.

2. Lorentz-Gauss transformation to obtain similar line widths in all spectra (4 Hz) and to enhance spectral resolution. The free induction decays are zero-filled to 8,192 points (0.004 ppm per point) to make an accurate frequency alignment between different spectra possible.

3. After Fourier transformation and manual zero-order phase correction, different regions in the spectrum are separately analyzed. The main resonances in the cerebral spectrum are each attributable to a single major component and appear singletlike (2.02 ppm=N-acetylaspartate (NAA), 3.03 ppm=creatine (Cr), 3.22 ppm=choline (Ch), 3.56 ppm= myo-inositol (mI).

4. To minimize the effects of overlap, the central part of each of these peaks (1.0–1.7×line width) is used to fit a Gaussian line. Because this choice may render the fitted line widths inaccurate, peak amplitudes are used for further analysis.

In use data processing is performed by a program based on a package developed and provided by General Electric. The data processing package has been extensively modified to perform the function required for use in the present invention. The program is given in Appendix 1.

At a field strength of 1.5 T, most other components that contribute substantially to the cerebral spectrum yield complex spectral patterns, caused by strong coupling. To estimate the contribution of glutamine, an integration over a small spectral range dominated by glutamine and glutamate is performed. Accompanying changes in the α-proton ($H_\alpha$) region of glutamate and glutamine are measured by means of an integration. Two further integrations over the spectral ranges dominated by glucose are performed.

The proton spectrum of the human brain characteristically enables identification of four metabolite peaks (see FIG. 1A). They are the N-acetylaspartate (NAA) peak at 2.02 ppm; the creatine (Cr) peak at 3.03 ppm; the choline (Ch) peak at 3.23 ppm; and the myo-inositol (mI) peak at 3.56 ppm.

Quantitation

All measurements are performed with a STEAM sequence, which generates a stimulated echo of the magnetization inside the volume of interest (VOI) using three selective radio frequency (RF) pulses under orthogonal gradients. While a STEAM sequence was used in the present invention, it will be clear to those skilled in the art that other localization programs such as "PRESS" would also be suitable for use in the present invention. Detailed experimental parameters are middle interval $T_M$=13 milliseconds (ms); strength of the dephasing gradients, 10 mT/m for 10 ms; minimum echo time, 30 ms; and 1.6 ms sinc pulses with one side lobe on each side. In general, short echo times, below 100 ms, are desirable to display the metabolite myo-inositol (mI). The metabolite N-acetylaspartate (NAA) can be equally well displayed at longer echo times. The first RF pulse is phasecycled between 0° and 180°. The signal amplitudes delivered by the STEAM sequence varied by 1%, and the deviation from linearity between signal intensity and voxel size is below 1%, All signal intensities given herein are calculated directly from time-domain data (FIDs). The data acquisition is started 2 ms prior to the echo maximum (1 ms for the external standard). After the absolute value of the resulting data set is calculated, the signal intensity is determined by integrating over seven data points around the echo center (three data points for the external standard). The influence of the shim setting on the signal intensity is below 1.5%.

In the practice of the present invention a patient is placed in the head coil together with an external standard. A pilot scan (5 mm slice, $T_E$=20 ms, $T_R$=600 ms) is used to define three VOIs, shown in FIG. 1B. A "gray matter" voxel of about 10 ml is located in the occipital cortex. The "mixed parietal" voxel of (2.5 cm$^3$) consisted of mainly "white matter" with an admixture of gray matter. A 0.9×0.9×0.7 cm$^3$ voxel is placed in pure white matter in the parietal lobe. The $T_2$ measurement described below was performed on each of these voxels. Water-suppressed localized proton spectra are acquired from the mixed parietal and the occipital voxel (described below). Finally, the signal from the external reference is acquired.

An external standard for in vivo experiments must be nontoxic, have a high proton density, and resonate far from water so that a possible spillover of the water signal from the head can be identified. 100% 2-(trimethylsilyl)ethanol (TSE) (No. 22,689-0, Aldrich Chemical Co., Milwaukee, Wis.), sealed in a glass tube (2 cm diameter, 10 cm length) is used, although those skilled in the art will be aware that other standards could also be used. The reference is mounted with its long axis parallel to the $B_o$ field to minimize inhomogeneities. Its position is determined from the axial locator images, taking care of the chemical-shift artifact (frequency offset between water and TSE, 300 Hz at 1.5 T).

The signal of a 0.6×0.6×1.5 cm³ VOI inside the TSE is acquired with the STEAM sequence at $T_E$=30 ms. Because of this short $T_E$, the influence of $T_2$ variations due to changes in room temperature is below 1%. The signal to noise (S/N) ratio of a single acquisition is greater than 100:1. The spillover from brain water proved to be negligible.

The water signal detected in an MRS experiment from a localized volume V in the human brain consists of the signals from cerebrospinal fluid csf and brain tissue. A STEAM experiment performed with an echo time $T_E$, a middle interval $T_M$, and a recovery time $T_r$ delivers the signal $S(T_E, T_M, T_r)$:

$$S(T_E, T_M, T_r) = S_{csf} \exp(-T_E/T_{2csf}) \times \exp(-T_M/T_{1csf})[1-\exp(-T_r/T_{1csf})] + S_{bw} \exp(-T_E/T_{2bw}) \exp(-T_M/T_{1bw}) \times [1-\exp(-T_r/T_{1bw})]; \quad [1]$$

where $T_1i$ and $T_2i$ is the longitudinal and transverse relaxation times of the spins in compartment i (=csf, bw). The aim is to determine $S_{csf}$ and $S_{bw}$, representing the signal amplitudes of cerebro spinal fluid (csf) and brain water (bw) without relaxation.

The double-exponential decay of the water signal with $T_E$, described by Equation [1], is measured by varying the echo times of the STEAM sequence ($T_E$=30, 45, 67.5, 101, 200, 500 and 1500 ms; $T_M$=13 ms; $T_r$=30 s). The signal intensities for csf and brain water are extracted with a standard least-squares fitting procedure. The component with the longer $T_2$ is assigned to csf. The correction due to signal decay in the $T_m$ period is very small (<3%) because the $T_m$ time used (13 ms) is very short compared to even the smallest $T_1$ values in the brain (520 ms for white matter).

The MRS signal $S_i$ generated by species i in an MRS experiment is proportional to the number of spins $n_i$ involved:

$$S_i = k n_i. \quad [2]$$

The proportionality constant k depends on experimental conditions such as the loading of the RF coil and receiver gain factors. Equation [2] can be rewritten $$S_i = k m_i l_i / M_i = k V_i \rho_i l_i / M_i \quad [3]$$

with $m_i$=mass, $M_i$=molecular weight, $V_i$=volume, $\rho_i$=density, and $l_i$=number of visible protons per molecule of species i. For each new study, the constant k is determined from the signal $S_{tse}$ of the external standard (voxel size $V_{tse}$).

To measure an invisible compartment, the signal $S_h(V)$ that would be generated by a volume V of pure water needs to be determined. Using the signal $S_{tse}$ of the external standard to determine the loading, $S_h(V)$ is $$S_h(V) = kV\rho_w l_w/M_w = cS_{tse}(V/V_{tse}). \quad [4]$$

The new constant c can be determined by comparing the signal from a water phantom to that of the external reference. This is done by performing a STEAM experiment at several echo times to extract the hypothetical amplitudes at $T_E$=0. The positions of the voxels in the TSE tube and the water phantom are close to those used for in vivo experiments. The constant c proved to be reproducible within 2% over a period of several months.

Figure 2A:
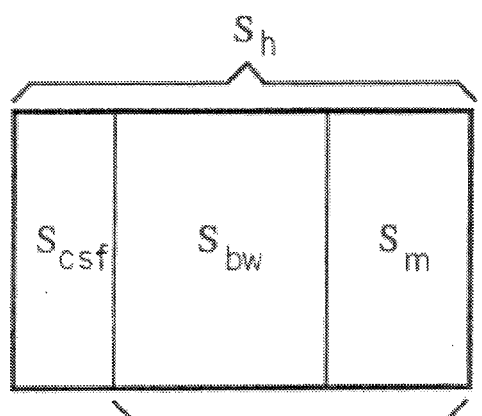
FIG. 2A illustrates the compartmentation model of the human brain in terms of an MRS signal.

The information for analyzing the compartmentation of the brain is now available. The situation is illustrated in FIG. 2A. The signals $S_{csf}$, $S_{bw}$, and $S_h$ is known, so that a missing signal $S_m$ and a (hypothetical) signal $S_b$ from the total brain can be defined:

$$S_m = S_h - S_{bw} - S_{csf} \quad [5]$$

$$S_b = S_{bw} + S_m. \quad [6]$$

$S_m$ characterizes that part of the brain tissue which is not MRS-visible under the applied conditions and is thus closely related to structural material or the dry weight. $S_b$ gives the signal that would arise from brain tissue consisting of pure water.

$$s_i = S_i/S_h \quad (i=\text{csf, bw, m, or b}); \quad [7]$$

$$s_{csf} + s_{bw} + s_m = s_{csf} + s_b = 1. \quad [8]$$

Figure 2B:
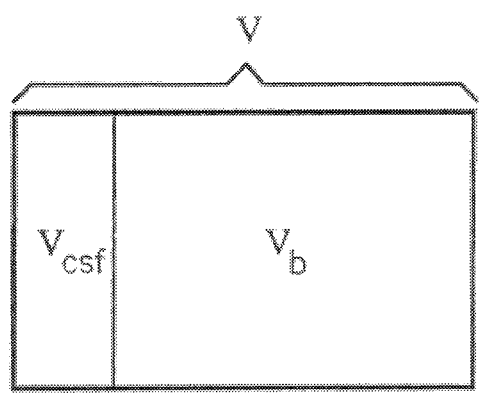
FIG. 2B illustrates the compartmentation model of the human brain in terms of volume.
Figure 2C:
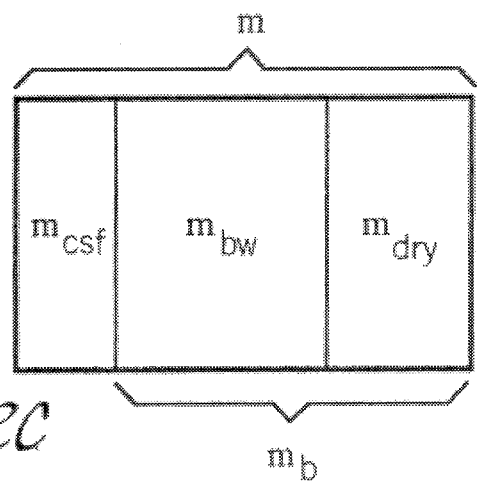
FIG. 2C illustrates the compartmentation model of the human brain in terms of mass.

The volumes and masses of the compartments, as shown in FIGS. 2B and 2C, can now be calculated. Equations [3] and [4] yield for the volume $V_{csf}$ $$V_{csf} = S_{csf} M_{csf}/(k\rho_{csf} l_{csf}) = V s_{csf} \quad [9]$$

using the (valid) approximation of csf being pure water. The volume $V_b$ of brain tissue is then (see FIG. 2B)

$$V_b = V - V_{csf} = V s_b. \quad [10]$$

No individual volumes will be attributed to tissue water and structural material, because these two compartments cannot be separated on a macroscopic level.

The masses of the compartments can be calculated similarly (FIG. 2C)

$$m_{csf} = V\rho_w s_{csf} \quad [11]$$

$$m_b = V\rho_b s_b \quad [12]$$

$$m_{bw} = (S_{bw} M_w)/(k l_w) = V\rho_s s_{bw}. \quad [13]$$

Finally, the dry weight $m_{dry}$ can be calculated (FIG. 2C), $$m_{dry} = V(\rho_b s_b - \rho_w s_{bw}), \quad [14]$$

where $\rho_b$ and $\rho_w$ are the densities of brain tissue and pure water, respectively.

The water content of the brain $\beta_{MR}$ as measured with MRS is defined as the ratio of signals from tissue water $S_{bw}$ and total brain $S_b$ $$\beta_{MR} = S_{bw}/S_b. \quad [15]$$

In contrast, biochemistry defines the water content as the ratio of the tissue water mass and the wet weight mass and the wet weight ($\beta_{BC}=m_{bw}/m_b$). Inserting Equations [12] and [13] yields $$\beta_{BC}=\beta_{MR}(\rho_w/\rho_b). \quad [16]$$

Therefore, to compare the values determined with the two methods, the differing densities of water and brain tissue must be taken into account.

An atrophy index $\alpha_1$ is the csf content of a given voxel, which is equal to the relative signal strength $S_{csf}$ as defined in Equation [17]:

$$\alpha_1=s_{csf}=S_{csf}/S_h. \quad [17]$$

This atrophy index ranges from 0 to 1; $\alpha_1$ is most sensitive to atrophy if the chosen voxel covers a greater part of gyri, such as a gray matter voxel in the midline occipital cortex. It is a disadvantage that the calculation of $\alpha_1$ requires the measurement of both $T_2$ decay (for $S_{csf}$) and the external reference (for $S_h$). An alternative atrophy index can be defined which refers the signal from csf to the total visible MRS signal and thus does not depend on the external standard:

$$\alpha_2=S_{csf}/(S_{csf}+S_{bw}). \quad [18]$$

In the literature a cornucopia of concentration measures has been used. Those most frequently encountered in the context of compartmentation of the brain is discussed below. All concentrations are related to $c_w$ (moles of metabolite per total volume) using the nomenclature described above.

If there is no information about the compartmentation of the measured voxel, the metabolite signal can only be referred to the volume of the localized region. The effects of coil loading and hardware amplification factors can be eliminated through the use of an external standard, $$ct_v=n_{met}/V=\gamma S_{met}/(l_{met}S_{tse}V) \quad [19]$$

with a calibration constant, $\gamma=V_{tse}\rho_{tse}l_{tse}/M_{tse}$. In practical terms, $\gamma$ is best determined with standard solutions as described in which case it also incorporates the difference in the way $S_{met}$ (peak area) and $S_{tse}$ (FID amplitude) are calculated.

The calculation of moles of metabolite per total voxel mass presupposes a knowledge of the compartmentation. If this is known, it is preferable to use one of the following units.

Most biochemical measurements in brain analysis are tabulated as moles per total weight of the analyzed sample (drained of csf; the occurrence of $s_b=1-s_{csf}$ reflects this correction):

$$c_{bm}=N_{met}/M_b=c_{tv}/(\rho_b S_b). \quad [20]$$

To convert $C_{bm}$ to molar units, where the volume of the localized brain tissue is considered the volume of the "chemical solution," $c_{bm}$ is simply multiplied with $\rho_b$:

$$c_{bv}=c_{tv}/s_b \quad [21]$$

The similar concentration measure defined by Henning et al. (Abstracts of the Society of Magnetic Resonance in Medicine, 10th Annual Meeting Works in Progress p1013, 1991) which is incorporated herein by reference), assuming a water content of 100%, is an overestimate of $c_{bv}$.

All concentrations defined above require the measurement of an external standard. It is, however, possible to refer metabolite levels directly to the brain water within the localized area. This concentration, which is molal in the chemical sense, is easier to determine and also very useful for metabolites dissolved in water but not prominent in the structural material of the brain. It is closely related to concentrations to be used in equilibrium and kinetic calculations, the missing information being the distribution among different cell types and intra- and extracellular fluid:

$$c_{wm}=n_{met}/m_{bw}=c_{tv}/(\rho_w s_{bw}) \quad [22]$$

$$c_{wm}=c_{bm}/\beta_{BC}. \quad [23]$$

A further desirable unit is moles of metabolite per volume of tissue water, $c_{wv}$. However, the density of tissue water cannot easily be defined, so that $c_{wv}$ would rely on assumptions.

A concentration unit used fairly often in chemical analyses is moles of metabolite per dry mass of tissue. This unit, too, can be determined from the compartmentation model (Equation [14]):

$$c_{dw}=n_{met}/m_{dry}=c_{tv}/(\rho_b s_b-\rho_w s_{bw}) \quad [24]$$

$$=c_{bm}/(1-\beta_{BC}). \quad [25]$$

EXAMPLE 1

Absolute Quantitation of Water and Metabolites in the Human Brain: Compartment and Water All experiments were performed on a GE (Milwaukee, Wis.) Signa 1.5 T whole-body scanner with shielded gradients. The head coil was a 28 cm quadrature birdcage resonator (diameter, 28 cm; proton frequency, 63.9 MHz), with a variation in the signal intensity of only 1% over the volume used (neglecting RF penetration effects).

All experiments were performed with a STEAM sequence, which generates a stimulated echo of the magnetization inside the volume of interest (VOI) using three selective RF pulses under orthogonal gradients. Detailed experimental parameters were middle interval $T_M=13$ ms; strength of the dephasing gradients, 10 mT/m for 10 ms; minimum echo time, 30 ms; and 1.6 ms sinc pulses with one side lobe on each side. The first RF pulse was phase-cycled between 0° and 180°. The signal amplitudes delivered by the STEAM sequence varied by 1%, and the deviation from linearity between signal intensity and voxel size was below 1%.

All signal intensities were calculated directly from time-domain data (FIDs). The data acquisition was started 2 ms prior to the echo maximum (1 ms for the external standard). After the absolute value of the resulting data set was calculated, the signal intensity was determined by integrating over seven data points around the echo center (three data points for the external standard). The influence of the shim setting on the signal intensity was below 1.5%.

Ten healthy volunteers (22 to 34 years old, 5 females/5 males) were placed in the head coil together with the external standard. A pilot scan (5 mm slice, $T_E=20$ ms, $T_R=600$ ms) was used to define three VOIs, shown in FIG. 1B. A "gray matter" voxel of about 10 ml was located in the occipital cortex. The "mixed parietal" voxel of (2.5 cm³) consisted of mainly "white matter" with an admixture of gray matter. A 0.9×0.9×0.7 cm³ voxel was placed in pure white matter in the parietal lobe. The $T_2$ measurement was performed on each of these voxels. Water-suppressed localized proton spectra were acquired from the mixed parietal and the occipital voxel. Finally, the signal from the external reference was acquired.

An external standard of 100% 2-(trimethylsilyl)ethanol (TSE) (No. 22,689-0, Aldrich Chemical Co., Milwaukee, Wis.), sealed in a glass tube (2 cm diameter, 10 cm length). The reference was mounted with its long axis parallel to the $B_o$ field to minimize inhomogeneities. Its position was determined from the axial locator images, taking care of the chemical-shift artifact (frequency offset between water and TSE, 300 Hz at 1.5 T).

The signal of a 0.6×0.6×1.5 cm³ VOI inside the TSE was acquired with the STEAM sequence at $T_E$=30 ms. Because of this short $T_E$, the influence of $T_2$ variations due to changes in room temperature was below 1%. The S/N ratio of a single acquisition was greater than 100:1. The spillover from brain water proved to be negligible.

Figure 3:
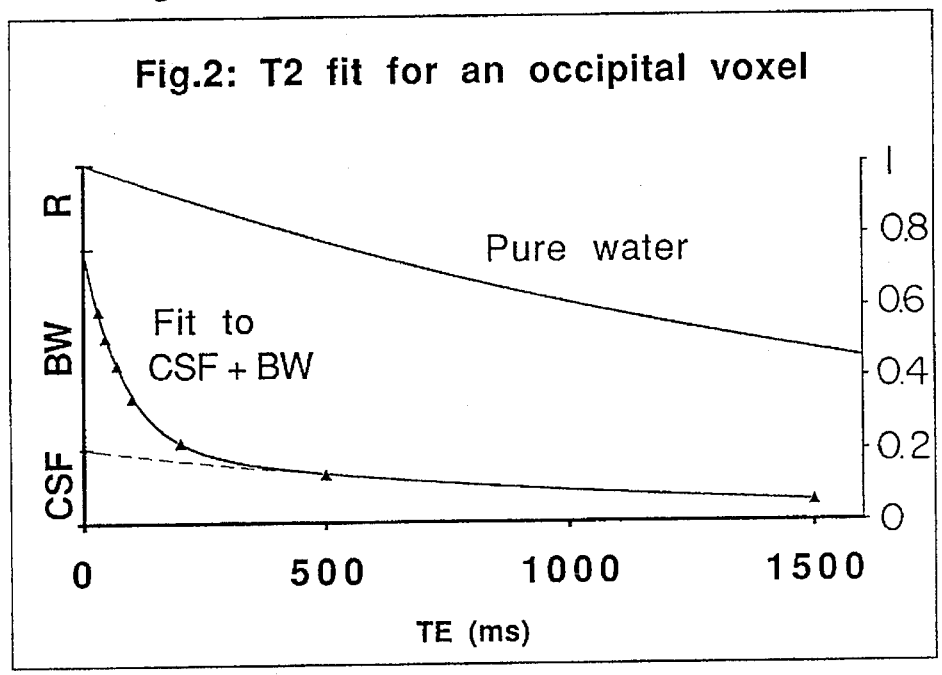
FIG. 3 illustrates the double-exponential $T_2$ decay of the water signal in human brain.

FIG. 3 shows the result of a $T_2$ measurement in gray matter of a 70-year-old healthy volunteer. The fitted double-exponential decay (solid line) follows the data points (triangles). The signals $S_{csf}$ from csf and $S_{bw}$ from brain water, reflecting the signals amplitudes at $T_E$=0, are also indicated. The csf part (dashed line) was high in this case (36% of the MRS signal) due to cortical atrophy. The hypothetical signal $S_h$ from pure water under identical loading is considerably higher than the added signal $S_{bw}+S_{csf}$, so that a missing signal $S_m$ can be defined (see Equation [5]).

The group of younger volunteers showed that the differentiation between csf and brain water works reliably down to csf levels of 1%. This interpretation is supported by the $X^2$ values provided by the fitting procedure. The capacity to detect small amounts of csf even against the high background of brain water is due to the large difference in the $T_2$ values. The measured $T_2$ values of white and gray matter are 85±4 and 79±2 ms, respectively and thus about 10 times smaller than those of csf.

The result of the $T_2$ measurement may be influenced by the presence of blood, which has an intermediate $T_2$ of approximately 250 ms. A computer study was performed in which a small component with a $T_2$ of 250 ms was added to a simulated double-exponential decay with parameters typical for brain water and csf. The simulations showed that approximately one-third of the signal from blood is assigned to both csf and tissue water, while one-third is not detected.

The $T_2$ measurement might furthermore be distorted by diffusion effects. This would mainly lead to an underestimation of csf, because its diffusion coefficient is larger than that of brain water, and because it is the component with the longer $T_2$. Experiments and theoretical calculations demonstrate, however, that, with the gradients used, the attenuation of the csf signal is considerably below 1% even at the longest $T_E$ value.

Figure 4:
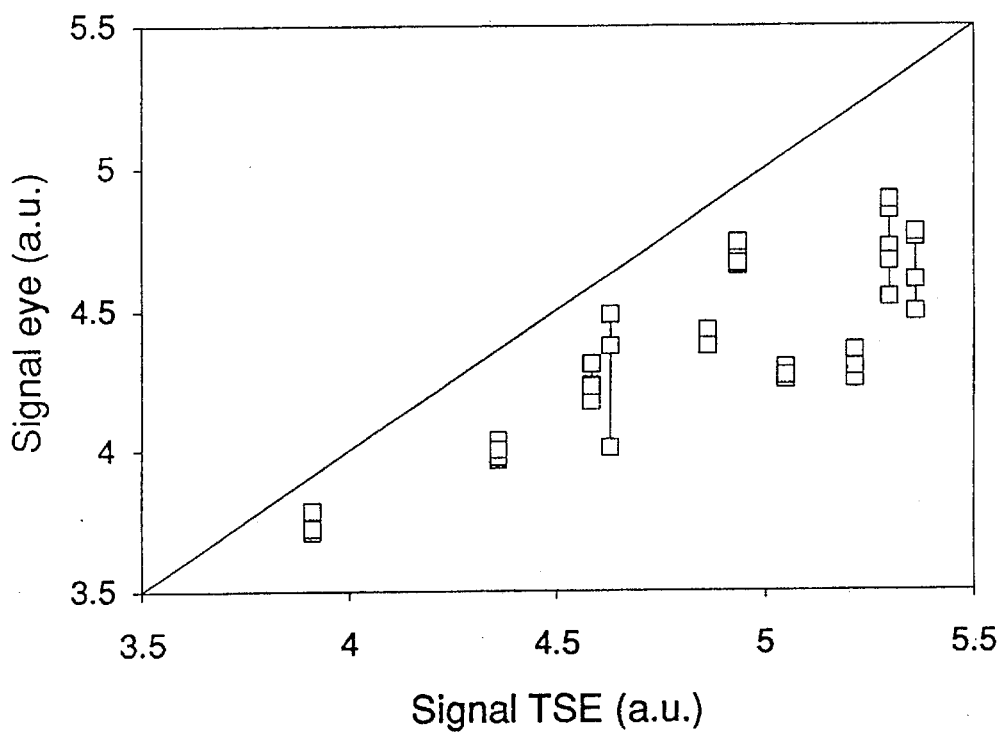
FIG. 4 illustrates the signal from the eyeball in 10 healthy individuals vs. signal from the external reference (TSE)

On several volunteers, an attempt was made to evaluate the validity of internal concentration references consisting of pure water. One possibility is to use aqueous humor in the eye, the water content of which is more than 99%. FIG. 4 shows that considerable variations in the signal amplitudes under repeated measurements were observed (probably due to motion of the eyes), so that the eyeball does not seem to be appropriate as an internal standard.

Csf might also be used as an internal reference. In this case, however, the smallness of the ventricles in some volunteers lead to partial volume effects, so that intraventricular csf is generally not a reliable internal standard either.

Despite these problems, the water content of aqueous humor and csf was 97% in some of the volunteers examined, which gives confidence in the concept of the external standard and, in turn, the hypothetical signal from pure water $S_h$ as defined in Equation [4] above.

Figure 5:
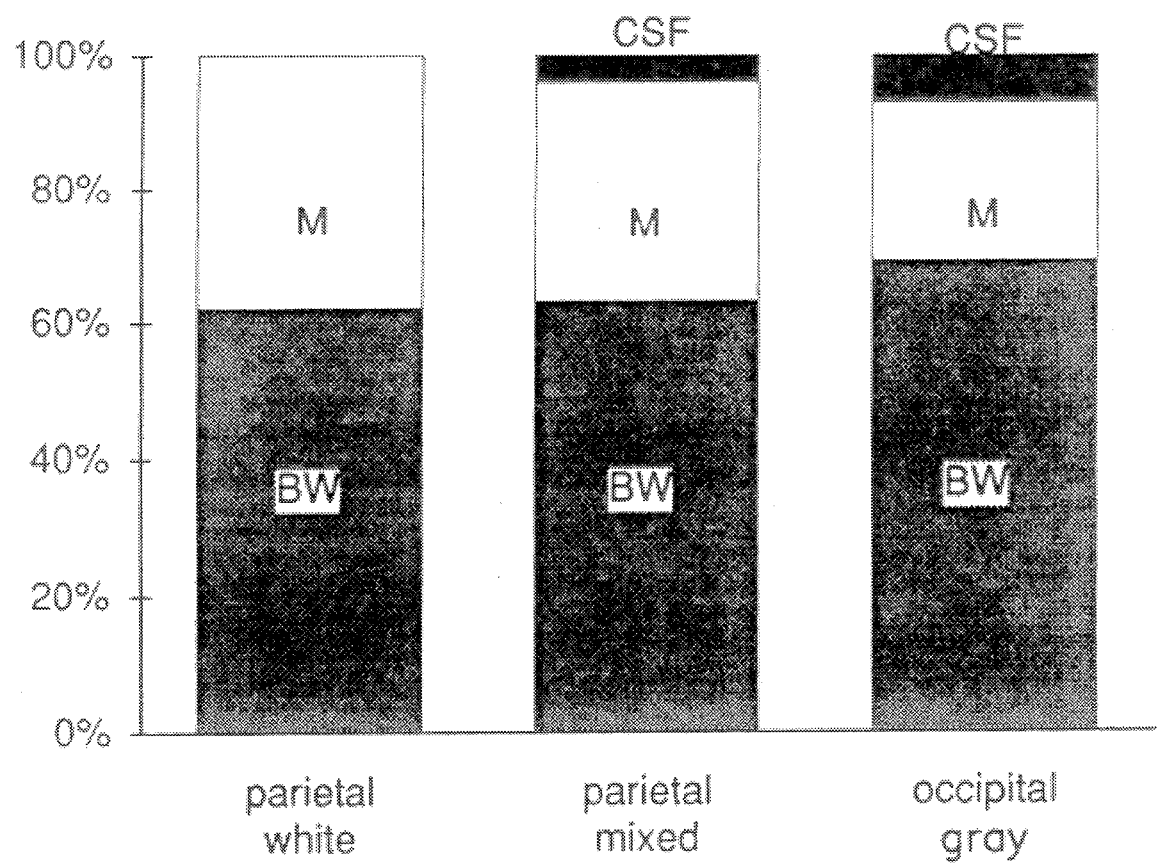
FIG. 5 illustrates the average composition of three regions in the human brain.

The average voxel composition measured in the group of 10 volunteers is shown in FIG. 5. The exact values, given as relative signal strengths from Equation [7] above, are listed in Table I. With a statistical error of 2%, the measured values are very precise. In the case of the csf content, this reflects the fact that a homogeneous group of young volunteers without atrophy was examined. The small errors in $S_{bw}$ and $S_m$ demonstrate the reproducibility of the experiments.

TABLE I

| Average Voxel Composition in 10 Volunteers | | | |
|---|---|---|---|
|  | Gray Matter | Mixed Parietal | White Matter |
| Volume (ml) | 10.8 | 15.3 | 0.57 |
| $S_{bw}$ | 0.723 ± 0.020 | 0.666 ± 0.020 | 0.646 ± 0.015 |
| $S_{csf}$ | 0.075 ± 0.020 | 0.037 ± 0.010 | ≤0.02[a] |
| $S_m$ | 0.202 ± 0.020 | 0.297 ± 0.020 | 0.354 ± 0.015 |
| $\beta_{MR}$ | 0.780 ± 0.015 | 0.691 ± 0.015 | 0.646 ± 0.015 |
| $\beta_{MR}(\rho_w/\rho_b)$ | 0.745 ± 0.015 | 0.660 ± 0.015 | 0.617 ± 0.015 |
| $\beta_{BC}$ | 0.82 | — | 0.73 |
| $\alpha_1 = S_{csf}$ | 0.075 ± 0.02 | 0.037 ± 0.01 | ≤0.02[a] |
| $\alpha_2$ | 0.095 ± 0.03 | 0.053 ± 0.015 | ≤0.03[a] |

Note.
$S_{bw}$, $S_{csf}$ and $S_m$ as defined in Equation [7], indicate the relative signal strengths of tissue water, csf, and missing signal; $\beta_{MR}$ is the water content of brain tissue as measured with MRS, whereas according to Equation [16], $\beta_{MR}(\rho_w/\rho_b)$ can be directly compared with the biochemical value $\beta_{BC}$; and $\alpha_1$ and $\alpha_2$ represent the two cortical atrophy indices defined in Equations [17] and [18].
[a]No signal from csf was detected in the pure white matter voxel.

No long $T_2$ component, i.e., csf, could be identified in the pure white matter region. The upper limit of 2% given in Table I was obtained by computer simulations and corresponds to the smallest component with a $T_2$ of 1,500 ms that would have been detected by the fitting algorithm. The value mainly reflects the rather limited signal-to-noise ratio (50:1 at $T_E$=30 ms) which results from the very small voxel size of 0.55 ml compared to more than 10 ml in the other two regions. The lower limit for detecting blood with a $T_2$ of 250 ms was approximately 5%, which is well above the value of 2.2% cited by others. Therefore, a monoexponential function was used to describe the $T_2$ decay in pure white matter. The $\chi^2$ values delivered by the fitting routine support the quality of the fit.

Table I also lists the average values for the brain water content. The water content $\beta_{MR}$, defined in Equation [15], can be used to calculate the ratio of white to gray matter in the mixed parietal voxel. The water content $\beta(p)$ of a region containing a portion p of white matter and (1−p) of gray matter is $$\beta(p)=p\beta_{white}+(1-p)\beta_{gray}. \qquad [26]$$

Using the values from Table I, the ratio of white to gray matter in the mixed parietal region turns out to be 2:1 (p=0.66±0.20).

The average csf content at different locations varies as expected from anatomical considerations (Table I). No csf can be detected in the parietal pure white matter voxel (with an upper limit of 2%), whereas the gray matter voxel, due to its location in the midline occipital cortex, has an average csf content of 7.5%. The mixed parietal voxels give an intermediate value of 3.7%. Several older volunteers and patients showed a relative csf signal $s_{csf}$ (atrophy index $\alpha_1$) as high as 25% in gray matter. Obviously, such a high csf compartment cannot be neglected in quantitative studies.

The results obtained are in agreement with those published by others. Using $T_2$-weighted proton images and special segmentation software, the percentage of extraventricular csf on total brain was determined to be 12% in a group of subjects with an average age of 71 years. The lower number determined can be attributed to the use of total brain volume as reference; this includes larger regions without csf, such as white matter.

The atrophy index $\alpha_2$, as defined in Equation [18], is 9.5% in the occipital region in the younger volunteers and 35–40% in the older subjects; $\alpha_2$ is much easier to measure than the atrophy index $\alpha_1$, or atrophy indices determined from $T_2$-weighted images with special segmentation software.

FIG. 5 shows that the amounts of brain water and invisible rest differ considerably between gray and white matter. The water content $\beta_{MR}$ as defined in Equation [15] is listed in Table I. The values for gray and white matter are 0.78 and 0.65, respectively. The small standard deviations of ±0.015 demonstrate the reproducibility of the experiments. However, even this small statistical error might be too large for routine determination of cerebral edema.

Wehrli et al. (*Invest. Radiol.* 20 379, 1985) measured the proton densities of gray and white matter with MRI. Their values of 0.86 and 0.76, with relatively high statistical errors of ±0.1, are higher than those of the present study. In their study, proton densities were calculated by referring the signals from brain tissue to that from csf. In the present study on two volunteers, applying a spin-echo imaging technique with a long $T_R$ of 6 s and a short $T_E$ of 11 ms, revealed that the signal from csf was 10–20% lower than that from an external water reference and varied considerably over the ventricles. Thus, csf does not seem to be a valid internal standard. These findings might explain the higher values found in their study.

To compare the water content measured with MRS to that determined biochemically, the MRS value must be multiplied by the ratio of the densities of pure water and brain tissue (see Equation [16]). The density of both gray and white matter is 1.047 g/ml, which leads to water content of 0.745 and 0.165 for gray and white matter, respectively. In contrast, 0.82 and 0.73 are found by biochemical methods, indicating that there are water molecules that cannot be assessed with our method.

Recently it has been shown that 7% of the total water signal in white matter of cat brain originates from a compartment with a $T_2$ value of 13 ms (Menon et al, *Magn. Reson. Med.* 20 214, 1991). A component with a similar transverse relaxation time was also detected in the human brain. The corresponding signal was attributed to water molecules trapped between myelin layers, thus being in very slow exchange with cellular water. Attempts to detect this short $T_2$ component were made in five volunteers by adding the echo times 13, 17, and 22.5 ms to the $T_2$ measurement. A corresponding signal could not be detected in any of the volunteers, however, probably because the signal is too much attenuated even at $T_E$=13 ms. Correcting the white matter data by increasing the signal from tissue water by 7% leads to a water content that is still 7% below that determined biochemically, as shown in Table II.

TABLE II

Possible Corrections of the MRS-Determined Cerebral Water Content

|  | Gray Matter | White Matter |
| --- | --- | --- |
| $\beta_{MR}(\rho_w/\rho_b)$ | 0.745 | 0.617 |
| 13 ms component | — | 0.660 |
| Blood | 0.775 | 0.675 |
| csf/TSE | 0.798 | 0.695 |
| $\beta_{BC}$ | 0.82 | 0.73 |

The water content of blood is about 80%, which is close to that of brain tissue. Thus, if all signal from blood were assigned to the brain water compartment, the measured water content would not differ significantly from that of pure brain tissue. However, as demonstrated earlier, signal from blood is only partially assigned to brain water. Assuming a blood content in our gray and white matter voxels of at most 10 and 5%, respectively, a simple calculation shows that the water content is measured approximately 0.03 and 0.015 too low.

A further effect that might lead to a reduced water content is related to the observation that the in vivo signals from csf and the eye were repeatedly 2–3% below the hypothetical water signal $S_h$ calculated from the external standard. This might be caused by $B_1$ eddy currents. If so, all in vivo signals must be increased by 3% to be comparable with the signal from the external reference. This would in turn increase the water content by 3%.

Table II lists all these corrections. As already mentioned, the uncorrected values $\beta_{MR}(\rho_w/\rho_b)$ in gray and white matter are considerably smaller (by 0.08 and 0.11) than the biochemical water contents. This result could be explained by postulating a pool of water molecules invisible to MRS. However, if all corrections are applied, the final values are only 0.02–0.03 below those determined biochemically. This is, within the precision of the measurements, identical to unity. Thus, the concept of a pool of MRS-invisible water molecules does not have to be invoked if all corrections are valid.

Three compartments are necessary to describe basic features of the brain as observed with MRS: csf, tissue water, and an invisible rest. The knowledge of these three compartments is crucial to quantitative studies of the human brain. The differentiation between csf and tissue water is based on their significantly different $T_2$ values. The invisible compartment can be analyzed by using an external standard. The resulting reproducibility is excellent. The above described methods are universally applicable to any organ in which water compartments with distinct $T_2$ values are present.

Given the high precision of the method, several applications to various fields of MRS emerge. One in particular is the noninvasive determination of the water content of the brain where the values determined by MRS and biochemical methods are in close agreement.

The result of the $T_2$ measurement can be used to calculate an atrophy index. This atrophy index can be determined more easily than indices calculated by special postprocessing of $T_2$-weighted images.

Finally, the method has major application in quantitative in vivo spectroscopy of the human brain, where partial volume effects due to csf may play a crucial role in subjects with cortical atrophy.

EXAMPLE 2

Absolute Quantitation of Water and Metabolites in Human Brain: Metabolite Concentrations Localized cerebral $^1$HMR spectra were acquired with a stimulated-echo (STEAM) sequence as detailed in Example 1. Spectra from 22 healthy volunteers and 2 patients were used for this study. In 10 normal subjects (22–34 years old, 5 males/5 females), metabolite levels and $T_1$ relaxation were determined for two locations in the brain. The two areas were located in the posterior parietal cortex (mostly white matter) and occipital cortex (mostly gray matter), as indicated in FIG. 1B. For each voxel, one spectrum with a repetition time $T_R$ of 1.5 s (128 averages) and two spectra with $T_R$ of 5 s (64 averages each) were recorded (echo time of 30 ms and $T_M$=13.7 ms, 2048 data points, sampling period of 512 μs, obtained by digital filtering from a data set sampled at 125 kHz).

Spectra at six different echo times were acquired in a further group of 11 normal subjects. At a constant recovery time $T_r$ of 2.87 s, eight spectra were recorded with $T_E$=30 (twice), 40, 60, 90, 135, and 270 ms (twice) and 96 averages. In 5 individuals (23–30 years old, 2 males/3 females), the parietal area and in 6 others (24–33 years old, 2 males/4 females), the occipital area was investigated. In all these examinations, compartmentation of the studied voxels was determined as described in Example 1.

Model solutions were used to convert concentrations from arbitrary ("institutional") units to molar units and to determine correction factors for spectral overlap and J coupling effects. Conversion factors for singlets were obtained from eight spectra of aqueous creatinine solutions (Sigma Chemical Co., St. Louis, Mo.) of different concentrations (10.7, 21.4 and 42.5 mM).

Figure 6A:
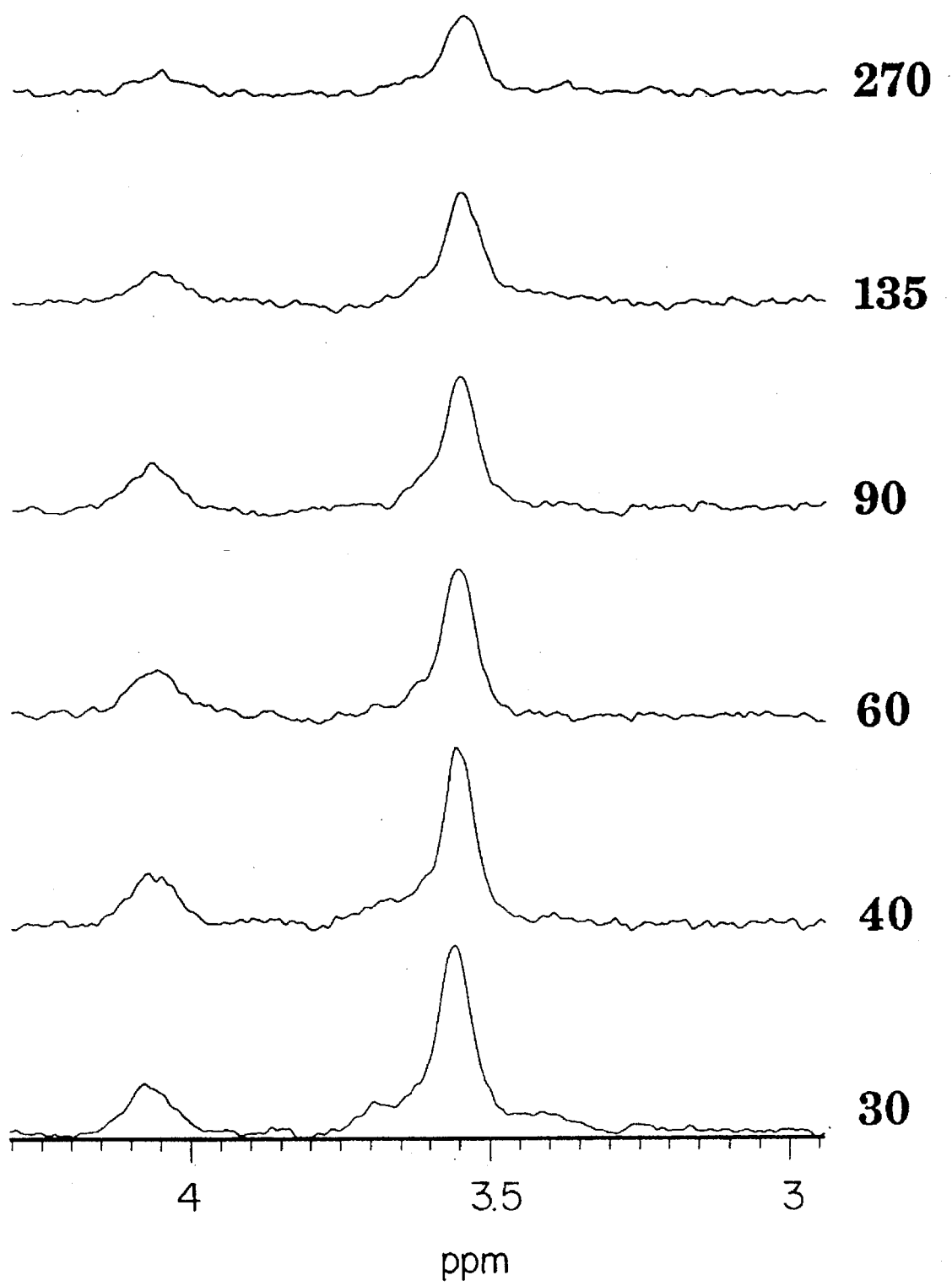
FIG. 6A illustrates experimental spectra obtained from aqueous solutions of myo-inositol.

To convert in vivo peak area measurements of myo-inositol (mI) into moles, two calibrations were performed. First, because mI features a strongly coupled, complex spectrum, the peak area measured in vivo at $T_E$=30 ms must be converted to moles of mI, using a solution spectrum of mI with known concentration. Second, the effects of J coupling on the measured peak areas in a $T_E$ series must be compensated for. Ideally, this is done with a computer simulation. However, spectra simulated with published chemical-shift values and coupling constants did not reproduce the exact spectral pattern (FIG. 6A) obtained experimentally from a solution of mI (Sigma Chemical Co., 37.3 mM, pH 7.17) and N-acetylaspartate (NAA) (the NAA peak is not shown) (Sigma Chemical Co., 27.5 mM). Thus, correction factors for J coupling were determined from the experimental spectra. If no such correction had been applied, the modulation due to J coupling would have been misinterpreted as transverse relaxation. An apparent $T_2$ of 160 ms resulted from fitting the peak areas of the simulated spectra to a monoexponential decay.

Figure 6B:
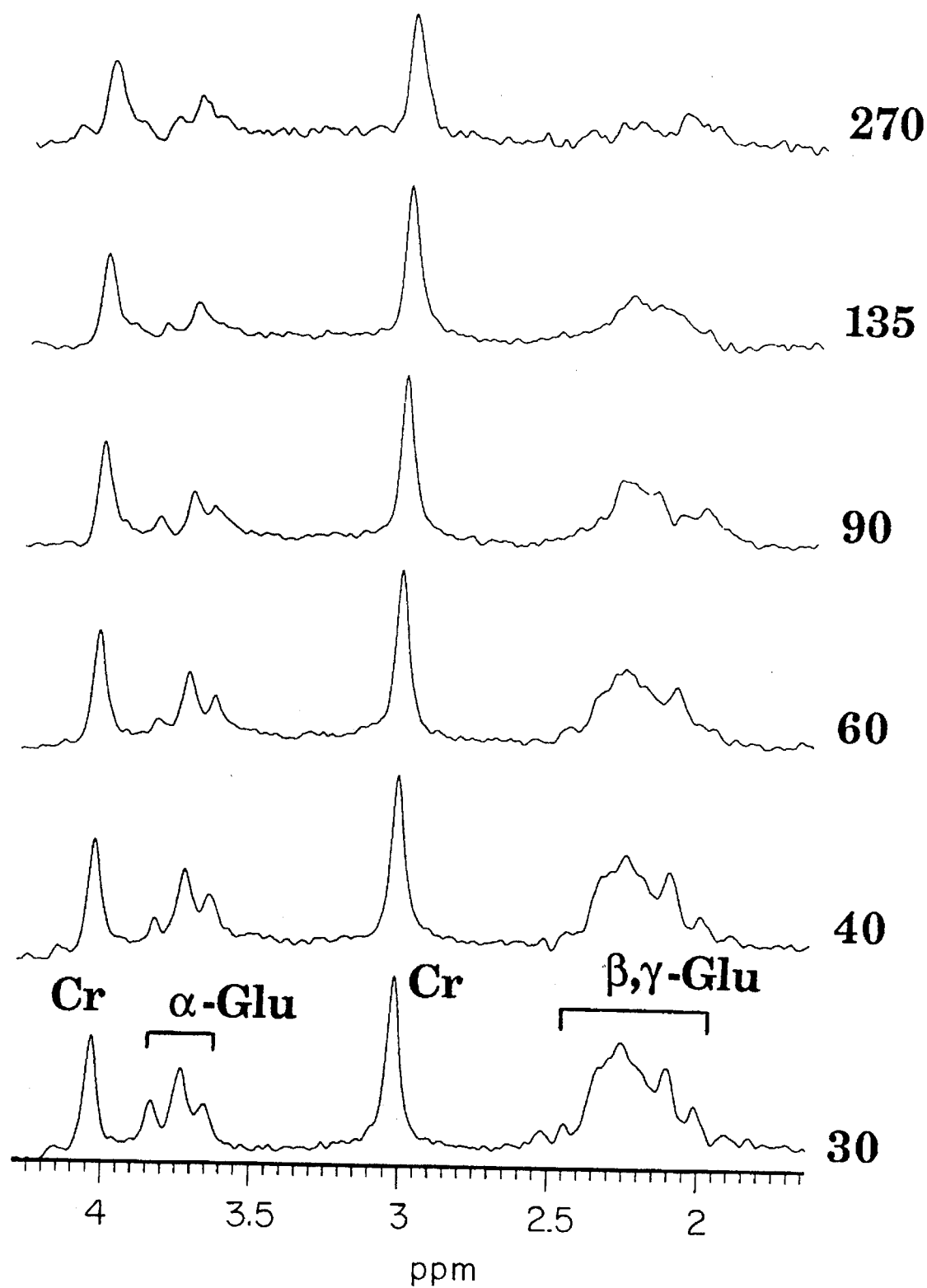
FIG. 6B illustrates experimental spectra obtained from aqueous solutions of glutamate and creatinine.

A further correction is needed for the well-known overlap between the signal from the methyl protons of N-acetyl groups (e.g., NAA) and the signal from the strongly coupled β and γ protons of glutamate, neglecting minor contributions from glutamine. For this purpose, phantom spectra with the same echo times as above were recorded from an aqueous solution of glutamate (51.2 mM, No. G-1626, Sigma Chemical Co.), creatinine (14.7 mM), and lactate (pH 7.15), (the lactate peak is not shown), FIG. 6B. Arithmetically summed spectra of glutamate and NAA yielded correction factors for NAA peak areas at all echo times.

To derive molar concentrations for the main peaks of the in vivo $^1$H-MR spectra, four different data-processing schemes were compared. These methods differ in the baseline corrections used (step 3) and in the determination of peak areas (step 4). Steps 1–2 and 5–7 are identical for all schemes.

1. Low-frequency filter. The residual water signal was suppressed by digital low-frequency filtering. This step eliminates most of the slanting baseline caused by a water peak that was not sufficiently suppressed during the acquisition. The particular scheme in use works best if the residual water peak is not inverted with respect to the metabolite signals.

2. Fourier transformation. The FIDs were apodized (0.5 Hz Gaussian line broadening), zero-filled to 8192 points, and Fourier transformed, followed by manual zero-order phase correction.

3. Baseline correction. Two alternative baseline corrections were applied. A frequency-independent (DC) baseline was used, calculated from data points between either −3.8 and 0 ppm (scheme 0) or 2.65 and 2.75 ppm (scheme M).

4. Determination of peak areas. Peak areas were determined using two different methods. In method I, a simple integration over 0.18 ppm (0.12 ppm for mI) was performed for each peak. For the average linewidth observed, 8% of the choline (Ch) integral must be subtracted from the creatinine (Cr) value (and vice versa) to correct for mutual overlap. In method L, a Lorentzian line was fitted to each resonance, using 0.18 ppm of data points. The Cr and Ch peaks were fitted simultaneously. Fitting Gaussian lines consistently produced higher $\chi^2$ values.

5. Correction for compartmentation. The fractions of csf, brain water, and invisible rest were determined as described in Example 1 and used to calculate concentrations in various units.

6. Correction for $T_2$ and underlying baseline. To determine transverse relaxation times of the main metabolites, the dependence of peak areas on echo time was measured in 11 volunteers. Because the signal decay of none of the metabolites was well represented by a monoexponential function, double-exponential functions were used for fitting. The long $T_2$ component was interpreted to arise from the desired metabolite. The decay time of the fast-decaying component was restricted to values <30 ms. The average ratio between the observed signal at $T_E$=30 ms and the starting amplitude of the long component was used as a correction factor for the determination of millimolar concentrations.

7. Correction for $T_1$ saturation. Saturation factors were obtained from scans with different $T_1$ according to Equation [1].

Step 6 is vital for determining molar concentrations. It can be omitted, however, when results are to be expressed in institutional units, used to detect absolute spectral changes.

The reproducibility of the suggested scheme was established by examining the variations in the creatine concentration per wet weight ($c_{bm}$) in gray matter (two spectra in each of 10 volunteers). The means differences between repeated scans in the same individual (3–6% for various processing methods) were almost identical to the relative standard deviations (RSD) of all 20 measurements (4–6%). This hints at the fact that spectral noise or fluctuations due to the processing method (spectral phasing in particular), rather than interindividual variations, were the factors determining reproducibility. No significant reproducibility differences were observed in comparing direct integration (I) with Lorentz fitting (L), whereas the RSDs for baseline correction below 0 ppm (0) tended to be lower than those for the correction at 2.7 ppm (M).

Figure 7:
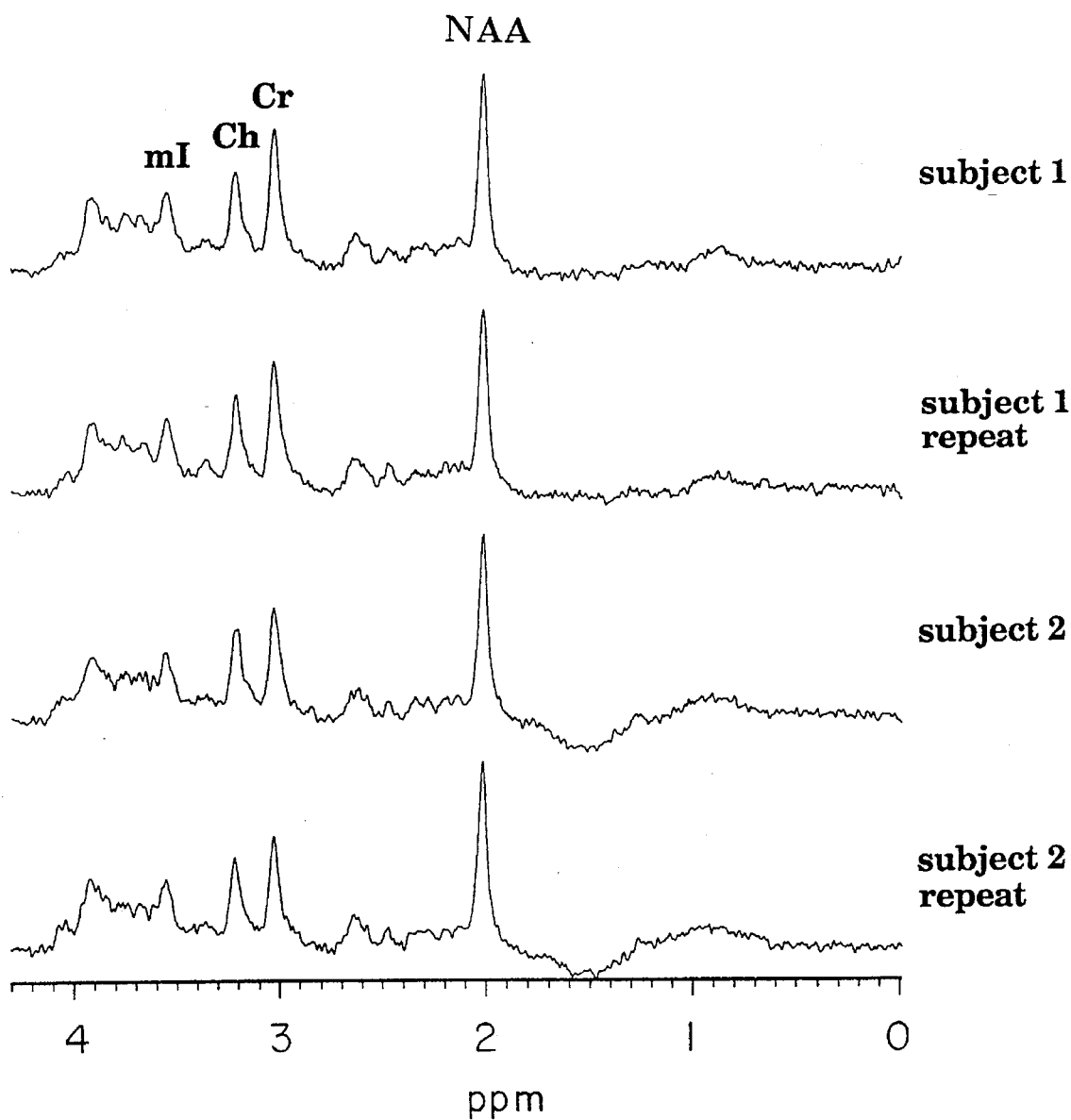
FIG. 7 illustrates STEAM-localized $^1$H spectra obtained from two different subjects.

The standard error of the means was close to 1% for all methods. A similar precision was obtained for the mixed parietal region FIG. 7. Much larger errors emerged when the baseline was arbitrarily defined on either side of each of the major peaks.

As will be seen below, this accuracy, limited by statistical variations, is lost when absolute numbers in moles are determined. Systematic errors then considerably increase the uncertainty of the measured values.

To calculate absolute concentrations from single spectra at $T_E$=30 ms, one not only must know longitudinal and transverse relaxation times of all metabolites considered, but also how to correct for underlying broad or J-coupled spectral components. The presence of such fast-decaying components is obvious from FIG. 8, in which Cr peak areas obtained from the white matter location in one normal subject are plotted as a function of echo time.

Several different curves are fitted to the data. A monoexponential decay represents the observed data very poorly, in contrast to a double-exponential decay. The slower decreasing part of the double-exponential decay was interpreted to originate from the metabolite itself. The resulting $T_2$ values are given in Table III. The fast exponential was attributed to background and was thus used to determine the underlying baseline. There are not enough data points close to time zero to define the exact nature of this component. The possibility that it originates in part from the same metabolite in a different environment cannot be ruled out.

Figure 8:
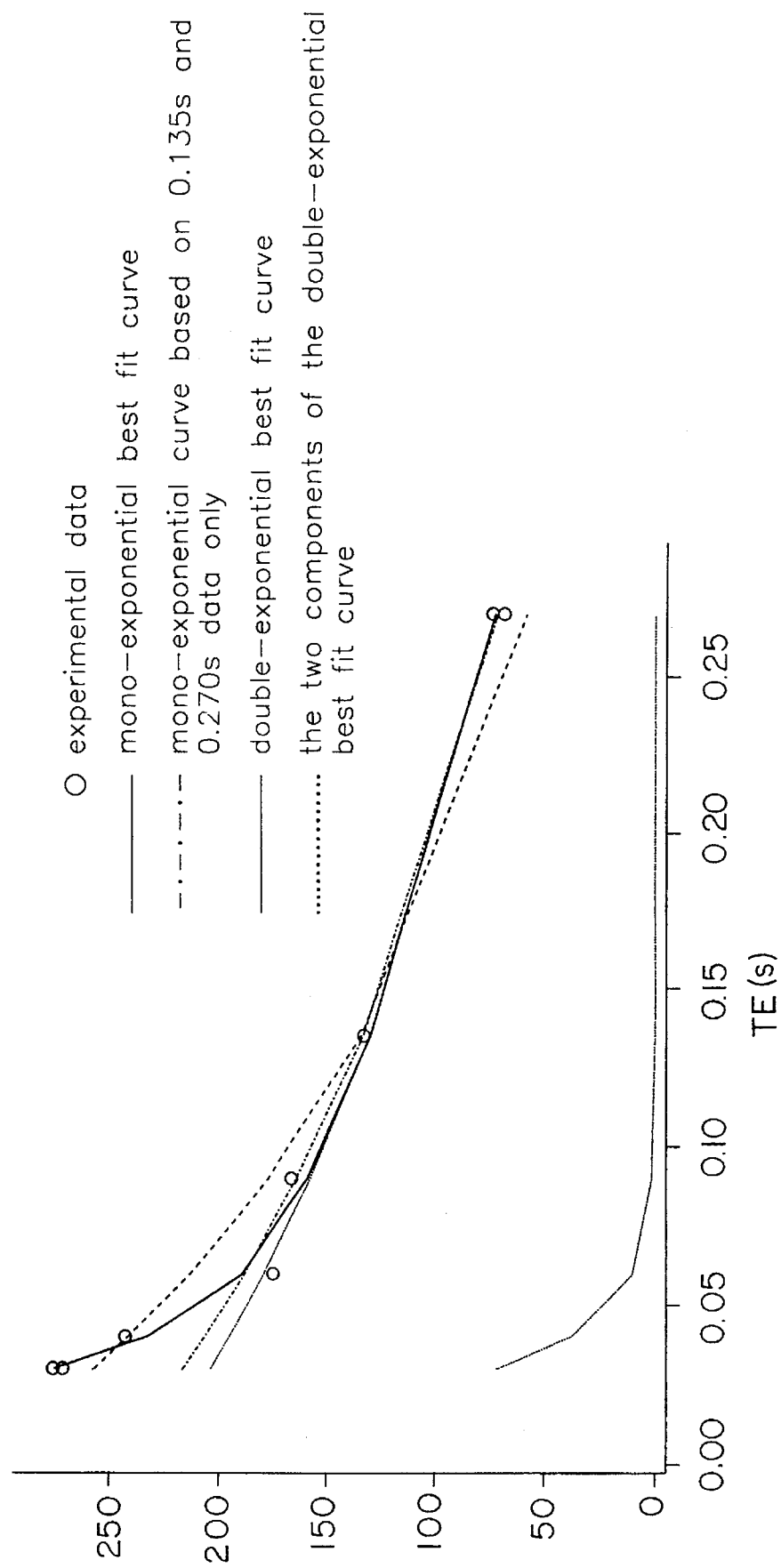
FIG. 8 illustrates signal decay of the creatine peak area as a function of echo time.

The third curve included in FIG. 8 uses only the data points at $T_E$=135 and 270 ms to define a monoexponential decay. Apart from a larger scatter in the results, this approach yielded values similar to the slow decay curve in the double-exponential fit. The correction factors C relating the area measurement at $T_E$=30 ms to the starting amplitude $I_0$ of the slower-decaying component of the double-exponential decay vary between 0.69 and 1.01 depending on metabolite, location, and processing scheme. As an example, the correction factors obtained for method ML in white matter are listed (mean ±1 SD): 0.87±0.07 (NAA), 0.89±0.09 (Cr), 0.86±0.06 (Ch), 0.82±0.08 (mI).

The measured linewidths for the major peaks varied between 3.1 and 4.1 Hz (NAA, Cr, Ch) and 4.5 and 6 Hz (mI) in gray and white matter, with a standard error of 15–25% (method ML). The residual linewidth $T_2^+$ (after subtraction of the natural linewidth) of the sharpest metabolite peak was about 2 Hz. This is not surprising because shimming was performed on brain water with a natural linewidth of 4 Hz. No conclusion about multiple components of individual peaks can therefore be drawn from the linewidths.

To determine the longitudinal relaxation of the metabolites, two sets of data at repetition times $T_R$ of 1.5 and 5 s and fixed $T_E$ of 30 ms were acquired. Using the amplitudes of the individual peaks in the two measurements, the $T_1$ values can then easily be calculated (Table IV). The values determined with processing scheme M slightly exceed those with scheme 0.

TABLE IV

Longitudinal Relaxation Times $T_1$ (s) Obtained from Saturation Factors in Experiments with $T_R$ = 1.5 and 5 s

| bc | A | NAA | Cr | Ch | mI |
|---|---|---|---|---|---|
| | | | White | | |
| 0 | I | 1.29 ± 0.05 | 1.22 ± 0.02 | 1.22 ± 0.03 | 1.10 ± 0.03 |
| 0 | L | 1.22 ± 0.07 | 1.05 ± 0.04 | 1.30 ± 0.04 | 1.00 ± 0.05 |
| M | I | 1.41 ± 0.07 | 1.36 ± 0.05 | 1.40 ± 0.08 | 1.21 ± 0.04 |
| M | L | 1.34 ± 0.09 | 1.24 ± 0.05 | 1.48 ± 0.09 | 1.19 ± 0.08 |
| | | | Gray | | |
| 0 | I | 1.31 ± 0.09 | 1.26 ± 0.03 | 1.26 ± 0.03 | 1.11 ± 0.03 |
| 0 | L | 1.17 ± 0.11 | 1.15 ± 0.06 | 1.06 ± 0.06 | 1.02 ± 0.07 |
| M | I | 1.37 ± 0.07 | 1.34 ± 0.06 | 1.08 ± 0.08 | 1.16 ± 0.09 |
| M | L | 1.29 ± 0.08 | 1.29 ± 0.06 | 1.12 ± 0.12 | 1.10 ± 0.16 |

The concentrations $c_{bm}$ Corresponding to biochemical wet-weight concentrations were calculated with each of the four processing schemes, using baseline conversion factors and $T_1$ values discussed above (Table V).

TABLE III $T_2$ Values (s) Determined from Five (Mixed Parietal Voxel) and Six Normal Subjects (Occipital Gray Matter), Respectively, Calculated with Four Different Processing Schemes (Mean Values ± SD)

| bc | A | NAA | Cr | Ch | mI |
|---|---|---|---|---|---|
| | | | White (n = 5) | | |
| 0 | I | 0.462 ± 0.054 | 0.208 ± 0.012 | 0.323 ± 0.04 | 0.200 ± 0.052 |
| 0 | L | 0.436 ± 0.086 | 0.194 ± 0.032 | 0.298 ± 0.067 (n = 4) | 0.195 ± 0.077 |
| M | I | 0.519 ± 0.005 | 0.218 ± 0.016 | 0.337 ± 0.010 | 0.198 ± 0.043 |
| M | L | 0.515 ± 0.051 | 0.214 ± 0.017 | 0.340 ± 0.019 | 0.195 ± 0.047 |
| | | | Gray (n = 6) | | |
| 0 | I | 0.39 ± 0.042 | 0.206 ± 0.032 | 0.372 ± 0.123 | 0.25 ± 0.024 |
| 0 | L | 0.393 ± 0.063 | 0.198 ± 0.025 | 0.448 ± 0.169 (n = 4) | 0.280 ± 0.057 |
| M | I | 0.426 ± 0.043 | 0.204 ± 0.011 | 0.363 ± 0.068 | 0.317 ± 0.101 |
| M | L | 0.388 ± 0.026 | 0.207 ± 0.010 | 0.395 ± 0.073 | 0.314 ± 0.110 |

Figure 9:
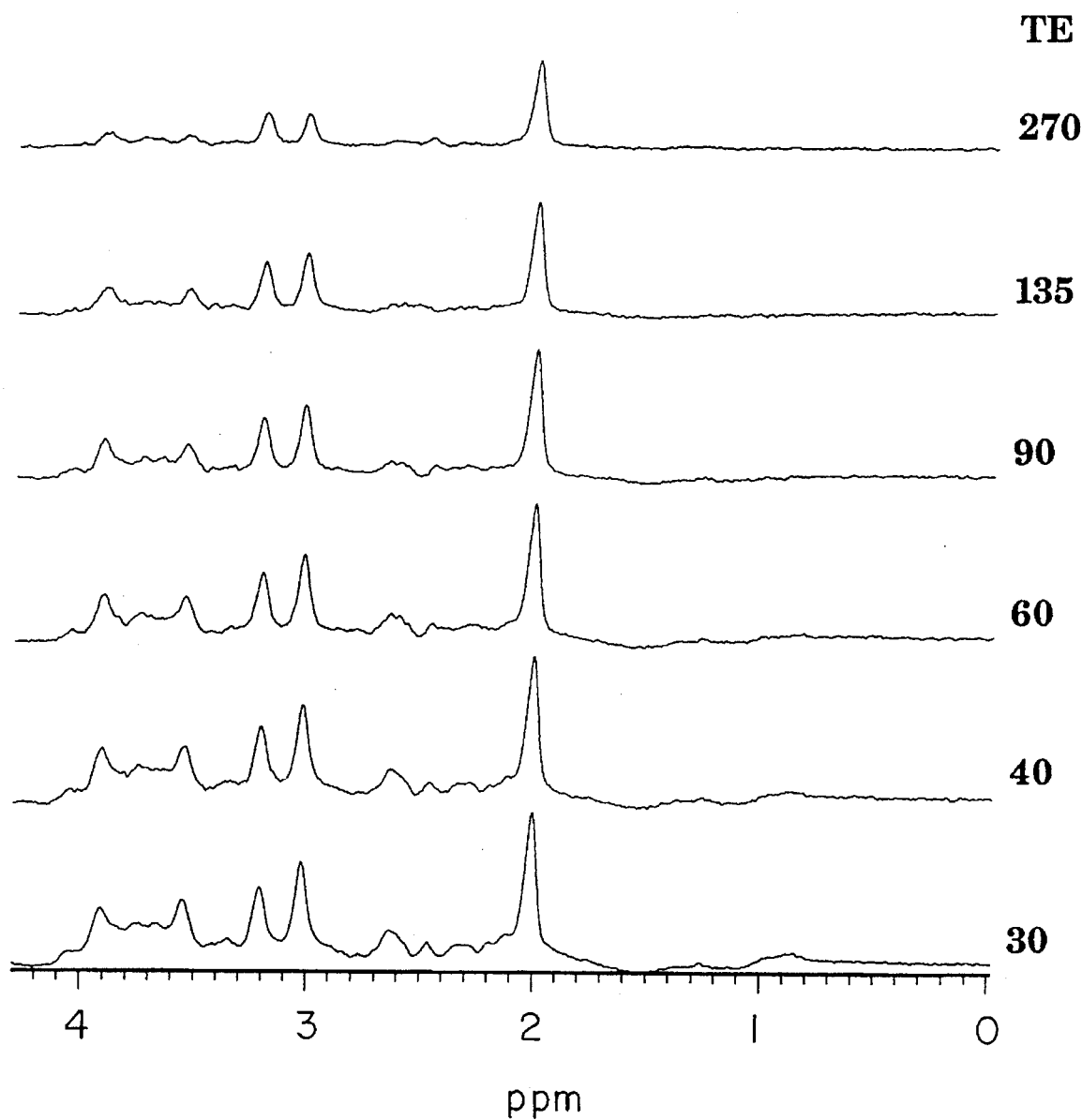
FIG. 9 illustrates in vivo $^1$H spectra from parietal white matter as a function of echo time.

The changes occurring in human cerebral proton spectra as a function of echo time are illustrated in FIG. 9. Summed spectra with echo times of 30, 40, 60, 90, 135, and 270 ms are displayed.

TABLE V

"Wet Weight" Concentrations ($c_{bm}$) Obtained Using Four Different Data-Processing Schemes

| bc | A | NAA | Cr | Ch | mI |
|---|---|---|---|---|---|
| 0 | I | 10.0 ± 0.13 | 8.95 ± 0.08 | 1.65 ± 0.04 | 7.77 ± 0.21 |
| 0 | L | 9.02 ± 0.14 | 7.87 ± 0.08 | 1.32 ± 0.04 | 8.46 ± 0.32 |
| M | I | 9.06 ± 0.12 | 7.95 ± 0.11 | 1.41 ± 0.05 | 6.24 ± 0.21 |
| M | L | 8.89 ± 0.13 | 7.49 ± 0.11 | 1.32 ± 0.05 | 6.56 ± 0.29 |

Note:
Results for the gray matter location were obtained from 10 normal subjects, with three spectra from each individual. The indicated standard errors of the mean correspond to random variations within the 20 measurements (treated as independent; standard errors if only mean values for each subject are used are 10 to 50% higher than those listed below) recorded with $T_R$ of 5 s for each location. Systematic errors are not included.

Based on the compartmentation model of I, other concentration units can be determined as indicated above. Table VI contains a list of conversion factors to transform wet weight concentrations to all other units using typical voxel compositions and tissue water contents. These numbers indicate the differences between the various concentration measures in use.

TABLE VI

Comparison of Different Concentration Units, Based on in Vivo Measurement of Compartment Sizes and Water Contents

| Conversion Factors | $\beta_{MR}$ | $s_{csf}$ | $c_{tv}$[a] | $c_{bm}$ | $c_{bv}$ | $c_{wm}$[b] | $c_{dw}$ |
|---|---|---|---|---|---|---|---|
| Normal mixed parietal | 0.69 | 0.037 | 1.011 | 1 | 1.05 | 1.522 | 2.917 |
| Normal gray occipital | 0.78 | 0.075 | 0.971 | 1 | 1.05 | 1.346 | 3.889 |
| Newborn (typical) | 0.90 | 0.037 | 1.011 | 1 | 1.02 | 1.133 | 8.5 |
| Atrophy gray matter | 0.78 | 0.25 | 0.788 | 1 | 1.05 | 1.346 | 3.889 |

[a] $c_{tm}$ is proportional to $c_{tv}$ with the average density within the selected voxel as proportionality constant.
[b] $c_{wv}$ is numerically equal to $c_{wm}$, although the units are different.

Figure 10:
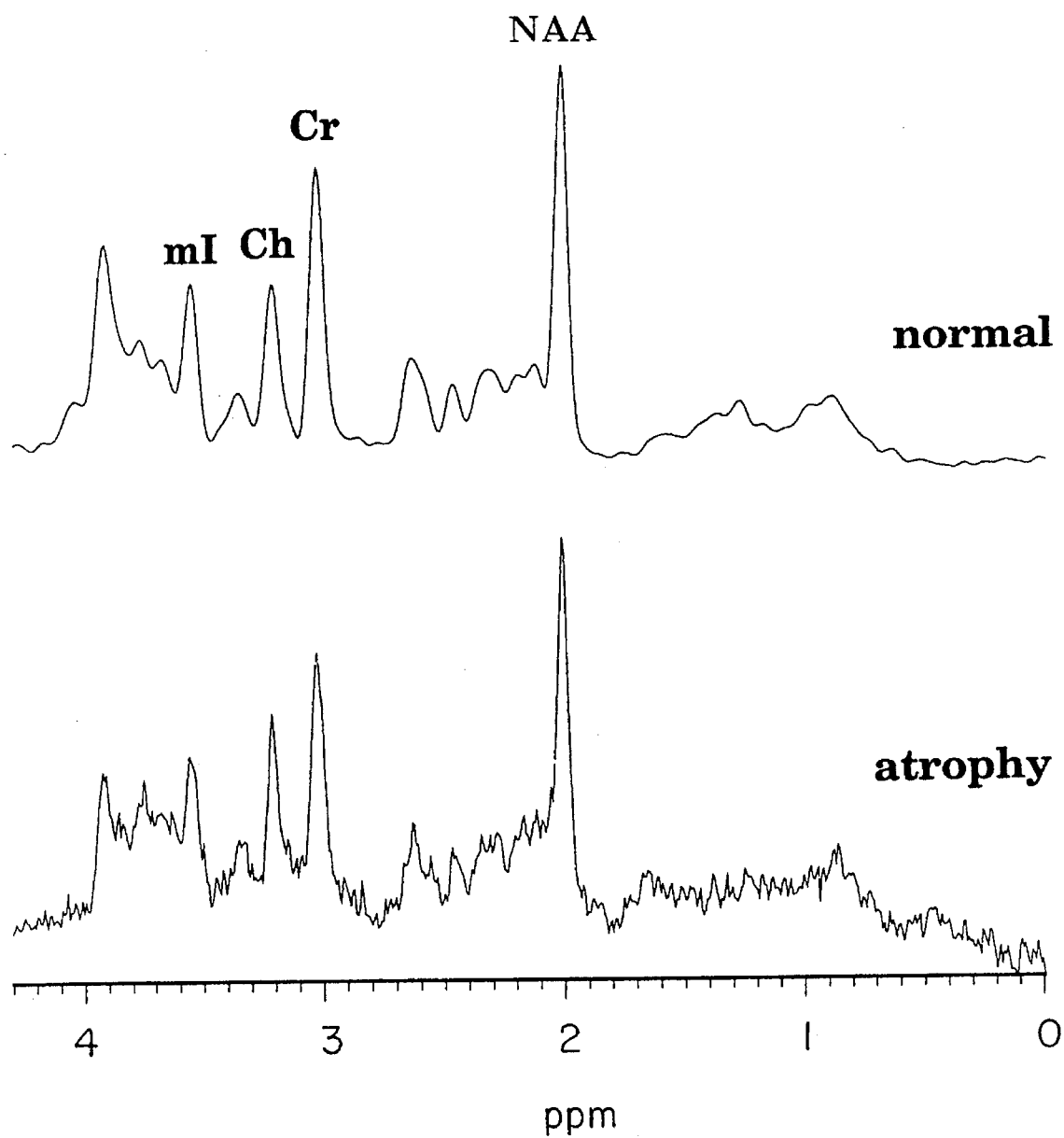
FIG. 10 illustrates localized $^1$H spectra from occipital cortex in a healthy 51-year old man (bottom) and an average spectrum from a control group of 10 normal volunteers of age 22 to 34 (top)

Finally two examples are given, illustrating the clinical relevance of absolute quantitation. The first example is cortical atrophy, which can be age-related or caused by any of several pathologies. The spectra presented in FIG. 10 were acquired from a 51-year-old man without any known neurologic disease. The bottom spectrum in FIG. 10 appears normal in terms of peak ratios when compared to the summed gray matter spectrum of the control group in the top spectrum. The csf content in the older subject is 23% as opposed to an average of 7.5% in the control group. The water content of the brain tissue was not significantly different from that of the control group (0.76 vs 0.78).

The question in this case, as in most other clinical examinations, is whether the metabolite levels in the remaining brain tissue are identical to those in normal volunteers. This obviously does not require expression of concentrations in molar units; institutional units are equally appropriate. The most convenient solution is to express patient concentrations in units of normal values. For the 51-year-old subject with atrophy, this leads to the following relative wet weight concentrations, $c_{bm}^{rel}$:

NAA=1.01±0.02; Cr=1.03±0.02; Ch=1.22±0.04; mI=1.12±0.04.

This indicates that the NAA and Cr concentration in the residual brain tissue are unchanged, whereas the Ch and possibly the mI levels are increased. In contrast, calculating concentrations with respect to the total volume ($c_{tv}$) and thus neglecting the large csf content yield NAA=0.84±0.01; Cr=0.86±0.02; Ch=1.01±0.04; mI=0.94±0.04.

The concentrations of NAA, Cr, and possibly mI would have been misinterpreted as reduced compared to normals, whereas the choline level would appear to be unchanged. This example applies equally to subjects in whom the VOI overlaps some portion of the ventricle.

Figure 11:
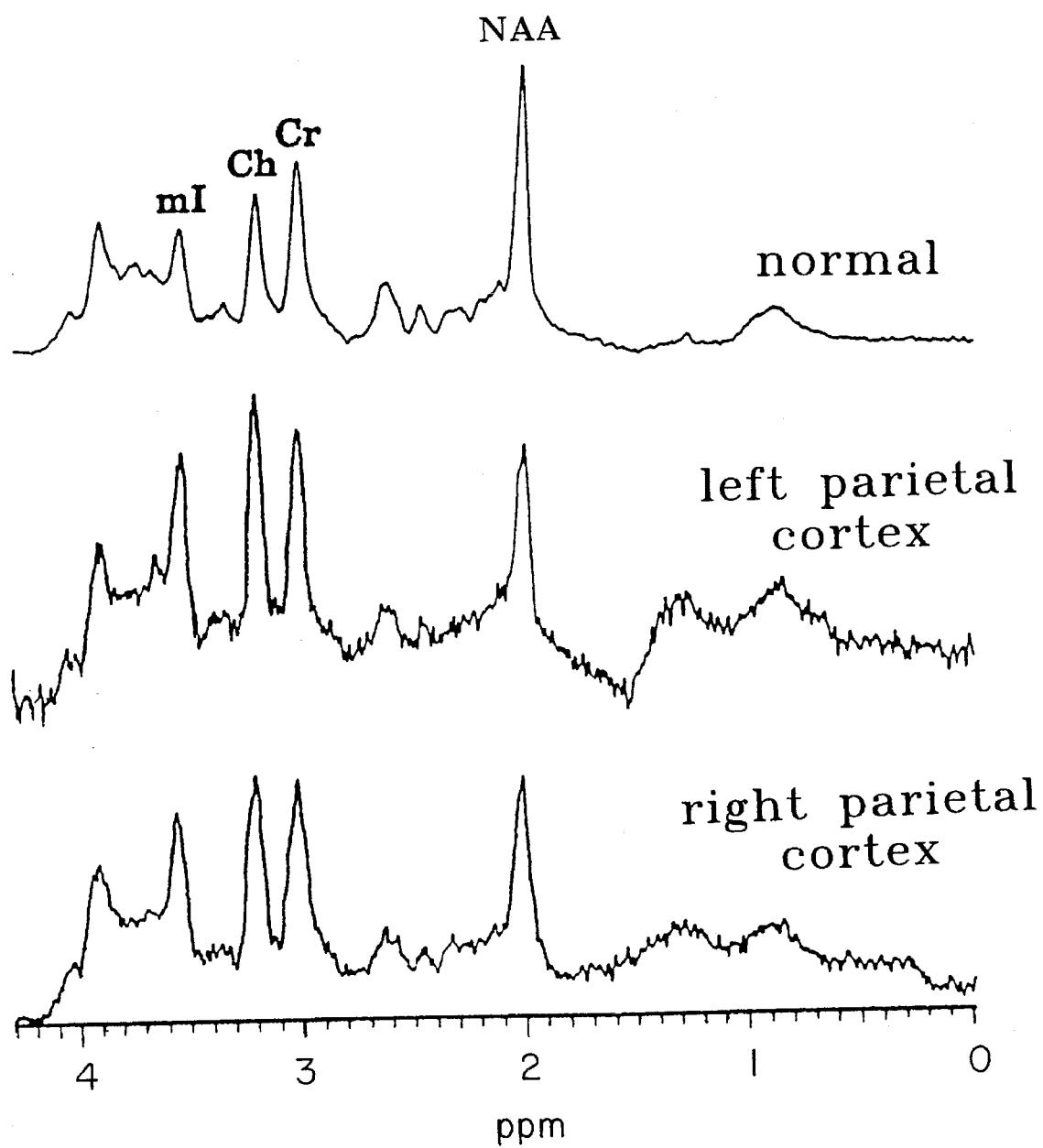
FIG. 11 illustrates $^1$H-MR spectra from the left (middle) and the right (bottom) parietal cortex of a patient suffering from head trauma in a coma for three months. The top trace shows the sum of ten spectra from the parietal cortex of 10 healthy subjects, acquired under identical experimental conditions.

While in the case of atrophy the spectra pattern looked fairly normal, and with a lucky guess, the right internal reference might have been chosen to conclude absolute information from peak ratios, this is not possible here (cf. FIG. 11). This spectrum was recorded from a 28-year-old woman, comatose after head trauma. The spectral pattern is grossly abnormal and "ratios" cannot be used for its interpretation. Using the proposed scheme for absolute quantitation, the metabolite levels in the left parietal cortex (middle spectrum in FIG. 11) compared to the same location in the control group as follows ($c_{bm}^{rel}$);

NAA=0.88±0.02; Cr=1.19±0.01; Ch=1.75±0.04; mI=1.59±0.06

Contrary to expectations, all of the major metabolites were increased, while NAA was only modestly reduced.

The proposed methods for determining absolute metabolite levels in vivo are very reproducible with relative standard deviations in single spectra of 4–6% for the creatine peak (Table V). Longer data acquisitions or, better still, repeated acquisitions may further reduce the uncertainties.

The choice of the data-processing scheme introduces larger uncertainties than the random errors of data acquisition and processing. These increased differences are caused by systematic errors, such as baseline effects and spectral overlap. This means that it is much more difficult to obtain a concentration measure that is comparable to values measured with non-MRS methods than to unequivocally determine whether a certain peak in a spectrum is changed compared with a control group, or a previous measurement. Fortunately, the latter is all that is needed for many clinical purposes.

The major obstacle in determining absolute concentrations from $^1$H-MR spectra is the unclear baseline. In spectra acquired at an echo time ≦100 ms, none of the metabolite peaks stands by itself on a zero baseline. As seen from FIG. 10, it is not sufficient to set an area in the spectrum to zero that looks like "baseline." Monoexponential decay with echo time was not found for any of the four major peaks. Extrapolating back from the 30 ms spectrum to time zero would therefore overestimate the metabolite concentration by 20 to 40%.

None of the four proposed schemes for calculating peak areas is superior to the others. Using a baseline correction at 2.7 ppm is better for eliminating errors due to general baseline shifts, such as from a strong residual water signal; a baseline correction below 0 ppm is not susceptible to unexpected metabolite resonances due to pathology. It is, however, essential to correct for a constant baseline offset in some way, because the spectral baseline depends on the first point of the FID, which in turn depends substantially on the residual water signal.

Peak area determination by fitting a Lorentzian is quite accurate, even if the linewidths are different from those of the control group, but readily overestimates areas if peaks are small and overlap with other resonances. This is a less serious problem if direct peak integrations are used. To give a best estimate of true in vivo concentrations, Table VII therefore contains the averages obtained with all four schemes. The averaged transverse and longitudinal relaxation times are also included.

TABLE VII

Averages of Concentrations and Relaxation Times for Gray and White Matter Locations, Given as Mean Values ± SE
(SE with Regard to the Four Processing Schemes, Except for $T_1$ where Only Scheme M Was Used)

|  | Unit | NAA | Cr | Ch | mI |
|---|---|---|---|---|---|
|  |  | White |  |  |  |
| $c_{bm}$ | mmol/kg tissue | 8.81 ± 0.18 | 6.33 ± 0.14 | 1.58 ± 0.02 | 6.68 ± 0.44 |
| $c_{wm}$ | mmolal | 13.59 ± 0.27 | 9.75 ± 0.22 | 2.43 ± 0.02 | 10.29 ± 0.67 |
| $T_1$ | s | 1.38 ± 0.05 | 1.30 ± 0.06 | 1.44 ± 0.04 | 1.20 ± 0.01 |
| $T_2$ | s | 0.483 ± 0.020 | 0.209 ± 0.005 | 0.325 ± 0.010 | 0.197 ± 0.011 |
|  |  | Gray |  |  |  |
| $c_{bm}$ | mmol/kg tissue | 9.24 ± 0.26 | 8.04 ± 0.32 | 1.43 ± 0.08 | 7.26 ± 0.52 |
| $c_{wm}$ | mmolal | 12.68 ± 0.35 | 11.06 ± 0.43 | 1.95 ± 0.11 | 9.93 ± 0.71 |
| $T_1$ | s | 1.33 ± 0.04 | 1.32 ± 0.03 | 1.39 ± 0.01 | 1.13 ± 0.03 |
| $T_2$ | s | 0.399 ± 0.009 | 0.204 ± 0.002 | 0.401 ± 0.020 | 0.279 ± 0.014 |

Figure 12:
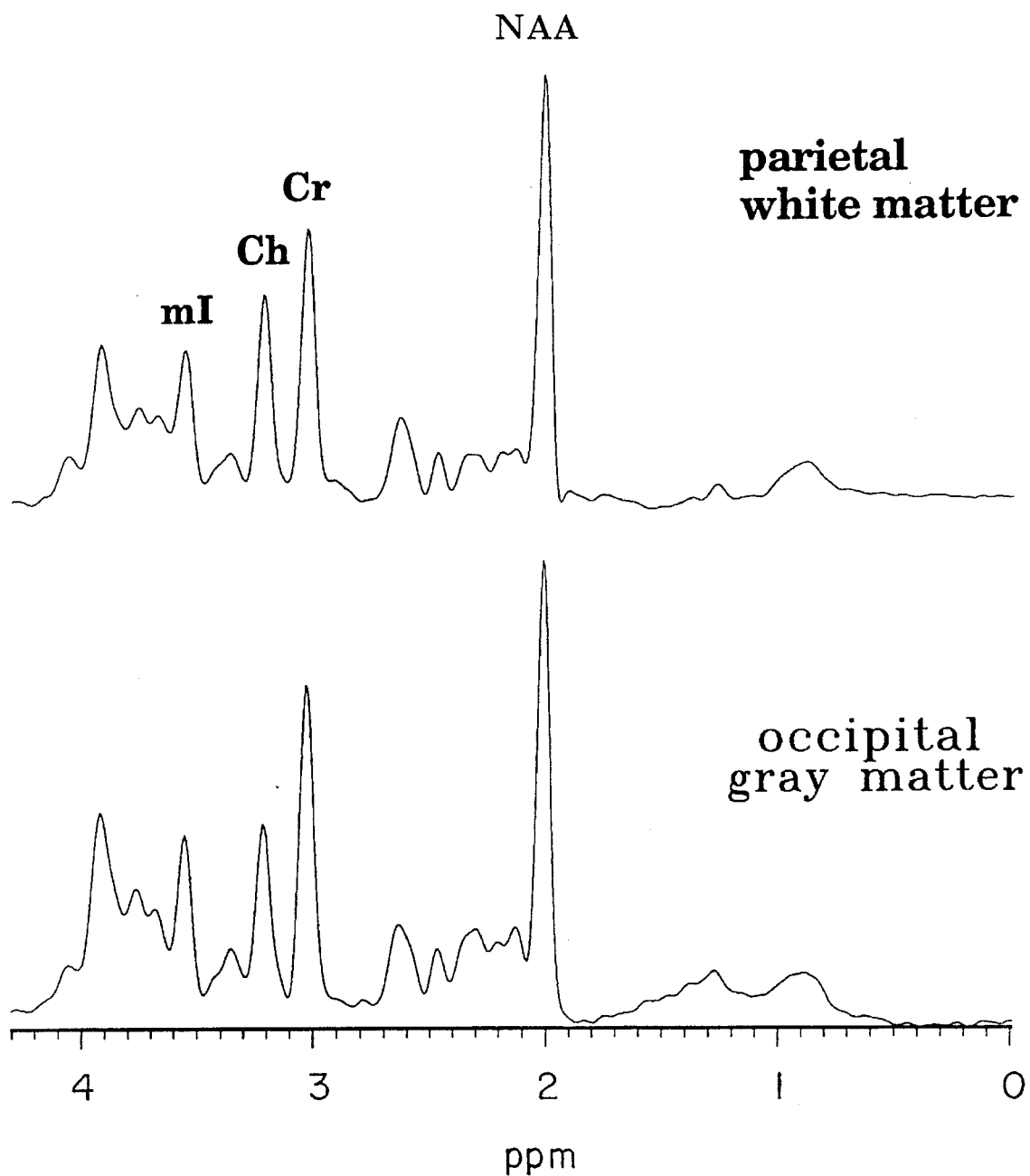
FIG. 12 illustrates an average spectrum from parietal, mostly white cortex (top) compared with spectrum from occipital, gray matter cortex (bottom)

Table VII and FIG. 12 can be used to compare the composition of the two areas investigated in this study. The two main differences in terms of peak ratios between gray and white matter spectra are the NAA/Cr and Ch/Cr ratios, both of which are higher in the mostly white matter location of the parietal cortex. There is 25% more creatine per brain tissue mass in gray than in white matter. The regional differences in the NAA and choline peaks are, although significant, much smaller. Comparing molal concentrations essentially corrects for differences in myelin content. The white-gray difference is then less marked for Cr and even reversed for NAA.

$T_1$ relaxation times for white and gray matter are almost exactly identical. The differences between individual metabolites are rather small, with the methyl protons of the choline groups relaxing slowest. In contrast to this, there are substantial differences in the transverse relaxation rates between white and gray matter, as well as between the metabolites. The N-acetyl groups relax significantly faster in gray than in white matter, whereas the opposite holds for the choline and inositol protons.

Barker et al. (Abstract of the Society of Magnetic Resonance in Medicine, 10th Annual Meeting, Vol. 1, p 381, 1991) list values of 15.4 μmol/g NAA, 11.8 μmol/g Cr, and 2.6 μmol/g Ch for a frontal white matter voxel (expressed as moles per mass of brain tissue), with statistical errors of about 20%. The fact that these values are 1.65–1.85 times higher than the values obtained herein can be readily explained by the following: First, Barker et al. assume a water content of 0.8 compared to our measured 0.65–0.7 (Table II, Example 1). Second, a monoexponential $T_2$ decay was used without further baseline correction. With these two corrections, the resulting metabolite concentrations are within 10% of the values in Table VII.

The numbers given by Michaelis et al. (Abstract of the Society of Magnetic Resonance in Medicine, 10th Annual Meeting Vol. 1, p 387, 1991) and Hennig et al. (Abstract of the Society of Magnetic Resonance in Medicine, 10th Annual Meeting, Work in Progress, p 1013, 1991) are similar to each other and generally 10–15% below the values reported herein. Michaelis et al. did not correct for csf, and for peak area determination they used an integration after setting arbitrary points on either side of each peak to zero (personal communication). From the previous discussion of baseline effects, such an approach is not recommended and is anticipated to lead to lower concentrations and increased statistical variations. The inclusion of the csf correction would further increase their values by 5%.

The lower values reported by Hennig et al. might result from the fact that their fits were performed with Gaussian lines. Their unique approach to use only spectra with $T_E$=135 and 270 ms alleviates baseline effects but may be the reason why, with standard deviations of 25–45%, the paper does not accomplish the reproducibility of the other studies. Parts of the above discrepancies might be due to the choice of different locations in the brain as well.

N-acetyl moieties.

NAA in the cerebral proton spectrum is largely N-acetylaspartate, a compound of great interest as a probable neuronal marker. Tallan (*J. Biol. Chem.* 224 41, 1957) determined NAA in rat brain as 5.5 mM. Petroff et al. (*Neurology* 39, 1187, 1989) found 5.87 mmol/kg frozen wet weight of human frontal cortex and Burri et al., (*Neurochem. Res.* 15 1009, 1990) working with frozen rat brain, determined 7–8 mmol/kg. Our values for human cortex exceed these estimates by 20–30%. In addition to possible errors in our method, there are three further reasons for this discrepancy. First, there are further compounds contributing to the NAA peak; second, a labile pool of NAA may be lost during tissue fixation and extraction; and third, because of adherent water, concentration values obtained from frozen samples are often underestimated by up to 15%.

Creatine.

The creatine peak is composed largely of creatine and phosphocreatine and controlled by the creatine phosphokinase equilibrium. In Veech et al. (*J. Biol. Chem.* 254 6538, 1979), the total concentration of Cr plus PCr, obtained using enzymatic analysis of freeze-blown rat brain, is given as 10.8 mM, translating into 8.6 mmol/kg tissue for the assumed water content of 80%. Petroff et al. found values for white and "gray" matter of 7.68 and 9.63 mmol/kg frozen wet weight of postoperative human brain and Burri et al. 9.56 mmol/kg wet weight of rat brain.

The values obtained in the present study, 6.33 mmol/kg brain for parietal white matter and 8.04 mmol/kg for occipital gray matter, give an "average" value of 7.2 mmol/kg human brain, which differs by only 16% from that obtained by Veech et al. in the rat. This difference may be species-related.

Choline.

The choline peak is most complex, with phosphocholine, glycerophosphorylcholine, and free choline and the additional possibility that the head groups of phosphatidylcholine, which is a major component of myelin, are partially or totally MRS-visible. Furthermore, a number of other compounds, including betaine and carnitine, overlap with the resonance of choline in in vivo human cerebral spectra. Miller (*NMR Biomed.* 4 47, 1991) reports that phosphorylcholine, glycerophosphorylcholine, plus free choline in human brain extracts, assayed by gas chromatography-mass spectrometry, is 1.6 mmol/kg wet weight. The proximity of the result presented herein (1.6 mmol/kg wet weight in white and 1.4 mmol/kg in gray matter) to that determined by Miller is striking, indicating that phosphatidylcholine head groups are not MRS-visible to any great extent under experimental conditions feasible for in vivo MRS.

myo-Inositol.

myo-Inositol is a six-carbon polyol related to glucose and inositol polyphosphate messenger metabolism. The peak area of the main resonance attributed to mI includes contributions from inositol 1-phosphate and the amino acids glycine (singlet at 3.56 ppm) and glutamate (triplet at 3.75 ppm). A single postmortem human brain assayed by Wells et al. (*J. Biol. Chem.* 240 1002, 1965) contained 5.5 mmol/kg wet weight of mi. The rat brain content is between 7 and 9 mmol/kg wet weight. For human brain, Petroff et al. report values between 5.8 and 9.5 mmol/kg frozen wet weight and, in the same samples, glycine concentrations of approximately 0.5 mmol/kg. The values found in our present study were 6.7 and 7.3 mmol/kg, effectively identical for gray and white matter.

Presented herein is a method of data acquisition and spectral processing which provides a quantitative measurement of key metabolites in the human brain using in vivo $^1$H-MRS. As described in Example 1, the proposed scheme provides information about the compartmentation of a selected region of brain tissue in terms of tissue water, cerebrospinal fluid, and residual constituents. As practical quantities, the water content of brain tissue and an easily determined atrophy index emerged.

The compartmentation model was used to define and interconvert different metabolite concentration units used in the literature. The cerebral concentrations of four major metabolites as well as the longitudinal and transverse relaxation times of the corresponding protons were determined, using different schemes for data processing. The compartmentation model as well as an analysis of the differing postprocessing schemes provided insight into the reasons why different researchers arrive at different cerebral metabolite levels despite using seemingly similar experiments.

Only minor inconsistencies were found between the concentrations of the four major cerebral metabolites investigated in this study by in vivo $^1$H-MRS and those described by classical biochemical analyses.

From the two examples of pathology given, the value of quantitative spectroscopy is immediately apparent, and continued uncertainty must attend any diagnostic applications of MRS in which a reliable form of quantitation is lacking.

EXAMPLE 3

Alzheimer Disease Studies

All patients and healthy subjects used for the study were carefully assessed with neuropsychological tests (e.g. the Mini-Mental State Examination; MMSE), MR imaging, and cerebral blood flow studies. Informed consent was obtained from patients and healthy subjects as approved by the Internal Review Board of Huntington Memorial Hospital, Pasadena, Calif. The study consisted of 11 patients (4 men and 7 women) aged 68.6 years ±8.1 with Alzheimer Disease and 10 age matched healthy subjects (4 men and 6 women) aged 69 years ±8.6. All subjects met the research criteria of Alzheimer Disease endorsed by the National Institute of Neurological and Communicative Disorders and Stroke (NINCD) and the Alzheimer Disease and Related Disorders Association (ADRDA). All healthy elderly subjects and all patients with Alzheimer Disease had an extensive neuropsychological profile based on tests of frontal, visuospatial, verbal, and memory function. The degree of dementia in the Alzheimer Disease patients was assessed with the MMSE to be mild to moderate (range of dementia 5–25; mean dementia 15; normal=30; dementia≦25). All healthy subjects were assessed with this clinical battery and were considered normal.

Images of the brain obtained with a clinical 1.5-T imager (Signa; GE Medical Systems, Milwaukee, Wis.) were used to locate two volumes (voxels) of 10–15 ml (see FIG. 13A). One voxel was located in the parietal cortex and consisted mainly of white matter. This is an area believed to be clinically involved in Alzheimer Disease. In all subjects, those regions were normal on MR images, except for evidence of atrophy. The other voxel, which consisted mostly of gray matter (gray matter), was located in the occipital cortex, an area believed to be relatively spared in Alzheimer Disease. In each voxel, localized spectra were obtained by means of a stimulated-echo sequence with a $T_R$ of 1,500 ms and a $T_E$ of 30 ms. In addition, in all healthy subjects and four patients, a second spectrum with a $T_R$ of 5,000 ms was obtained.

The use of two $T_R$ spectrums enabled calculation of saturation factors in the patients and control subjects (these factors were not statistically significantly different) and thus provided confirmation that differences in peak amplitudes were due to differences in metabolite concentrations and not due to $T_1$ relaxation effects. Differences in $T_2$ relaxation rates between patients and control subjects, which could also affect the peak intensities, were insignificant in these examinations because the $T_2$ values of brain metabolites (200–500 ms) are long compared to the short $T_E$ of 30 ms. Except for spectral phasing, fully automated data processing was used to yield peak intensities. It consisted of four steps:

1. Digital low-frequency filtering of free induction decay for additional water suppression;

2. Lorentz-Gauss transformation to obtain similar line widths in all spectra (4 Hz) and to enhance spectral resolution. The free induction decays were zero-filled to 8,192 points (0.004 ppm per point) to make an accurate frequency alignment between different spectra possible;

3. After Fourier transformation and manual zero-order phase correction, different regions in the spectrum were separately analyzed. The main resonances in the cerebral spectrum are each attributable to a single major component and appear singletlike (2.02 ppm=N-acetylaspartate (NAA), 3.03 ppm=creatine (Cr), 3.22 ppm=choline (Ch), 3.56 ppm= myo-inositol (mI).

4. To minimize the effects of overlap, the central part of each of these peaks (1.0–1.7×line width) was used to fit a Gaussian line. Because this choice may render the fitted line widths inaccurate, peak amplitudes were used for further analysis.

In use data processing is performed by a program based on a package developed and provided by General Electric. The data processing package has been extensively modified to perform the function required for use in the present invention. The program, which is written in "C," is given in Appendix 1.

At a field strength of 1.5 T, most other components that contribute substantially to the cerebral spectrum yield complex spectral patterns, caused by a strong coupling. To estimate the contribution of glutamine, an integration over a small spectral range dominated by glutamine and glutamate was performed (value A1, 2.31–2.41 ppm). Accompanying changes in the α-proton ($H_\alpha$) region of glutamate and glutamine were measured by means of an integration (value A2, 3.72–3.80 ppm). Two further integrations over the spectral ranges dominated by glucose were performed (value A3, 340–3.49 ppm; value A4, 3.74–3.86 ppm). All data reported in the tables and figures were obtained with a $T_R$ of 1,500 ms and a $T_E$ of 30 ms.

The proton spectrum of the human brain characteristically enables identification of four metabolite peaks (see FIGS. 13B and 13C). They are the N-acetylaspartate (NAA) peak at 2.02 ppm; the creatine (Cr) peak at 3.03 ppm; the choline (Ch) peak at 3.23 ppm; and the myo-inositol (mI) peak at 3.56 ppm. FIGS. 13B and 13C also define two other regions, labeled Glx (the sum of glutamine and glutamate). Although glutamine and glutamate can be further distinguished, no attempt was made to do so in this study. The α-protons of Glx resonate at 3.75 ppm, while the β and γ protons resonate between 2.1 and 2.5 ppm. The Cr peak is used as a reference for all ratios reported herein. The variation standard derivation (SD) of 13 repeated measurements in the same subject was found to be 2% for NAA, 3% for Ch, and 3% for mI.

Major differences were found between patients with Alzheimer Disease and the healthy subjects. Typical spectra from a patient and from a healthy subject are presented in FIG. 13B. In this patient, mI/Cr is noticeably elevated, NAA/Cr is reduced, and Ch/Cr is slightly increased in comparison with these ratios in the healthy subject. The consistency of the differences in mI/Cr and NAA/Cr is shown in summed spectra from eight patients (top of FIG. 13C) and eight healthy subjects (bottom of FIG. 13C).

Table VIII presents the statistical comparisons of the NAA/Cr, Ch/Cr, and mI/Cr ratios in all patients and health subjects. The difference in NAA/Cr level is small but statistically significant in both white matter and gray matter voxels. The difference in mI/Cr levels, large in both white matter and gray matter, is especially pronounced in gray matter. No statistically significant elevation exists in Ch/Cr. The increase in the area of the α-proton region of Glx (FIG. 13$b$ and 13$d$) must represent an unidentified metabolite because no corresponding change is present in the β,γ region.

TABLE VIII

In Vivo Distribution of Cerebral Metabolites in Patients with Alzheimer Disease and Healthy Elderly Subjects

| Location | NAA/Cr | Ch/Cr | mI/Cr |
|---|---|---|---|
| Parietal cortex | | | |
| Control subjects (n = 8) | 1.35 ± 0.06 | 0.83 ± 0.09 | 0.63 ± 0.007 |
| Patients (n = 11) | 1.28 ± 0.09 | 0.80 ± 0.09 | 0.70 ± 0.06 |
| Change (%) | −5.2 | −3.6 | +11.1 |
| P value | <.05 | NS | <.025 |
| Occipital cortex | | | |
| Control subjects (n = 8) | 1.25 ± 0.08 | 0.64 ± 0.07 | 0.59 ± 0.06 |
| Patients (n = 10)* | 1.14 ± 0.12 | 0.65 ± 0.05 | 0.72 ± 0.06 |
| Change (%) | −11.2 | +1.5 | +22.3 |
| P value | <.025 | NS | <.0005 |

Note:
Results of measurement is parietal (white matter) and occipital (gray matter) cortices are compared and expressed as means ± SD; P values are those obtained with the unpaired Student t test. NS = not significant.
*In one patient, the gray matter voxel was not examined for technical reasons.

Figure 14:
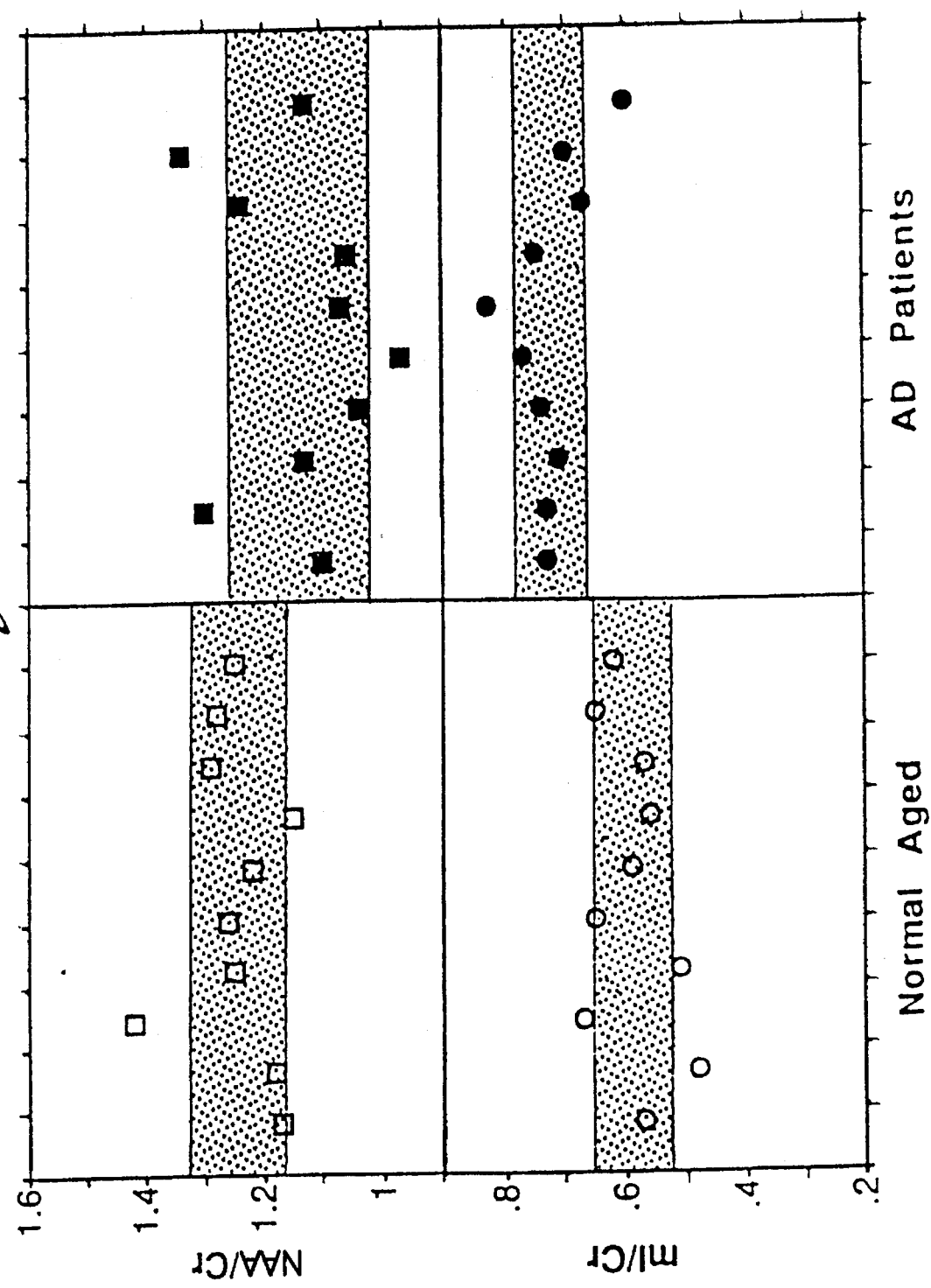
FIG. 14 illustrates the distribution of cerebral metabolite ratios in occipital cortex of patients with Alzheimer Disease and healthy subjects. The shading indicates ± one standard deviation. Each point corresponds to a single individual. □=NAA/Cr in healthy subjects, o=mI/Cr in healthy subjects, ■=NAA/Cr in patients, ●=mI/Cr in patients.
Figure 15:
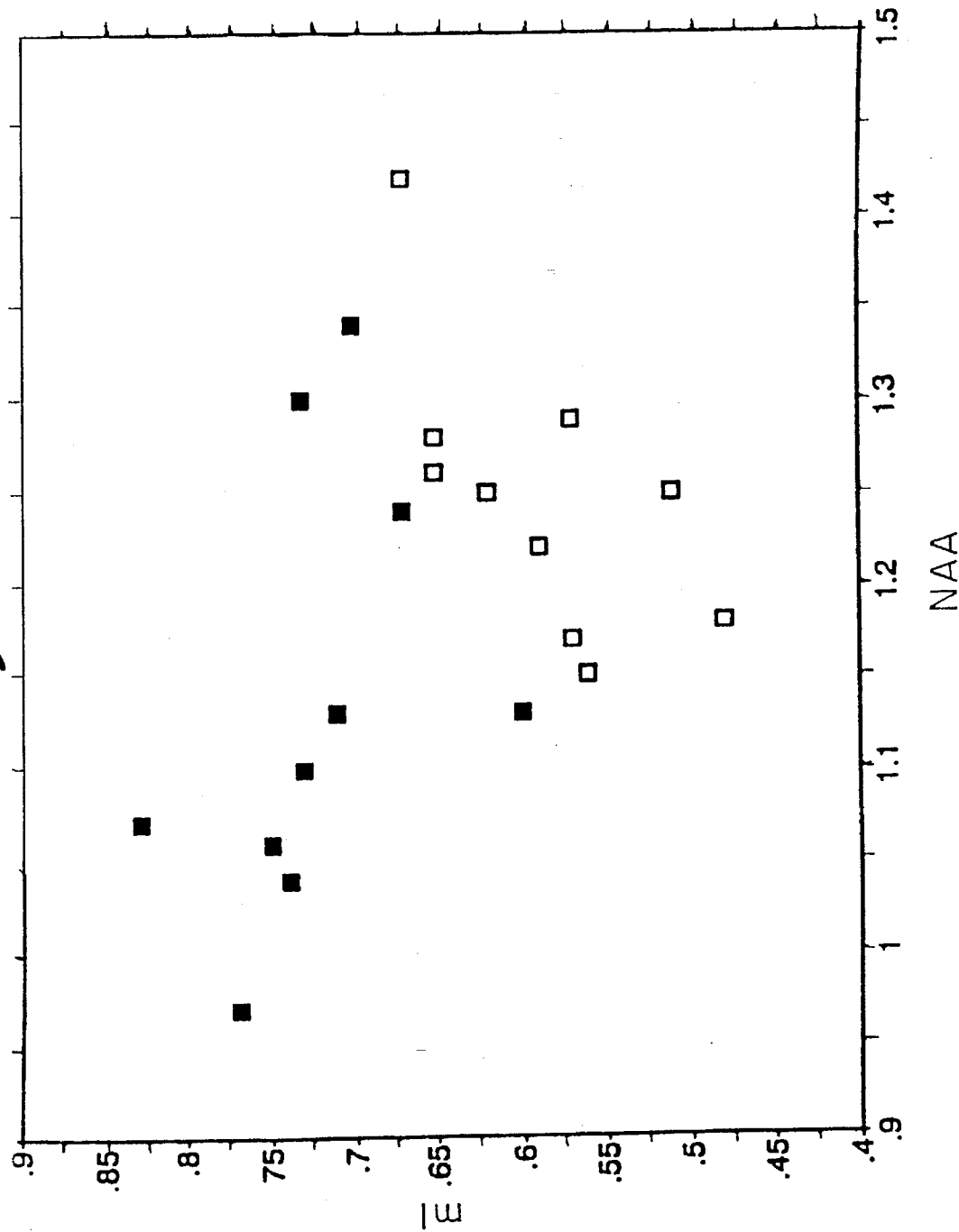
FIG. 15 illustrates a plot of mI vs. NAA in the occipital cortex of patients and healthy subjects. Patients (■) appear to be distinguished from healthy subjects (□) by the presence of elevated mI and reduced NAA in gray matter.

FIG. 14 shows result obtained from individual examinations of gray matter performed with [1]H-MR spectroscopy and demonstrates the scatter of the data. For mI, little overlap exists between patients and healthy subjects at the level of 1σ. However, the overlap for NAA is considerable. A Spearman rank test indicated that NAA/Cr was inversely correlated to mI/Cr (P=0.03). This correlation enabled further separation of patients and healthy subjects on the basis of a plot of mI versus NAA. Patients are closely grouped, and FIG. 15 supports the impression that they can be distinguished from healthy subjects on the basis of [1]H-MR spectroscopic findings. On the other hand, a multivariate analysis, performed to detect any correlation between the [1]H-MR spectroscopic findings and the severity of the disease (based on MMSE scores), showed no correlation. Age alone had no significant influence on either mI/Cr or NAA/Cr (see Table IX), so that the changes demonstrated herein are not simply an effect of accelerated aging.

TABLE IX

Effect of Increasing Age on Metabolite Ratios in Cerebral Parietal and Occipital Cortex

| Location and Metabolite Ratio | Mean Age (y) | | | | |
|---|---|---|---|---|---|
| | 25 (n = 5) | 47 (n = 12) | 53 (n = 10) | 69 (n = 10) | 79 (n = 5) |
| Parietal cortex | | | | | |
| NAA/Cr | 1.56 ± 0.07 | 1.46 ± 0.09 | 1.40 ± 0.07 | 1.35 ± 0.06 | 1.45 ± 0.10 |
| mI/Cr | 0.64 ± 0.09 | 0.61 ± 0.07 | 0.61 ± 0.07 | 0.63 ± 0.07 | 0.59 ± 0.09 |
| Occipital cortex | | | | | |
| NAA/Cr | NA | 1.32 ± 0.08 | 1.32 ± 0.04 | 1.25 ± 0.08 | NA |
| mI/Cr | NA | 0.59 ± 0.06 | 0.59 ± 0.09 | 0.59 ± 0.06 | NA |

Note.
Data are findings in health subjects in published and unpublished reports of studies performed in the Department of Magnetic Resonance Spectroscopy, Huntington Medical Research Institutes, Pasadena, Calif.
NA = Not available Some of the metabolic changes found in the above study were anticipated. The decrease in NAA, a neuronal marker, is probably due to the neuronal loss associated with Alzheimer Disease. NAA is also found to be reduced in brains of patients with Alzheimer Disease who have died.

In the regions of the brain examined, no change in Ch/Cr was seen. The concentration of free Ch is only 28 μmol/l, which is too low to contribute to observable changes in the Ch peak. At examination of brains in cadavers of patients with Alzheimer Disease, the increased degradation of phosphatidylcholine reportedly forms up to 0.5 mmol/l excess of glycerophosphoryl choline, while phosphoryl choline is unchanged. Because the total of water-soluble Ch residues (including phosphoryl choline and glycerphosphoryl choline) measured with $^1$H-MR spectroscopy is 1.5–1.6 mmol/l, any marked change in glycerphosphoryl choline in Alzheimer Disease would have been recorded as an increase in the Ch peak of the spectrum. It was not.

A new and unexpected observation is the significant increase in the mI peak in Alzheimer Disease. The mI peak consists mainly of mI but also contains a small contribution from inositol-1-phosphate and glycine. The increase in mI which amounts to approximately 1.5 mmol/kg (22% of the normal concentration). Also, there is a marked but statistically non-significant elevation of mI in cadaveric brains of patients with Alzheimer Disease.

Marked metabolic differences between patients and healthy subjects were observed, even though the study was not centered on the areas of the brain believed to be most affected by Alzheimer Disease, and no discernible abnormalities other than atrophy were seen in these regions on MR images. These biochemical differences, therefore, reflect early changes associated with Alzheimer Disease.

In a survey of some general medical diseases studies with $^1$H-MR spectroscopy, only diabetes mellitus has been found to cause a significant increase in cerebral mI, while in hepatic encephalopathy, the cerebral cortex shows a striking decrease. NAA depletion, on the other hand, is a common pathologic finding in $^1$H-MR spectroscopic studies of diseases in which neuronal concentration is decreased. A consistent finding in some preliminary studies on Alzheimer Disease is relative depletion of NAA. NAA depletion is also reported in Huntington disease and many focal and white matter diseases. Elevation of Ch metabolites appears to be a postmortem finding. Although an increase in Ch/Cr was observed in occasional spectra in this study, the average was unchanged.

EXAMPLE 4

Quantitation of Levels of Metabolites in the Brain

Fourteen patients, 5 males and 9 females all met the NINCDS-ADRDA research criteria for Alzheimer Disease. The patients and 10 normal elderly adults (4 males and 6 females), also carefully assessed by neuropsychological tests, MRI and cerebral blood flow (SPECT) studies, were examined by $^1$H-MRS. Informed consent was obtained from the patients and the normal elderly subjects as approved by the Internal Review Board of Huntington Memorial Hospital, Pasadena, Calif. The patients with Alzheimer Disease were characterized as mild to moderate by the MMSE range 5–25 (normal=30; dementia<=25). Repeated examinations were performed in 10 of the 14 patients to establish the reproducibility and the stability of MRS findings. As part of the quantitation procedures, metabolite $T_2$ and "baseline" determinations were performed in 4 subjects (2 Alzheimer Disease; 2 normal elderly).

All studies were performed on a General Electric (Waukesha, Wis., USA) Signa 1.5 T whole body MR scanner, as described above.

In contrast to methods yielding only metabolite ratios, in quantitative $^1$H-MRS studies, voxel composition was corrected for csf, brain water and solid "rest," based upon a 7 point determination of water $T_2$, acquired immediately after acquisition of the metabolite spectrum. These results were further quantified in each location by reference to an external standard.

Data processing with SA/GE is described in detail above. In the present work, the average of four methods of quantitation was used (as described above) except for the $T_1$ measurements where the two methods employing a zero point at 2.75 ppm were used, and for the $T_2$ measurements, where only the method employing the 2.75 ppm baseline determination and Lorenzian line fitting was used.

Quantitative results for the major resonances are expressed in Institutional Units with the value of 1.0 being those obtained for healthy volunteers, which are then converted to mmoles/g wet weight.

For $T_2$ determination, spectra were acquired from a larger than standard voxel (to improve S/N) centered on the occipital cortex, obtaining a minimum of 8 spectra at 6 different echo-times, $T_E$ 30–270 ms., using the methods described above. The background correction factors (defined as β), relate peak areas measured at $T_E$ 30 ms to the theoretical initial peak areas of the slower relaxing component in a double exponential fit of the $T_2$ decay data. This is used to define the 'baseline' or fast-decaying component which may contribute to observed differences in signal intensity. For difference spectroscopy, spectra were normalized to the baseline=0 at 2.75 ppm, and summed. All spectra were selected based on the lack of suppression of the second Cr peak and lack of a large lipid component. Three spectra were excluded.

For statistical comparisons, only complete examinations were included and given as N in the Tables X–XV. Of the fourteen patients, ten completed all parts of the examination. Two patients did not complete the quantitative part of the examination and one data set was excluded due to technical errors. Quantitative examinations of gray matter at $T_R$ 1.5 s were obtained in 10 patients, 6 of whom had matching quantitative $T_R$ 5.0 s data. In gray matter, all examinations in the ten normal elderly adults were completed, but water suppression was insufficient in two, and out-of-voxel lipid results were inadequately quantitated in one. Seven high quality examinations with $T_R$ 1.5 s and matching data at $T_R$ 5.0 s were analyzed. For the white matter voxel, 9 quantitative examinations for the patients were completed at $T_R$ 1.5 s and 6 had matching data at $T_R$ 5.0 s. Paired or unpaired t-tests were appropriate, rather than ANOVA (analysis of variance).

Patients with Alzheimer Disease showed a significant elevation in the mI/Cr ratio and a decrease in the NAA/Cr ratio in two brain regions compared to normal elderly subjects. The data generated shows a small, but significant, reduction in the integral β-Glx (Table X) attributed to a significant reduction in glutamine plus glutamate. An increase in glucose concentration (see below) results in increase in the α region where glucose and glutamine overlap. When examinations were repeated at intervals which varied from 2 weeks to 14 months, no significant changes between the results of the paired examinations could be detected (Table XI).

TABLE X

Effect of Probable Alzheimer Disease on Metabolite Ratios for Occipital Grey Matter (1.5 s).

Results are presented only for those subjects in whom a complete quantitative MRS examination was available. This permits direct comparison with results in Table XI.

|  | N | NAA | Ch | mI | α-Glx | β,-Glx | Glucose 1 | Glucose 2 | csf Vol % |
|---|---|---|---|---|---|---|---|---|---|
| Normal Elderly | 7 | 1.22 ± 0.06 | 0.63 ± 0.07 | 0.57 ± 0.06 | 0.38 ± 0.09 | 0.30 ± 0.05 | 0.39 ± 0.09 | 0.13 ± 0.02 | 12.0 ± 5.0 |
| Patients | 10 | 1.10 ± 0.14 | 0.64 ± 0.07 | 0.74 ± 0.08 | 0.47 ± 0.07 | 0.25 ± 0.04 | 0.49 ± 0.10 | 0.16 ± 0.06 | 23.0 ± 8.0 |
| P |  | <0.025 | n.s. | <0.0005 | <0.025 | <0.025 | <0.05 | <0.10 | <0.005 |

TABLE XI

Stability of Repeated MRS Examinations in 10 Patients with Alzheimer Disease Examinations were repeated in the same location at intervals varying between 2 weeks and 14 months. Results are means ± S.D. with P values for paired t tests. N = 10 for non-quantitative examinations, expressed as ratios/Cr. N = 4 for quantitative examinations, expressed in Institutional Units

| Metabolite Ratio | NAA/Cr | Ch/Cr | mI/Cr |  |
|---|---|---|---|---|
| Exam 1 | 1.12 ± 0.13 | 0.67 ± 0.09 | 0.75 ± 0.08 |  |
| Exam 2 | 1.11 ± 0.14 | 0.67 ± 0.08 | 0.72 ± 0.08 |  |
| P (paired t) | n.s. | n.s. | n.s. |  |
| Metabolite Concentration | NAA | Cr | Ch | mI |
| Exam 1 | 0.83 ± 0.08 | 1.03 ± 0.08 | 1.19 ± 0.17 | 1.34 ± 0.13 |
| Exam 2 | 0.87 ± 0.14 | 1.05 ± 0.11 | 1.16 ± 0.08 | 1.26 ± 0.22 |
| P (paired t) | n.s. | n.s. | n.s. | n.s. |

Quantitative determinations cannot be achieved by simply recalculating the metabolite ratios. Compared to the reference population of 10 healthy young adults, aged 24–34 yrs, which are expressed as unity, the effects of normal aging on the concentration of Cr are negligible, but a significant increase in the concentration of Ch, and a small decrease in the concentration of mI with age are apparent (Table XII). Patients with Alzheimer Disease showed a significant decrease NAA concentration and a significant increase in mI in the gray matter. Although absolute concentration of Ch is now seen to be higher in Alzheimer Disease patients than in the healthy young population, it is no greater than the change in Ch observed with normal aging.

TABLE XII

Metabolite Concentrations of Occipital Grey Matter and Parietal White Matter in Patients with Alzheimer Disease and Normal Elderly.

Quantitative $^1$H-MRS metabolite measurements were obtained for AD patients and controls in gray matter and white matter. Results are Institutional Units (using 1.0 as normal) based upon values obtained in healthy young, aged 24–34 yrs, and corrected for $T_1$ relaxation described by Kreis et al. (J. Magn. Reson. 102 9–19, 1993). Values are expressed as means ± S.D.; P values are unpaired t-tests; n.s. = not sidnificant. *Normal elderly values are significantly different from young normal subjects.

|  | NAA | Cr | Ch | mI |
|---|---|---|---|---|
| GRAY MATTER | | | | |
| TR1.5s | | | | |
| Normal Elderly (N = 7) | 1.03 ± 0.08 | 1.03 ± 0.07 | 1.14 ± 0.16* | 0.92 ± 0.17* 0.16* |
| Patients (N = 10) | 0.92 ± 0.12 | 0.96 ± 0.08 | 1.11 ± 0.17 | 1.22 ± 0.21 |
| P | <0.01 | <0.05 | n.s. | <0.005 |
| TR 5.0s | | | | |
| Normal Elderly (N = 7) | 1.01 ± 0.07 | 1.02 ± 0.10 | 1.12 ± 0.12* | 0.88 ± 0.16* 0.12* |
| Patients (N = 6) | 0.89 ± 0.10 | 0.97 ± 0.11 | 1.09 ± 0.20 | 1.35 ± 0.25 |
| P | <0.025 | n.s. | n.s. | <0.005 |
| WHITE MATTER | | | | |
| TR 1.5s | | | | |
| Normal Elderly (N = 6) | 1.00 ± 0.05 | 1.06 ± 0.08 | 1.18 ± 0.07* | 1.04 ± 0.08 |
| Patients (N = 9) | 1.02 ± 0.09 | 1.06 ± 0.10 | 1.15 ± 0.14 | 1.22 ± 0.22 |
| P | n.s. | n.s. | n.s. | <0.05 |
| TR 5.0s | | | | |
| Normal Elderly (N = 6) | 0.98 ± 0.06 | 1.03 ± 0.10 | 1.07 ± 0.09 | 1.00 ± 0.09 |
| Patients (N = 4) | 1.02 ± 0.03 | 1.02 ± 0.01 | 1.02 ± 0.05 | 1.09 ± 0.13 |
| P | n.s. | n.s. | n.s. | n.s. |

The magnitude of the increase in the concentration of mI, +30% at $T_R$ 1.5 s, and +50% at $T_R$ 5.0 s indicates an effect of $T_1$. Creatine is significantly lower in patients with Alzheimer Disease than normal elderly, but only at 1.5 s $T_R$, suggesting a small effect of $T_1$ relaxation.

Ch concentration in white matter was unaltered in this group of patients with Alzheimer Disease (Table XIII). A significant increase in the absolute concentration of mI is present. In contrast, the concentration of NAA is not significantly reduced in white matter.

TABLE XIII

Saturation Factors (SF) and T1 Relaxation Times of Cerebral Metabolites of Occipital Gray Matter and Parietal White Matter.

For spectra obtained at two different $T_R$ values, peaks were determined by Lorentzian fit at 2.75 ppm, baseline = 0. Results are means ± S.D. for 6 patients and 7 normal elderly. $T_1$ values for 10 healthy young adults are given for comparison. In white matter, the significant difference noted in $T_1$ for mI of occipital gray matter, was not present. *In Gray Matter, $T_1$ of mI was significantly longer in AD patients (P <0.07) than in normal elderly.

|  | NAA | Cr | Ch | mI |
| --- | --- | --- | --- | --- |
| GRAY MATTER | | | | |
| Normal Elderly (7) | | | | |
| SF | 0.72 ± 0.02 | 0.73 ± 0.05 | 0.69 ± 0.05 | 0.78 ± 0.07 |
| T1(s) | 1.15 | 1.12 | 1.25 | 0.96 |
| Patients (6) | | | | |
| SF | 0.73 ± 0.08 | 0.67 ± 0.05 | 0.68 ± 0.04 | 0.66 ± 0.07 |
| T1(s) | 1.11 | 1.33 | 1.30 | 1.38* |
| Healthy Young (10) T1(s) | 1.28 | 1.27 | 1.38 | 1.09 |

TABLE XIII-continued

Saturation Factors (SF) and T1 Relaxation Times of Cerebral Metabolites of Occipital Gray Matter and Parietal White Matter.

For spectra obtained at two different $T_R$ values, peaks were determined by Lorentzian fit at 2.75 ppm, baseline = 0. Results are means ± S.D. for 6 patients and 7 normal elderly. $T_1$ values for 10 healthy young adults are given for comparison. In white matter, the significant difference noted in $T_1$ for mI of occipital gray matter, was not present. *In Gray Matter, $T_1$ of mI was significantly longer in AD patients (P <0.07) than in normal elderly.

|  | NAA | Cr | Ch | mI |
| --- | --- | --- | --- | --- |
| WHITE MATTER | | | | |
| Normal Elderly (6) | | | | |
| SF | 0.73 ± 0.03 | 0.74 ± 0.05 | 0.76 ± 0.08 | 0.80 ± 0.06 |
| T1(s) | 1.16 | 1.08 | 1.03 | 0.89 |
| Patients (6) | | | | |
| SF | 0.69 ± 0.04 | 0.72 ± 0.05 | 0.77 ± 0.12 | 0.83 ± 0.12 |
| T1(s) | 1.25 | 1.15 | 0.98 | 0.82 |
| Healthy Young (10) T1(s) | 1.30 | 1.24 | 1.48 | 1.18 |

In gray matter, the saturation factors for NAA, and for Ch in the patients and the normal elderly differed by less than 2% and 6%, respectively. A small but significant difference is observed in the $T_1$ of creatine between patients and normal elderly. This explains the small difference in apparent concentration of Cr at 1.5 s already noted in Table VIII. For mI, the difference in $T_1$ of this metabolite between patients and normal elderly adults is significant at the 0.05–0.01 level, suggesting that the constituents of the mI peak may be different in patients with Alzheimer Disease. In white matter, there were no significant $T_1$ effects (Table XIII).

TABLE XIV $T_2$ Relaxation Time (s) of Metabolites in Occipital Gray Matter of patients with Alzheimer Disease, Normal Elderly and Healthy Young Adults.

Results given are the averages of $T_2$ and background correction factor (b) for patients with AD (N = 2) and for normal elderly (N = 2). Because no obvious differences were determined, results for all 4 elderly subjects were pooled for statistical comparison with a group of 10 healthy young adults. When N = 2, S.D. = range.

|  | NAA | Cr | Ch | mI |
| --- | --- | --- | --- | --- |
| AD Patients | | | | |
| T2 | 0.456 ± 0.004 | 0.201 ± 0.028 | 0.418 ± 0.042 | 0.152 ± 0.052 |
| β | 0.70 ± 0.15 | 0.85 ± 0.04 | 0.52 ± 0.16 | 0.71 ± 0.16 |
| Elderly Normal | | | | |
| T2 | 0.402 ± 0.147 | 0.186 ± 0.042 | 0.386 ± 0.019 | 0.157 ± 0.008 |
| β | 0.87 ± 0.18 | 0.93 ± 0.11 | 0.71 ± 0.27 | 0.80 ± 0.21 |
| All Elderly (4) T2 | 0.429 ± 0.118 | 0.194 ± 0.031 | 0.403 ± 0.032 | 0.155 ± 0.031 |
| Healthy Young (6) | | | | |
| T2 | 0.388 ± 0.026 | 0.207 ± 0.01 | 0.395 ± 0.073 | 0.269 ± 0.053 |
| P β | n.s. | n.s. | n.s. | 0.001 |

TABLE XIV-continued

T$_2$ Relaxation Time (s) of Metabolites in Occipital
Gray Matter of patients with Alzheimer Disease, Normal
Elderly and Healthy Young Adults.

Results given are the averages of T$_2$ and background
correction factor (b) for patients with AD (N = 2) and for
normal elderly (N = 2). Because no obvious differences were
determined, results for all 4 elderly subjects were pooled
for statistical comparison with a group of 10 healthy
young adults. When N = 2, S.D. = range.

|  | NAA | Cr | Ch | mI |
|---|---|---|---|---|
| All Elderly (4) | 0.78 ± 0.17 | 0.89 ± 0.08 | 0.64 ± 0.19 | 0.75 ± 0.156 |
| Healthy Young (6) | 0.90 ± 0.074 | 0.99 ± 0.064 | 0.88 ± 0.116 | 0.91 ± 0.059 |
| P | n.s. | n.s. | <0.05 | n.s. |

Metabolite T$_2$ determinations were performed for two principal reasons: 1) to define any contribution to the differences in metabolite ratios already established; and 2) to identify possible differences in baseline (short T$_2$) components which, if unidentified, might have the same effect.

The numerical values for T$_2$ of NAA, Cr, Ch and mI are so similar that T$_2$ differences cannot explain the observed abnormalities in the spectra of patients with Alzheimer Disease. The T$_2$ values for NAA, Cr and Ch are also indistinguishable from those previously determined for a group of healthy young adults. For mI, the T$_2$ of 155±20 ms in both Alzheimer Disease patients and normal elderly is significantly shorter than that in healthy young adults. The alterations noted could reflect changing proportions of mI, glycine and inositol-1-phosphate (IP) in patients with Alzheimer Disease, as well as differences in the local environment of mI itself.

A second reason for determining T$_2$, is to identify and quantify the fast decaying component for each of the metabolite peaks. This correction factor, defined as $\beta$, reported in Table XIV, indicates that for NAA, Ch, Cr and mI, the area due to the fast decaying component in patients with Alzheimer Disease is slightly but not significantly larger, than in the relevant normal elderly and larger in all elderly than that previously determined for healthy young adults. Only in the case of Ch does this achieve statistical significance. This may play a part in the noted increase in Ch concentration with age (+18% vs normal young adults; Table VIII). For mI despite the difference in apparent T$_2$, the ratio of the fast decaying component to the slow decaying component is not different in the patients and normal elderly or from that in young healthy adults.

TABLE XV

Metabolite Concentrations in the Brain of patients with
Alzheimer Disease and Normal Elderly.

Results are obtained by multiplying the actual
concentrations determined in the brain of healthy young
adults by the values in Institutional Units for Alzheimer
and normal elderly subjects determined in the present
study. No additional correction for T$_2$ or $\beta$ was applied,
but the difference in T$_1$ for mI is taken into account.

|  | Metabolites (mmoles/kg wet weight brain) | | | |
|---|---|---|---|---|
|  | NAA | Cr | Ch | mI |
| Elderly Control | 9.33 | 8.20 | 1.60 | 6.39 |
| Probable AD | 8.32 | 7.75 | 1.56 | 9.80 |

TABLE XV-continued

Metabolite Concentrations in the Brain of patients with
Alzheimer Disease and Normal Elderly.

Results are obtained by multiplying the actual
concentrations determined in the brain of healthy young
adults by the values in Institutional Units for Alzheimer
and normal elderly subjects determined in the present
study. No additional correction for T$_2$ or $\beta$ was applied,
but the difference in T$_1$ for mI is taken into account.

|  | Metabolites (mmoles/kg wet weight brain) | | | |
|---|---|---|---|---|
|  | NAA | Cr | Ch | mI |
| Difference from normal | −1.01 | −0.45 | −0.04 | +3.41 |
| Percentage | −11% | −5% | −2.5% | +53% |

In summary, the T$_2$ data for NAA, Cr, and Ch indicate that T$_2$ effects are not important when distinguishing the concentration difference between Alzheimer Disease patients and normal elderly at a T$_E$ of 30 ms. (Studies at longer T$_E$ are more susceptible to T$_2$ effects.) The increase in mI concentration between Alzheimer Disease patients and normal elderly is not due to T$_2$ effects either, but the altered T$_2$ of mI peaks indicate a difference in chemical composition of this complex resonance.

Figure 16:
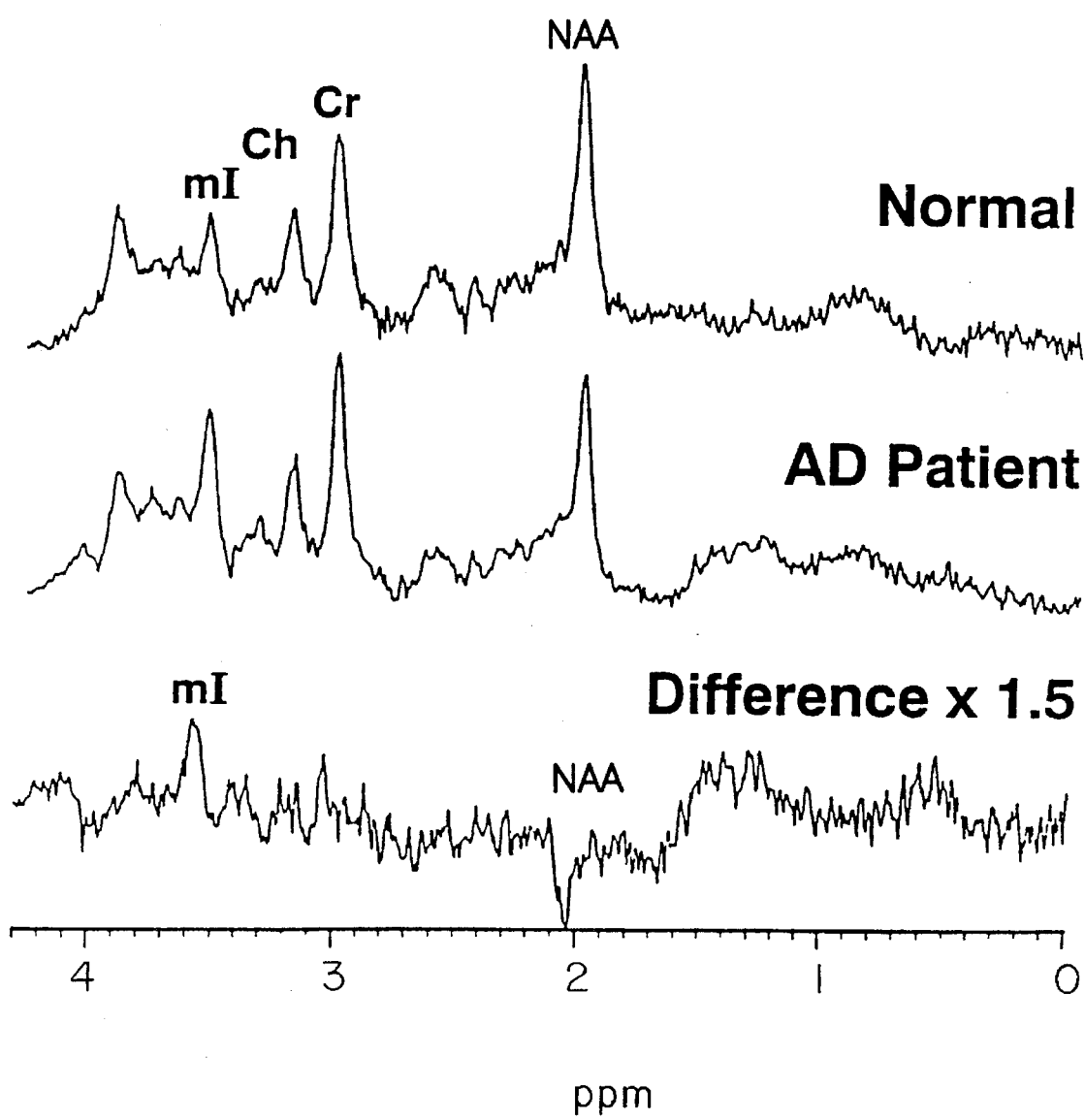
FIG. 16 illustrates abnormalities in a single Alzheimer Disease patient using difference spectroscopy.

Difference spectroscopy is a reproducible technique which helps to distinguish major peaks from "baseline" effects. The raw data for a single patient and a representative normal elderly, both of which have been corrected for the partial volume of csf and normalized to a unit volume, are plotted in FIG. 16. The positive peak at 3.56 ppm (bottom graph of FIG. 16) identifies the elevated mI concentration, while the negative peak at 2.02 ppm demonstrates that NAA concentration is reduced.

Further abnormalities are identifiable in summed difference spectra. After scaling to normalize absolute signal intensities, the most satisfactory spectra from 6 patients with Alzheimer Disease and 7 normal elderly were summed. The difference spectrum (with no further phasing) (FIG. 17) is therefore the mean difference between Alzheimer Disease and normal subjects. As well as the previously noted increase in the mI resonance at 3.56 ppm, the decrease in two resonances assigned to NAA at 2.01 and 2.2 ppm are clear. Also, very clearly identified are differences in the two glucose resonances (3.80 and 3.45 ppm). Glucose contributes to the observed increase in mI, but does not account for more than 5%. The reduction in the complex series of resonances between 2.1–2.4 ppm (β,γ-Glx) confirms the significant deficit in cerebral glutamate plus glutamine in patients with Alzheimer Disease identified in Table X.

The gray matter voxel is placed across the midline fissure and the partial csf volume has been proposed as an atrophy index. Not unexpectedly, patients with Alzheimer Disease showed a significant increase in this value from 12%±0.05 to 23%±0.08 (P=0.005) compared to normal elderly. The source of the excess glucose noted in Alzheimer Disease patients could be either brain or csf.

Because in Alzheimer Disease, as in normal subjects, glucose is three times more concentrated in the csf than in brain tissue, one would expect an 18% increase in glucose in Alzheimer Disease patients, due to the larger volume of csf in the voxel alone. A 50% increase was detected so that as much as ½ of the excess glucose in the spectrum of patients with Alzheimer Disease should be assigned to the intracerebral compartment. The same calculation permits the conclusion that lactate, observed in the spectra of 3 patients with Alzheimer Disease (not shown) is largely contributed by the included csf. For lactate, calculation of any intracerebral contribution is not reliable due to the low S/N of in vivo difference spectra.

Because appropriate measurements have now been made, it is reasonable to convert Institutional Units, given in Table XII (for gray matter only) to actual metabolite concentrations expressed in mmoles/kg wet weight of brain (Table XV). Cr concentration does not vary over a wide range within the groups and does not vary significantly between the groups. Ch concentration is also not significantly different between the Alzheimer Disease and normal elderly groups in either white or gray matter, but both values are higher than previously reported from this laboratory for 24–34 year-old healthy subjects, indicating that Ch concentration may increase with age. The NAA concentration is significantly lower (10%) in the Alzheimer Disease patients in the gray matter but not it now seems in the white matter. The mI concentration is significantly higher in the Alzheimer Disease patients (53%) in the gray matter and is also higher in the white matter (20%).

The end result is that in Alzheimer Disease, the concentration of mI (and the included metabolites) is even higher than first thought, representing an increase of >3.4 mmoles/kg wet weight rather than 1.5 mmoles/kg.

In the gray matter difference spectra, an increase of 40% in the glucose resonance at 3.45 ppm was observed; only half of which was explicable by the larger partial volume of csf. The remainder is most likely due to a small but significant increase in intracerebral glucose concentration in patients with Alzheimer Disease. From the earlier reported estimations of normal brain-glucose concentration of 0.5–1.0 mmoles/kg, the glucose concentration in this group of patients with Alzheimer Disease 1.0–1.5 mmoles/kg.

In patients with Alzheimer Disease the rate of glucose metabolism, measured either with $^{11}C$-2-deoxyglucose or with $^{18}F$-2Fluoro-deoxyglucose, is markedly depressed in many brain regions, including the occipital cortex. It is therefore possible that reduced glucose disposal rate results in a higher intracellular glucose concentration. Glucose metabolic rate (from PET) appears to be altered progressively and to be an accurate marker of the progressive severity of Alzheimer Disease.

Reduced cerebral glutamine and glutamate is seen in Alzheimer Disease for the first time in vivo, but confirms earlier post-mortem studies.

EXAMPLE 5

Diagnosis of Alzheimer Disease

Patients and healthy elderly were carefully assessed with neuropsychological tests (eg MMSE or Folstein test), MR imaging with $T_1$ weighted and $T_2$ weighted sequences and necessary laboratory tests. Patients with clinical conditions other than Alzheimer Disease were recruited after full medical diagnosis was confirmed with reference to their medical records. Diagnosis was established prospectively and again retrospectively by the referring neurologist, or by one of the referring specialists, without prior knowledge of the MRS findings. Of 118 patients with "dementia," about 40% had a prior clinical diagnosis of Alzheimer Disease, another 40% were referred as "dementia, rule out Alzheimer Disease," of which approximately 10% were "self-referred" for investigation of dementia or memory loss. In addition to MRS, all subjects underwent full neurological/neuropsychological investigation by a neurologist, psychiatrist or gerontologist, skilled in the diagnosis of Alzheimer Disease. The procedures were conducted independently, without knowledge of the outcome. MRS results were processed and stored.

At the conclusion of the trial the patients' diagnoses were established by a brief questionnaire and assigned to three groups:

(1) Alzheimer Disease (N=60);

(2) frontal lobe dementia (FLD) (N=10);

(3) other dementias (OD) (N=43).

The latter group included all remaining patients. The diagnoses and proportions of patients in this category was influenced by the referral pattern as follows: pseudo-dementia ("depression") (N=17); so-called "possible Alzheimer Disease" (N=6); multi-infarct dementia (N=3, a further 6 patients with "mixed" multi-infarct dementia and Alzheimer Disease were accordingly assigned to Alzheimer Disease); Parkinsonian dementia (N=2); normal pressure hydrocephalus (N=1); amnesia (N=1); dialysis dementia (N=1); HIV dementia (N=1); progressive aphasia (N=1); unspecified dementia (N=1); memory loss (N=1); stroke (N=1); alcohol related dementia (N=2); tumor (N=1); head injury (N=1).

At this stage, previously processed MRS data was combined and analyzed by groups. Means, SD and P values for NAA, Ch, mI, γ-Glx and β,γ-Glx ratios to Cr, atrophy index, and for quantitative values for NAA, Cr, Ch and mI were obtained.

Based on pilot MRS studies performed in 10 patients with mean difference of repeated $^1H$-MRS examinations at an interval of 21±7 days was NAA 6%, Ch 7% and mI 6%. It was thereby established that a study of 120–140 patients would provide significance at the 1%-5% level, with a power of >80%. This value of 80% is approximately the current level of certainty with which Alzheimer Disease is diagnosed clinically.

The present trial was initiated to recruit consecutive patients with dementia, until approximately 60 patients with Alzheimer Disease, an equal number (N=58) with other dementias, and controls had been examined. Sixty of the dementia patients were diagnosed clinically as Alzheimer Disease, 10 as Frontal lobe dementia (FLD) and the remaining 48 encompassed other recognized dementias, commonly required to be differentiated from Alzheimer Disease. In a parallel study to define the possible overlap with other medical conditions, 91 patients without dementia, but suffering from one of a number of other metabolic or systemic disorders, selected because of their possible influence on cerebral mI content, were studied. Twelve of the 32 age-related normal controls for this group, which was significantly younger, were also examined.

All MRS studies were performed without knowledge of the clinical diagnosis, beyond that of "dementia-rule out Alzheimer Disease." Thus the study was blind until ended, with accession of the 150th patient (includes 32 normal controls). The analysis of data was kept separate from the diagnosis until the subject had been allocated (on the basis of a diagnostic questionnaire to one or more of the referring Neurologists) to his or her group. One patient with chronic carbon monoxide poisoning was retrospectively re-assigned to the Metabolic disease group.

Informed consent was obtained from patients and healthy subjects as approved by the Internal Review Board of Huntington Memorial Hospital, Pasadena, Calif.

Each examination included axial MRI $T_1$ weighted images, for exclusion of obvious focal lesions and neurological disease, followed by qualitative (metabolite ratios) and quantitative $^1$H-MRS, to determine csf volume (as a measure of "atrophy") and metabolite concentrations. Finally, a fast-spin echo ($T_2$ weighted) image was obtained in the axial plane, to rule out the diagnosis of multi-infarct dementia (as described earlier), stroke, tumor and other $T_2$ sensitive abnormalities.

Patient compliance in this study was 99%. A shortened examination (less than 30 minutes for imaging and quantitative MRS) was adopted by examining a single location, reproducibly sited in the occipital gray matter (gray matter). Gray matter was chosen because the increase in mI is twice that seen in parietal white matter (white matter). $T_R$ 3 s, $T_E$ 30 ms and 64 acquisitions were used. In all other details, the methods were as described above.

Patients were excluded from the study using the following criteria:

a) If the patient did not tolerate all or part of the MRS examination (N=10), a second, or even a third examination was scheduled to permit inclusion in the Trial. Only 2 subjects were ultimately excluded from analysis;

b) Inclusion of a 'focal' lesion in the VOI of the relevant scout image was correctable by use of a slightly smaller voxel in the same location;

c) A panel of 3–4 spectroscopists reviewed each spectrum and the data from which it arose.

Exclusion criteria were applied as follows:

insufficient water suppression, leading to asymmetry or incomplete expression of the mI resonance;

extra-voxel lipid contamination, leading to inappropriate fitting of the NAA resonance at 2.02 ppm.

After repeating examinations where necessary, no patient was excluded on these technical grounds, but quantitative results were excluded (N=6).

Statistical tests were applied as follows: For major groups and sub-groups of 2 or more the mean and standard deviation was calculated. Ratios were tested for approximate Gaussian distribution and major groups were compared using unpaired t-tests. Individual results were plotted against another variable in the same patient to determine trends.

Specificity, sensitivity, positive predictive value and negative predictive value calculations followed the methods proposed by Altman (*Practical Statistics*, Chapman and Hall, 1991, New York). In order to establish the optimum "cut-off" for the use of mI/Cr, NAA/Cr or Ch/Cr ratio in these calculations, we established receiver-operating characteristic (ROC) curves for the tested variable. This value was different for the comparison of Alzheimer Disease with other dementias, from that found optimal for Alzheimer Disease versus normal controls.

In the case of mI/Cr a value of 0.62 was more sensitive than 0.65 (1 SD). For NAA/Cr the optimum cut-off was 1.19, rather than the 1 SD value of 1.17. For the combined use of mI and NAA, mI/Cr was plotted against NAA/Cr or a ratio mI/NAA was established.

Figure 18:
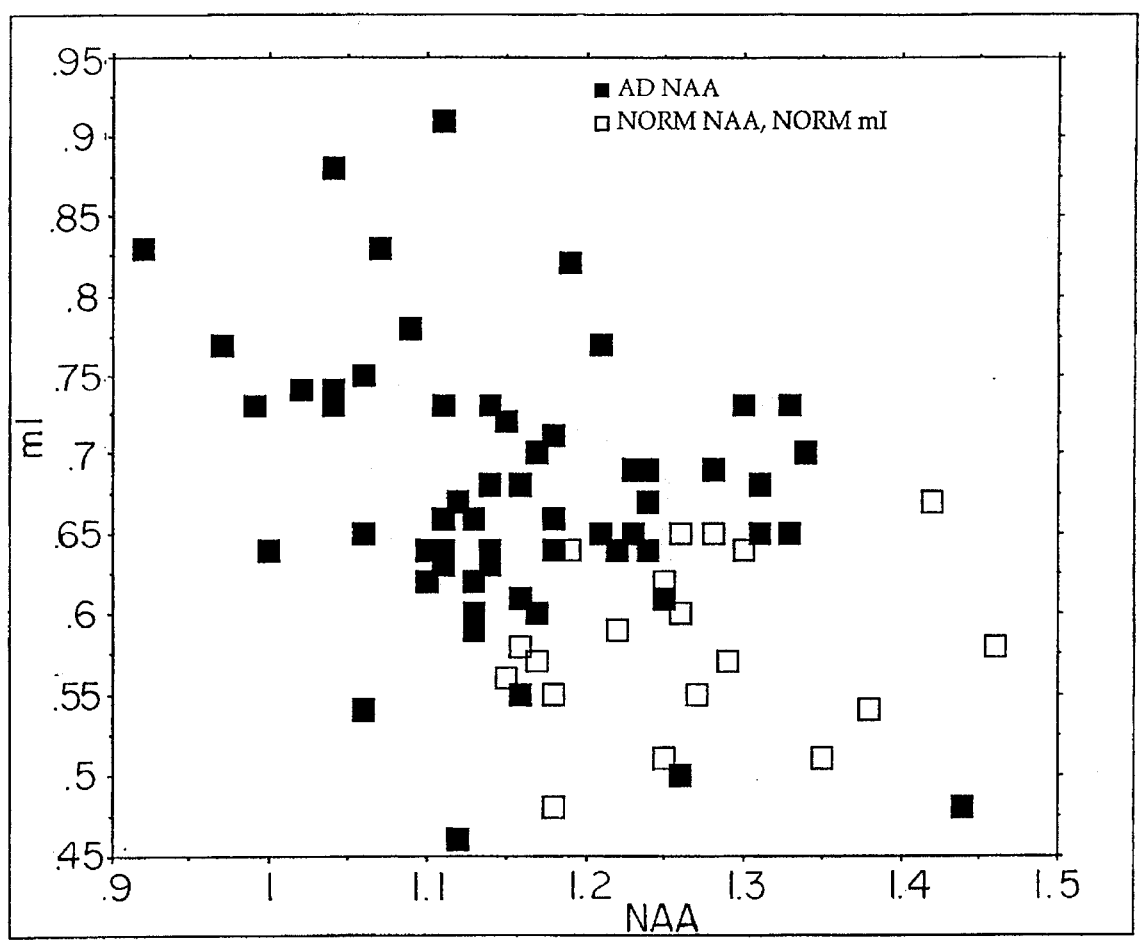
FIG. 18 shows a scattergram of mI vs. NAA for normal (□) and Alzheimer Disease patients (■)

FIG. 18 shows the characteristic changes of the $^1$H-MR spectrum in patients with Alzheimer Disease, used to define relative peak intensities of NAA, Ch, mI and Glx, using Cr intensity as the reference.

The results in this larger survey confirmed those in our earlier study (Example 4). Patients with Alzheimer Disease showed significantly reduced NAA/Cr in occipital gray matter (P<0.0005), significantly increased mI/Cr (P<0.0005) but no change in Ch/Cr (P>0.20) (Table XVI). The recently noted increase in α-Glx (P<0.01), believed to be due to excess in cerebral glucose in patients with Alzheimer Disease, are also confirmed (Table XVI).

TABLE XVI

Double Blind Trial: Alzheimer Disease vs Normal vs Other Dementias (Ratio/Cr ± SD)

| | N | Age | NAA | Ch | mI | α-Glx | β,γ-Glx |
|---|---|---|---|---|---|---|---|
| Normal (aged) | 20 | 71 ± 12 | 1.26 ± 0.09 | 0.64 ± 0.07 | 0.59 ± 0.06 | 0.42 ± 0.0 | 0.27 ± 0.07 |
| P | | | <0.0005 | >0.20 | <0.0005 | <0.01 | >0.10 |
| AD | 60 | 73 ± 9 | 1.16 ± 0.10 | 0.66 ± 0.07 | 0.68 ± 0.08 | 0.48 ± 0.1 | 0.24 ± 0.07 |
| OD | 43 | 75 ± 11 | 1.18 ± 0.11 | 0.64 ± 0.08 | 0.60 ± 0.07 | 0.44 ± 0.0 | 0.24 ± 0.05 |
| vs N | | | <0.005 | >0.35 | >0.20 | >0.15 | >0.10 |
| vs AD | | | <0.15 | <0.05 | <0.0005 | <0.05 | >0.5 |
| vs AD + FLD | | 72 ± 9 | >0.20 | <0.025 | <0.0005 | <0.05 | >0.3 |

N = Normal elderly controls
AD = Probably Alzheimer Disease
OD = All other dementias (except FLD)
FLD = Frontal lobe dementia In contrast to the foregoing groups of Alzheimer Disease, the combined group of "other dementias" failed to demonstrate any significant increase in mI/Cr ratio, and would thereby be distinguishable as a group (P<0.0005) from either Alzheimer Disease or FLD. On the other hand, NAA/Cr in this group of other dementias was significantly reduced compared to controls (P<0.005), and could not be distinguished on this basis alone from the group of patients with Alzheimer Disease (P>0.15) (Table XVI). For clarity, the major differences between these groups and the combined group of "Other Dementias", including the absolute Cr concentration in Institutional Units, and the atrophy index (csf volume in the voxel).

Frontal lobe dementia (FLD), a group which has only in recent years been clinically and neuropathologically separated from Alzheimer Disease, also showed a significant increase in mI/Cr and a significant reduction in NAA/Cr in the occipital grey matter. Ch/Cr was not significantly increased in patients with FLD compared to normal controls (Table XVII).

TABLE XVII

Double Blind Trial: Frontal Lobe Dementia (Ratio/Cr ± SD)

|  | Age | NAA | Ch | mI | α-Glx | β,γ-Glx |
|---|---|---|---|---|---|---|
| Normal (aged) | 67 ± 9 | 1.20 ± 0.11 | 0.67 ± 0.04 | 0.67 ± 0.06 | 0.45 ± 0.05 | 0.28 ± 0.04 |
| P vs N |  | <0.0005 | >0.15 | <0.0005 | <0.01 | >0.10 |
| P vs AD | >0.20 |  | >0.35 | >0.45 | >0.15 | <0.025 |
| P vs OD | >0.10 |  | <0.15 | <0.005 | >0.10 | >0.30 |

Table XIII shows the distribution of data obtained in the various dementias comprising the group "Other Dementias". Only in the instances of "pseudodementia (depression)" and "possible Alzheimer Disease" are the numbers sufficient for independent statistical analysis. Myo-inositol/Cr is indistinguishable from controls, but the reduction of NAA/Cr is statistically significant in each case ($P < 0.01$ and $<0.01$, respectively).

amyotrophic lateral sclerosis, no significant elevation is noted, whereas some patients had elevated values. On the other hand, patients with neurological symptoms attributed to (tryptophan induced) eosinophilic myalgia, showed no such change. Other diseases tested because they appear in lists of causes of dementia, had no effect on mI/Cr and NAA/Cr is generally unaffected. Exceptions are the isolated detection of mI/Cr elevation in two patients, in one young diabetic patient, and one elderly subject with Down syndrome (neurofibrillary tangles and plaque occur in Down syndrome), in an elderly woman with severe mental changes attributed to chronic carbon monoxide toxicity, and in local regions of multiple sclerosis plaque.

TABLE XVIII

Other Dementias: Patients Presenting as Dementia Other than AD or FLD.

| Diagnosis | N | NAA | Ch | mI | α-Glx | β-Glx |
|---|---|---|---|---|---|---|
| Multi-infarct | 3 | 1.20 ± 0.02 | 0.65 ± .04 | 0.62 ± 0.02 | 0.42 ± 0.04 | 0.26 ± 0.03 |
| Parkinson's | 2 | 1.19 ± 0.03 | 0.65 ± .06 | 0.66 ± 0.01* | 0.42 ± 0.02 | 0.28 ± 0.00 |
| Normal Pressure Hydrocephalus | 1 | 1.07 | 0.62 | 0.49 | 0.34 | 0.25 |
| Amnesia | 1 | 1.12 | 0.53 | 0.58 | 0.15 | 0.20 |
| Dialysis | 1 | 1.02 | 0.64 | 0.57 | 0.39 | 0.21 |
| HIV | 1 | 1.53 | 0.84 | 0.69* | 0.42 | 0.23 |
| Possible Alzheimer Disease | 6 | 1.15 ± 0.06 | 0.65 ± .08 | 0.60 ± 0.08 | 0.45 ± 0.08 | 0.23 ± 0.06 |
| Depression | 16 | 1.19 ± 0.11 | 0.64 ± .09 | 0.59 ± 0.07 | 0.47 ± 0.05 | 0.25 ± 0.05 |
| Progressive Aphasia | 1 | 1.17 | 0.58 | 0.61 | 0.33 | 0.20 |
| WM Disease | 1 | 1.24 | 0.59 | 0.52 | 0.40 | 0.23 |
| Memory Loss | 1 | 1.12 | 0.53 | 0.58 | 0.15 | 0.20 |
| Stroke | 1 | 1.24 | 0.64 | 0.62 | 0.27 | 0.27 |
| Alcohol Related | 2 | 1.21 ± 0.10 | 0.65 ± 0.01 | 0.62 ± 0.01 | 0.58 ± 0.12 | 0.27 ± 0.04 |
| Tumor | 1 | 1.31 | 0.57 | 0.56 | — | — |
| Head Injury | 1 | 1.13 | 0.62 | 0.66 | — | — |

Several systemic disorders influence the mI/Cr ratio as determined in the cerebral gray matter. Most notable are diabetes mellitus and chronic renal failure (Table XIX). In

TABLE XIX

Metabolic and Systemic Diseases Patients with relevant clinical conditions, but without dementia or metabolic disorders which may increase cerebral mI/Cr.

| Diagnosis | N | NAA | Ch | mI | α-Glx | β-Glx |
|---|---|---|---|---|---|---|
| Amyotrophic Lateral Sclerosis | 7 | 1.26 ± 0.08 | 0.70 ± 0.08 | 0.63 ± 0.11 | 0.49 ± 0.17 | 0.32 ± 0.04 |
| Renal Failure | 17 | 1.23 ± 0.10 | 0.66 ± 0.06 | 0.64 ± 0.08 | 0.41 ± 0.08 | 0.26 ± 0.04 |
| Diabetes Mellitus | 21 | 1.36 ± 0.15 | 0.85 ± 0.08 | 0.69 ± 0.05 | 0.55 ± 0.09 | 0.21 ± 0.04 |
| Multiple Sclerosis | 5 | 1.26 ± 0.13 | 0.85 ± 0.15 | 0.75 ± 0.10 | 0.57 ± 0.16 | 0.27 ± 0.11 |
| Down Syndrome | 2 | 1.38 | 0.66 | 0.74 | 0.36 | 0.28 |
| Carbon Monoxide | 1 | 1.05 | 0.60 | 0.75 | 0.52 | 0.25 |
| Eosinophilic Myalgia | 12 | 1.29 ± 0.06 | 0.61 ± 0.05 | 0.58 ± 0.05 | 0.39 ± 0.09 | 0.28 ± 0.04 |
| Endocrine | 6 | | | | | |
| Hepatic Encephalopathy | 1 | 1.08 | 0.55 | 0.26 | 0.65 | 0.42 |
| Wilsons Disease | 1 | 1.24 | 0.56 | 0.48 | 0.43 | 0.41 |
| Hypoxia/Cardiac | 2 | 1.16 ± 0.00 | 0.85 ± 0.05 | 0.55 ± 0.04 | 0.62 ± 0.14 | 0.29 ± 0.04 |
| Subdural Hematoma | 1 | 1.43 | 0.79 | 0.57 | 0.52 | 0.28 |
| Hydrocephalus | 1 | 1.45 | 0.49 | 0.44 | 0.39 | 0.22 |
| Rasmussin's Encephalitis | 2 | | | | | |

Myo-inositol/Cr vs NAA/Cr for all 60 patients with Alzheimer Disease and the relevant normal elderly controls. Calculated sensitivity, specificity, positive and negative predictive values for mI/Cr, or for NAA/Cr alone, or for mI and NAA together are presented in Table XX. They confirm a high degree of success in distinguishing patients with Alzheimer Disease from normal, reaching over 80% for mI/Cr, and a positive predictive value of 98% when NAA is included in the evaluation.

TABLE XX

Short Echo MRS for Diagnosis Alzheimer vs Normal, and vs Other Dementias

| | Alzheimer vs Normal mI/NAA | Alzheimer vs Other mI/Cr |
|---|---|---|
| Sensitivity | 83% | 82% |
| Specificity | 95% | 64% |
| Positive Predictive Value | 98% | 74% |
| Negative Predictive Value | 65% | 80% |

Figure 19:
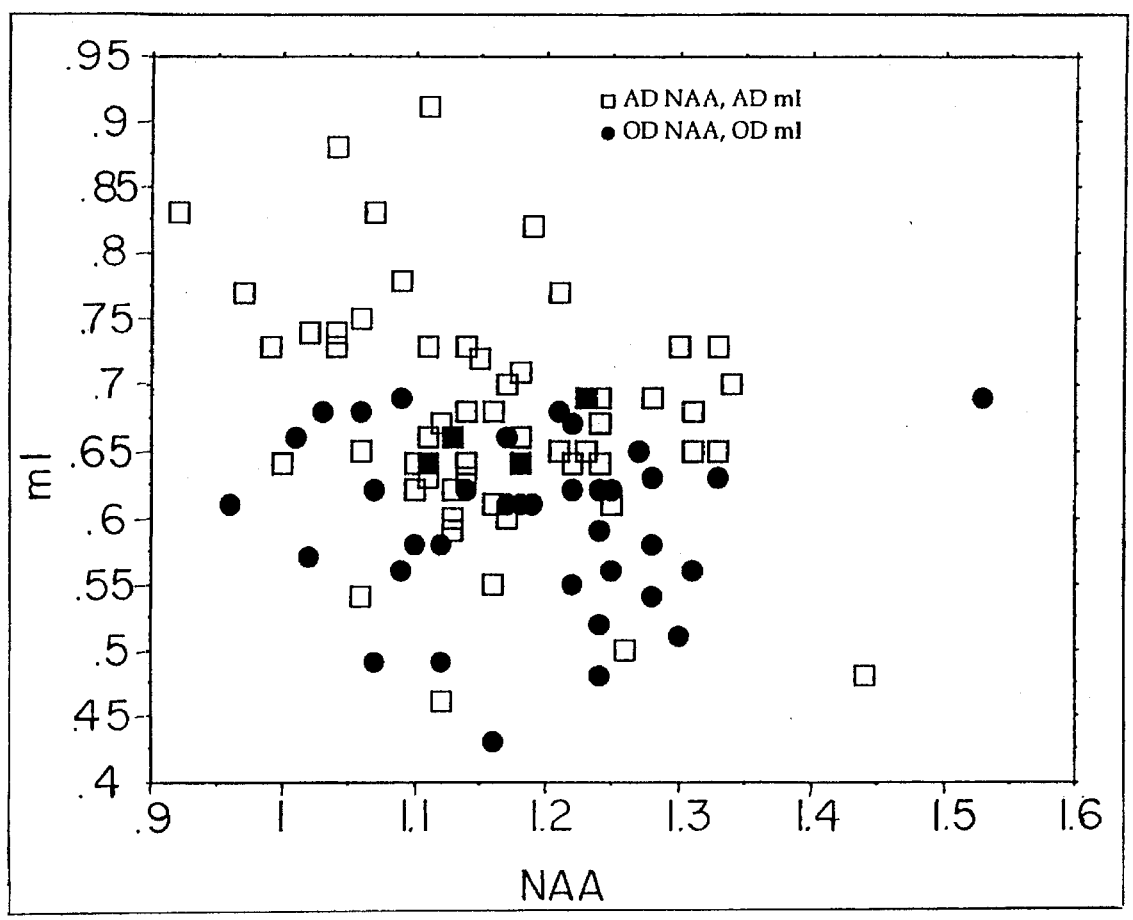
FIG. 19 shows a scattergram of mI vs. NAA for Alzheimer Disease patients (□) and patients with other forms of dementia (o)

There is a greater overlap in NAA/Cr when $^1$H-MRS values are applied to the distinction between Alzheimer Disease and the several other dementias as a group (FIG. 19). However, a positive predictive value for Alzheimer Disease based upon mI/Cr alone reaches 74%, while sensitivity of 82% is achieved (Table XX). Many patients in both groups have reduced NAA/Cr, so NAA/Cr does not distinguish between the two groups and improves very little the specificity with which mI/Cr effects the diagnosis of Alzheimer Disease. In particular, the negative predictive value of 80% suggests that short echo $^1$H-MRS may be an effective test to rule out Alzheimer Disease in an elderly population at risk.

Figure 20:
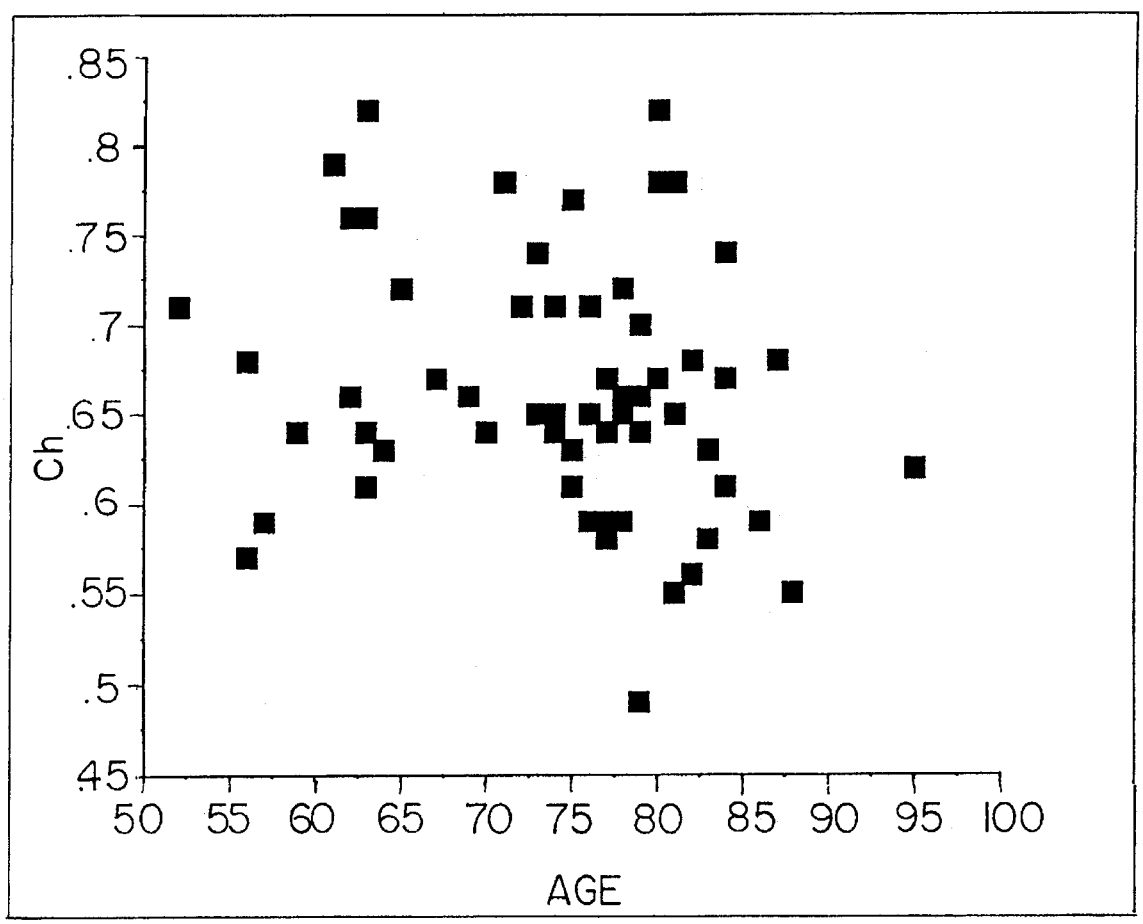
FIG. 20 shows a scattergram of Choline concentration vs. age for normal individuals.
Figure 21:
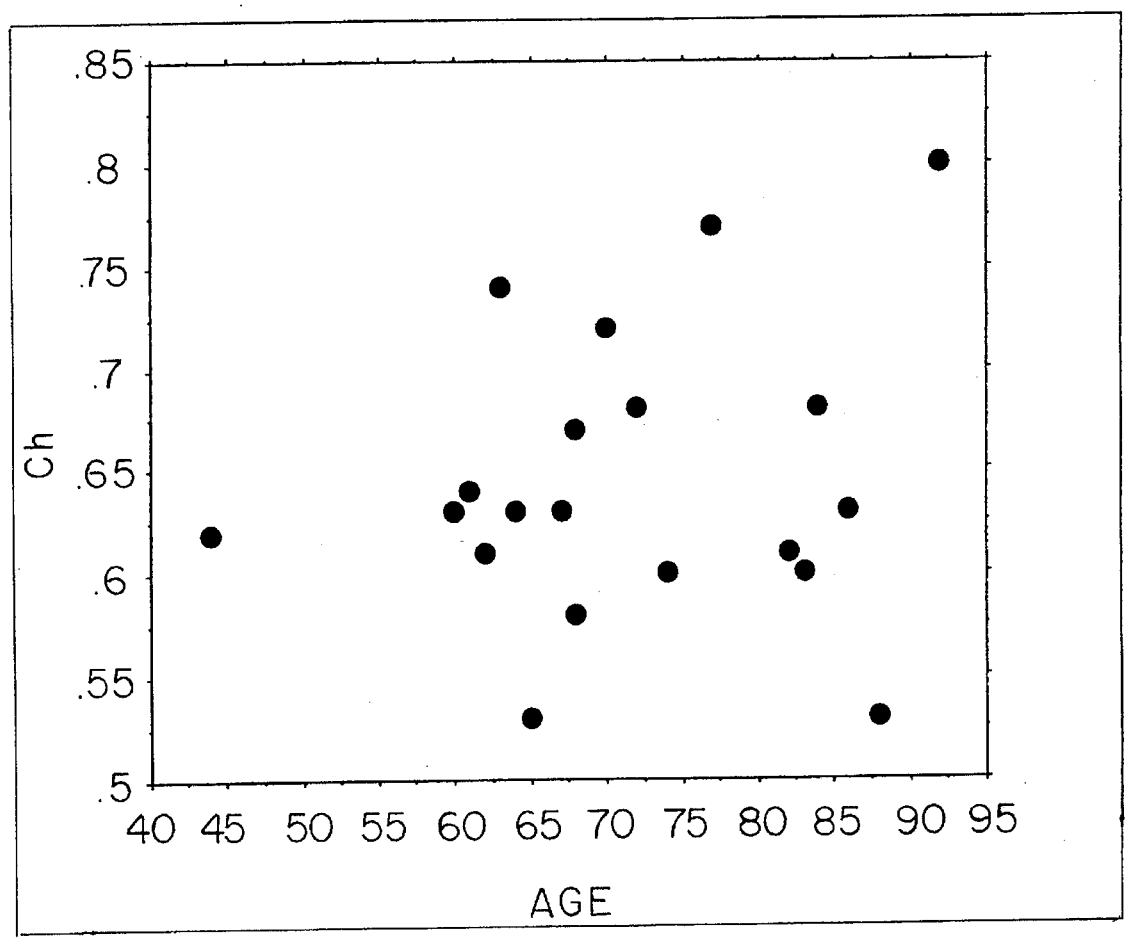
FIG. 21 shows a scattergram of Choline concentration vs. age for Alzheimer Disease patients.

Alzheimer Disease and other dementias are differentiated by a very small but significantly higher Ch/Cr in the Alzheimer Disease group. It is not clear whether even this small effect is due to age alone. FIG. 20 plots the age-related changes in Ch/Cr for normals, while FIG. 21 shows similar results for Alzheimer Disease patients. At younger ages, it is possible that Ch/Cr is higher in Alzheimer Disease than in controls.

$^1$H-MRS when applied alone to the notably difficult task of identifying patients with Alzheimer Disease does so with a satisfying sensitivity of 83% and a specificity and positive predictive value of 95% and 98%, respectively. Even greater precision might be achieved by combining this test with another existing differentiator, that of medial temporal lobe thickness. In a clinical setting however, what is required is the differentiation of Alzheimer Disease from any of the many treatable or untreatable causes of dementia which may be confused with it, and for which the management will often be very different. In this task, $^1$H-MRS also seems to offer considerable promise. While the reduction in NAA/Cr offers little help, mI/Cr does distinguish with a sensitivity of 82%. While specificity is only 64%, the negative predictive value achieves a useful level of 80%. It should be remembered that the clinical "Gold Standard" for diagnosis of Alzheimer Disease is probably no better than 80%, and that a significant proportion of patients with Alzheimer Disease are included in the Other Dementias group on this basis.

The above descriptions of exemplary embodiments of methods for the diagnosis of clinical conditions and for the quantitation of biochemicals in vivo are for illustrative purposes. Because of variations which will be apparent to those skilled in the art, the present invention is not intended to be limited to the particular embodiments described above. The present invention may also be practiced in the absence of any element not specifically disclosed. The scope of the invention is defined by the following claims.

What is claimed is:

1. A method for diagnosing Alzheimer Disease comprising:
   defining a volume within the brain of a patient suspected of suffering from Alzheimer Disease;
   obtaining a magnetic resonance spectrum of the defined volume;
   suppressing water peak;
   correcting the baseline of the spectrum;
   locating peaks for creatine, myo-inositol and N-acetylaspartate;

determining the peak height of myo-inositol relative to the peak height of creatine;

determining the peak height of N-acetylaspartate relative to the peak height of creatine;

comparing the relative peak heights of myo-inositol relative to creatine and N-acetylaspartate relative to creatine in the patient to the relative peak heights of myo-inositol relative to creatine and N-acetylaspartate relative to creatine for a normal population, wherein an increase in the relative peak height of myo-inositol and a decrease in the relative peak height of N-acetylaspartate is diagnostic of Alzheimer Disease.

2. A method as recited in claim 1 wherein the step of locating the peaks for creatine, myo-inositol and N-acetylaspartate further comprises locating the N-acetylaspartate peak at a chemical shift of 2.02 ppm, locating the creatine peak at a chemical shift of 3.03 ppm and locating the myo-inositol peak at a chemical shift of 3.56 ppm.

3. A method as recited in claim 1 wherein the step of defining a volume within the brain comprises defining a volume located in the gray matter of the occipital cortex of a brain.

4. A method as recited in claim 1 further comprising the step of displaying a myo-inositol peak with echo times below 100 ms.

5. A method of quantitating metabolites identified by a magnetic resonance spectrum comprising:

defining a volume within the brain;

obtaining a magnetic resonance spectrum of the defined volume;

measuring the visible and invisible water content of the defined volume;

suppressing the signal from water to reveal the spectra from metabolites;

correcting the baseline;

obtaining a magnetic resonance spectrum of a standard;

comparing the signal from the metabolites to the signal from the standard; and calculating the in vivo concentration of the metabolites.

6. A method as recited in claim 5 wherein the step of measuring the visible and invisible water content of the defined volume, comprises the step of determining the water content of cerebrospinal fluid and brain tissue water in the defined volume.

7. A method as recited in claim 5 wherein the step of defining a volume within the brain comprises defining a volume in the gray matter of the occipital cortex.

8. A method as recited in claim 5 wherein the step of obtaining a magnetic resonance spectrum of a standard comprises the use of an external standard.

9. A method as recited in claim 8 wherein the step of obtaining a magnetic resonance spectrum of an external standard comprises using 2-(trimethylsilyl)ethanol.

10. A method as recited in claim 5 wherein the step of defining a volume within the brain comprises defining a volume in the white matter of the brain.

11. A method as recited in claim 5 wherein the step of measuring the visible and invisible water content of the defined volume comprises measuring the $T_2$ decay of the magnetic resonance spectrum of the defined volume due to water.

12. A method as recited in claim 11 further comprising the step of analyzing the $T_2$ decay with double-exponential analysis.

13. A method as recited in claim 12 further comprising the step of calculating brain and cerebrospinal fluid compartments of the defined volume using the $T_2$ decay double-exponential analysis.

14. A method as recited in claim 5 wherein the step of calculating the in vivo concentration of the metabolites comprises calculating the concentration of metabolites selected from the group consisting of myo-inositol, choline, creatine, N-acetylaspartate, glutamine, glutamate, lactate, and lipid.

15. A method as recited in claim 5 further comprising the step of comparing the in vivo concentrations of the metabolites with normal values of concentrations of the metabolites of age matched persons not suffering from diseases or conditions which affect the brain.

* * * * *

UNITED STATES PATENT AND TRADEMARK OFFICE
CERTIFICATE OF CORRECTION

PATENT NO. : 5,617,861
DATED : April 8, 1997
INVENTOR(S) : Brian Ross; Thomas Ernst; Roland Kreis It is certified that error appears in the above-indentified patent and that said Letters Patent is hereby corrected as shown below:

Column 2, line 19, change "situation" to -- situations --.
Column 5, line 15, change "emphasize" to -- emphasized --.
Column 6, line 47, change "1%," to -- 1%. --.
Column 7, line 32, change "$T_1i$" to -- $T_{1i}$ --.
Column 8, line 35, Formula 9, that portion of the formula reading "$\approx Vs_{csf}$" should read -- $\cong Vs_{csf}$ --.
Column 9, line 40, Formula 19, that portion of the formula reading "$ct_v$" should read -- $ct_{v'}$ --.
Column 18, line 39, change "Corresponding" to -- corresponding --.
Column 25, line 25, change "ml" to -- mI --.
Column 27, line 32, change "diseases" to -- disease --.

Signed and Sealed this

Fourteenth Day of April, 1998

*Attest:*

BRUCE LEHMAN

*Attesting Officer*    Commissioner of Patents and Trademarks